US008573030B2

(12) United States Patent
Gole

(10) Patent No.: US 8,573,030 B2
(45) Date of Patent: Nov. 5, 2013

(54) GAS SENSORS, METHODS OF PREPARATION THEREOF, METHODS OF SELECTING GAS SENSOR MATERIALS, AND METHODS OF USE OF GAS SENSORS

(75) Inventor: James L. Gole, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 259 days.

(21) Appl. No.: 13/031,430

(22) Filed: Feb. 21, 2011

(65) Prior Publication Data

US 2011/0197657 A1 Aug. 18, 2011

Related U.S. Application Data

(63) Continuation-in-part of application No. PCT/US2009/054596, filed on Aug. 21, 2009.

(60) Provisional application No. 61/090,682, filed on Aug. 21, 2008.

(51) Int. Cl.
| | |
|---|---|
| G01N 9/00 | (2006.01) |
| G01R 27/28 | (2006.01) |
| H01L 21/02 | (2006.01) |
| G01N 27/02 | (2006.01) |

(52) U.S. Cl.
CPC .................................... G01N 27/021 (2013.01)
USPC .............. 73/23.2; 73/31.05; 73/1.01; 438/49; 324/649

(58) Field of Classification Search
USPC ............................ 73/1.06, 28.01, 23.2–31.07, 73/335.01–335.14
See application file for complete search history.

(56) References Cited

U.S. PATENT DOCUMENTS

| | | |
|---|---|---|
| 3,640,901 A | 2/1972 | Walker et al. |
| 4,294,891 A | 10/1981 | Yao et al. |
| 4,706,493 A | 11/1987 | Chang et al. |
| 5,004,424 A | 4/1991 | Larminie |
| 5,074,987 A | 12/1991 | Thompson |
| 5,242,863 A | 9/1993 | Xiang-Zheng et al. |
| 5,262,034 A | 11/1993 | Kunz et al. |
| 5,641,585 A | 6/1997 | Lessing et al. |
| 5,759,712 A | 6/1998 | Hockaday |
| 5,801,092 A | 9/1998 | Ayers |
| 5,882,496 A | 3/1999 | Northrup et al. |
| 6,004,450 A | 12/1999 | Northrup et al. |
| 6,062,210 A | 5/2000 | Welles |
| 6,123,828 A | 9/2000 | Williams et al. |
| 6,174,677 B1 | 1/2001 | Vo-Dinh |
| 6,180,497 B1 | 1/2001 | Sato et al. |
| 6,277,765 B1 | 8/2001 | Cheng et al. |
| 6,277,766 B1 | 8/2001 | Ayers |
| 6,289,888 B1 | 9/2001 | Welles |
| 6,312,846 B1 | 11/2001 | Marsh |
| 6,342,071 B1 | 1/2002 | Pless |
| 6,380,550 B1 | 4/2002 | Canham et al. |
| 6,391,808 B1 * | 5/2002 | Stiegman ........................ 501/12 |
| 6,413,446 B1 | 7/2002 | Mechtel et al. |

(Continued)

*Primary Examiner* — Hezron E Williams
*Assistant Examiner* — Alexander Mercado
(74) *Attorney, Agent, or Firm* — Thomas | Horstemeyer, LLP

(57) ABSTRACT

Embodiments of the present disclosure provide for methods of selecting a nanostructured deposit for a conductometric gas sensor, methods of detecting a gas based on the acidic or basic characteristic of the gas using a conductometric gas sensor, devices including conductometric gas sensors, arrays of conductometric gas sensors, methods of determining the acidic or basic characteristic of a gas, methods of treating a sensor, and the like.

25 Claims, 23 Drawing Sheets

(56) References Cited

U.S. PATENT DOCUMENTS

| | | |
|---|---|---|
| 6,491,391 B1 | 12/2002 | Blum et al. |
| 6,500,770 B1 | 12/2002 | Cheng et al. |
| 6,517,203 B1 | 2/2003 | Blum et al. |
| 6,527,943 B1 | 3/2003 | Zhang et al. |
| 6,589,883 B2 | 7/2003 | Gole et al. |
| 6,619,799 B1 | 9/2003 | Blum et al. |
| 6,627,964 B2 | 9/2003 | Nakashima et al. |
| 6,673,644 B2 | 1/2004 | Gole et al. |
| 6,689,700 B1 | 2/2004 | Watkins et al. |
| 6,734,000 B2 | 5/2004 | Chin et al. |
| 6,828,253 B2 | 12/2004 | Gole et al. |
| 6,893,892 B2 | 5/2005 | Gole et al. |
| 6,906,392 B2 | 6/2005 | Benzel et al. |
| 7,013,708 B1 | 3/2006 | Cho et al. |
| 7,186,669 B2 | 3/2007 | Gole et al. |
| 7,838,949 B2 | 11/2010 | Gole et al. |
| 8,230,720 B2 * | 7/2012 | Serban et al. ............... 73/24.01 |
| 2003/0008966 A1 | 1/2003 | Vane et al. |
| 2003/0170480 A1 | 9/2003 | Gorman et al. |
| 2004/0192003 A1 | 9/2004 | Sandhu et al. |
| 2005/0193800 A1 * | 9/2005 | DeBoer et al. ............... 73/1.06 |
| 2008/0093423 A1 | 4/2008 | Kodas et al. |
| 2008/0199529 A1 | 8/2008 | Franzen et al. |

* cited by examiner

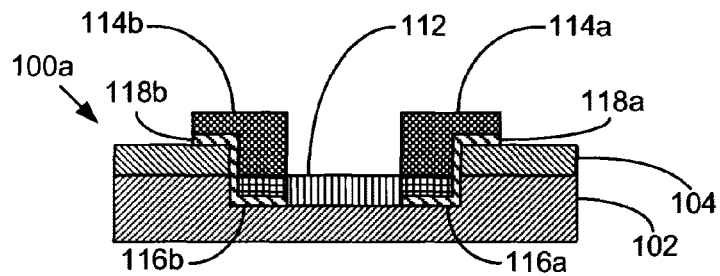
FIG. 1.1A
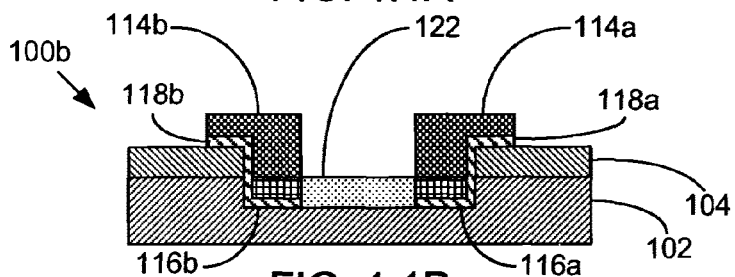
FIG. 1.1B
FIG. 1.2A
FIG. 1.2B
FIG. 1.2C
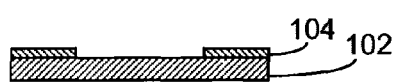
FIG. 1.2D
FIG. 1.2E
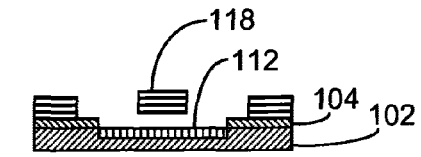
FIG. 1.2F
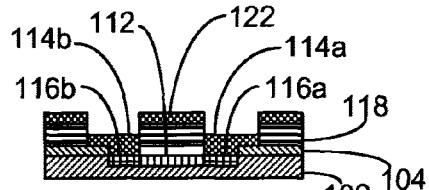
FIG. 1.2G
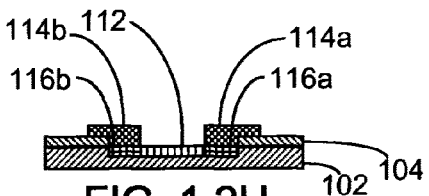
FIG. 1.2H
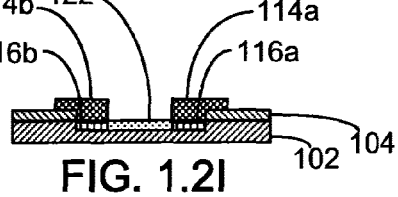
FIG. 1.2I

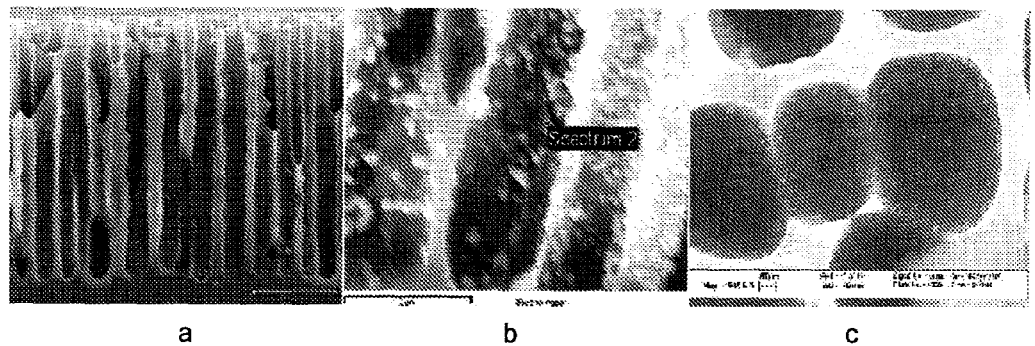
FIG. 2.1
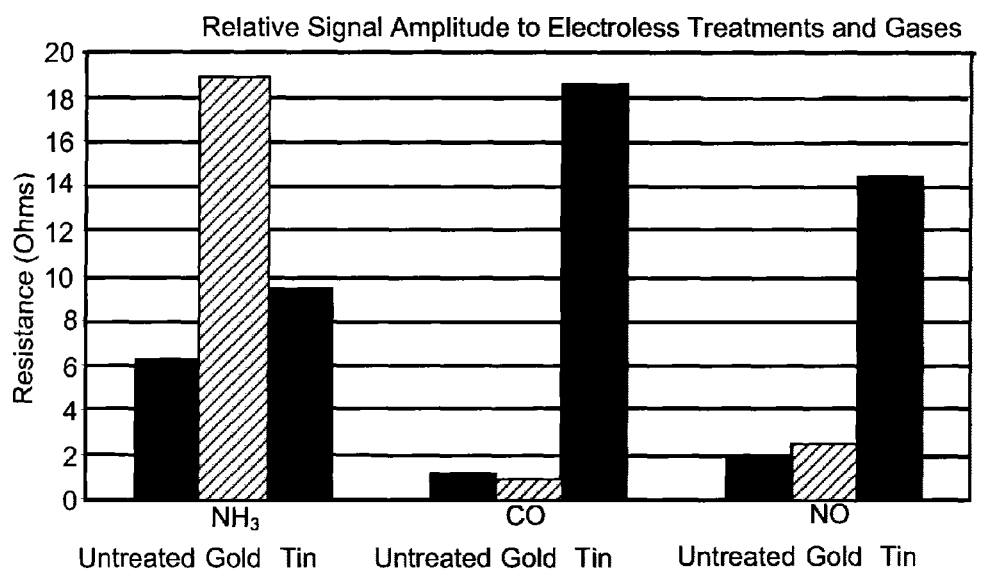
FIG. 2.2

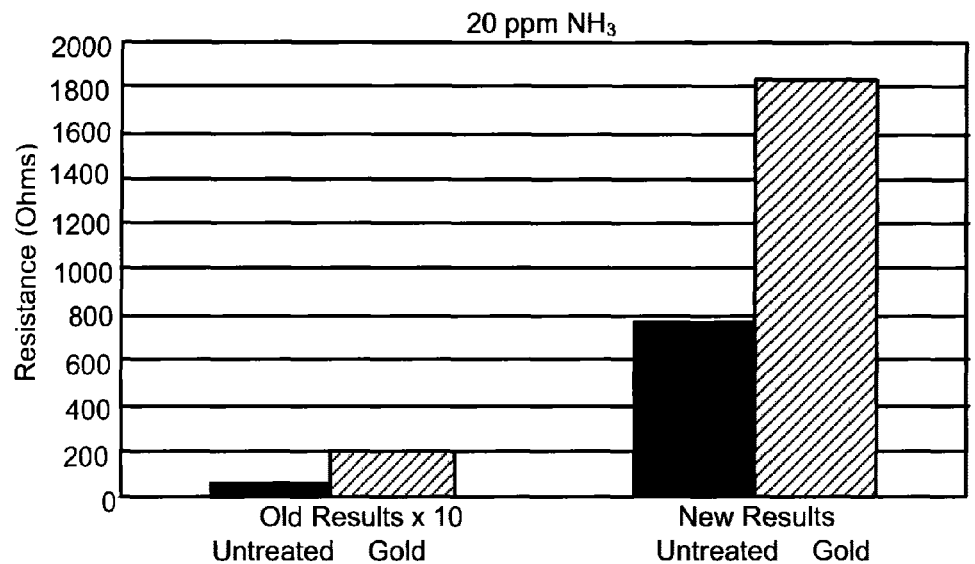
FIG. 2.3
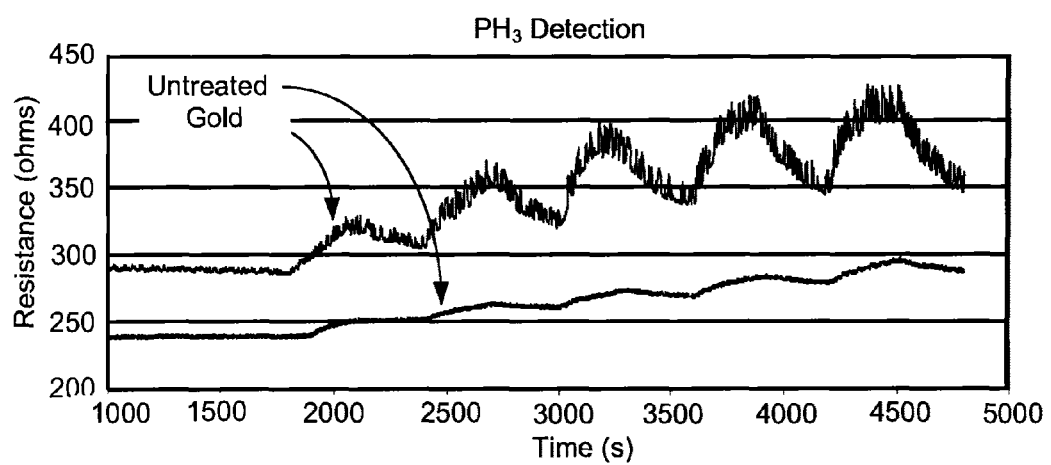
FIG. 2.4

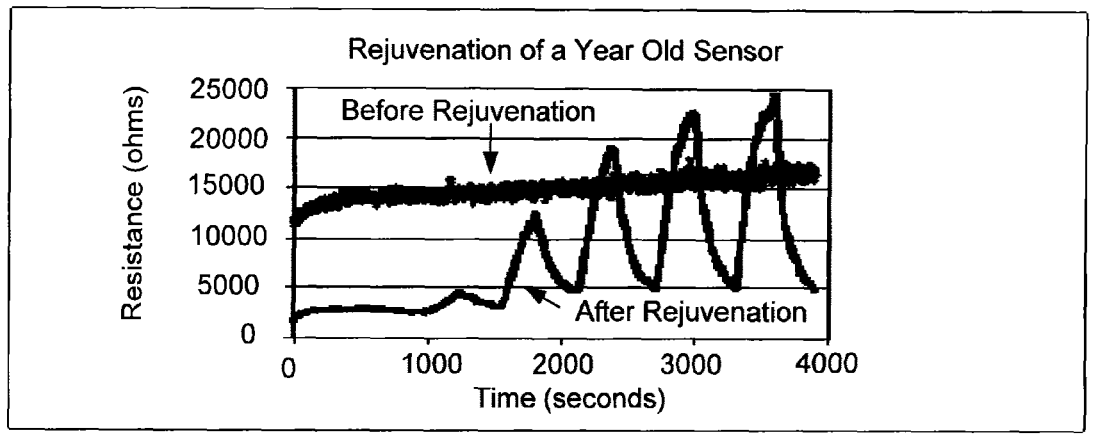
FIG. 2.5
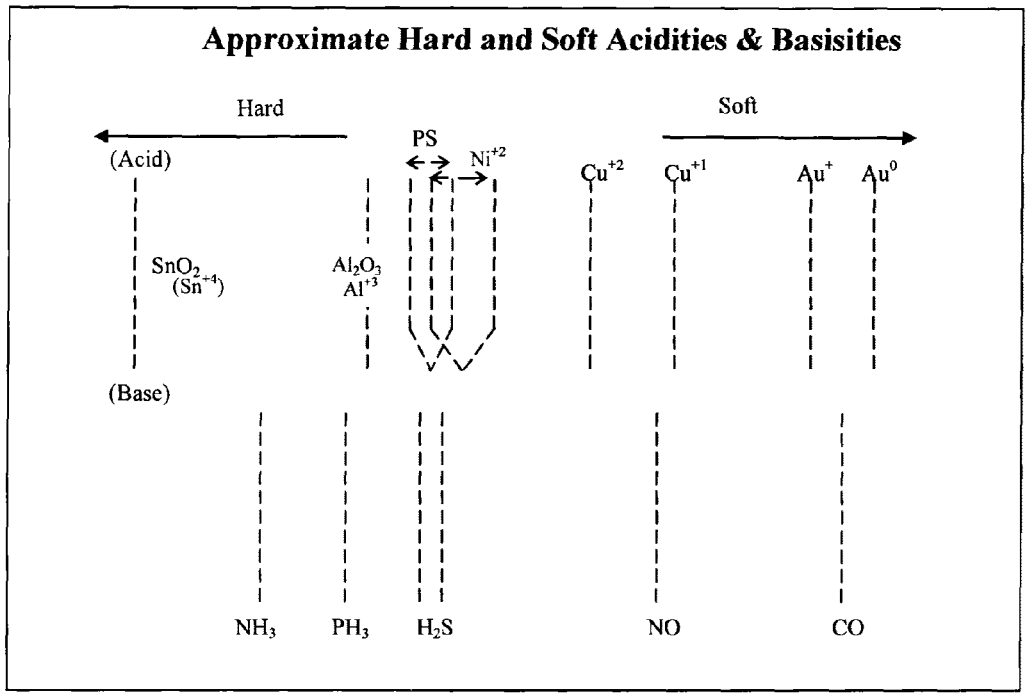
FIG. 2.6

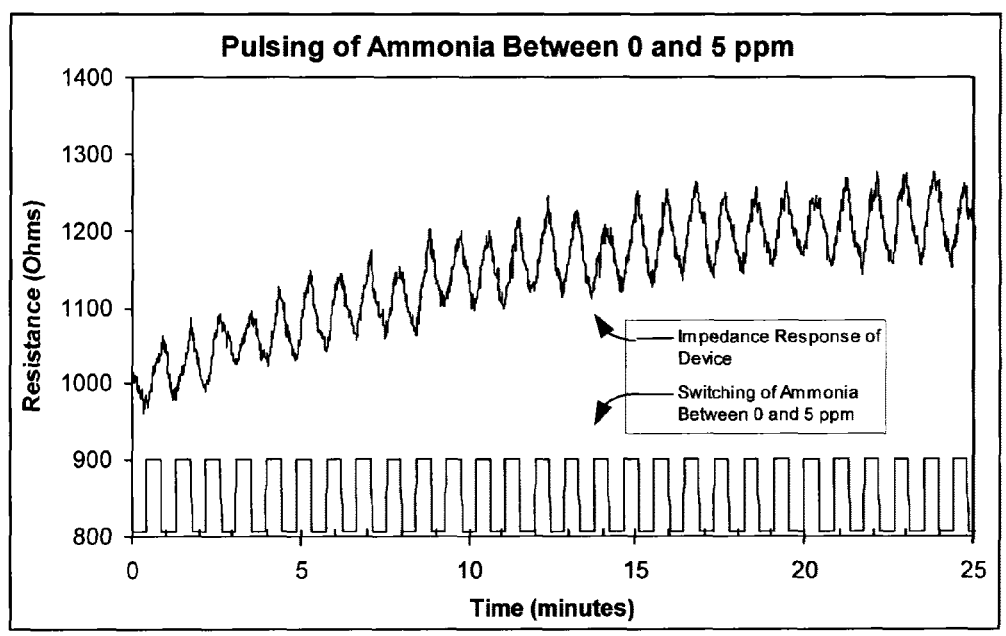
FIG. 3.1

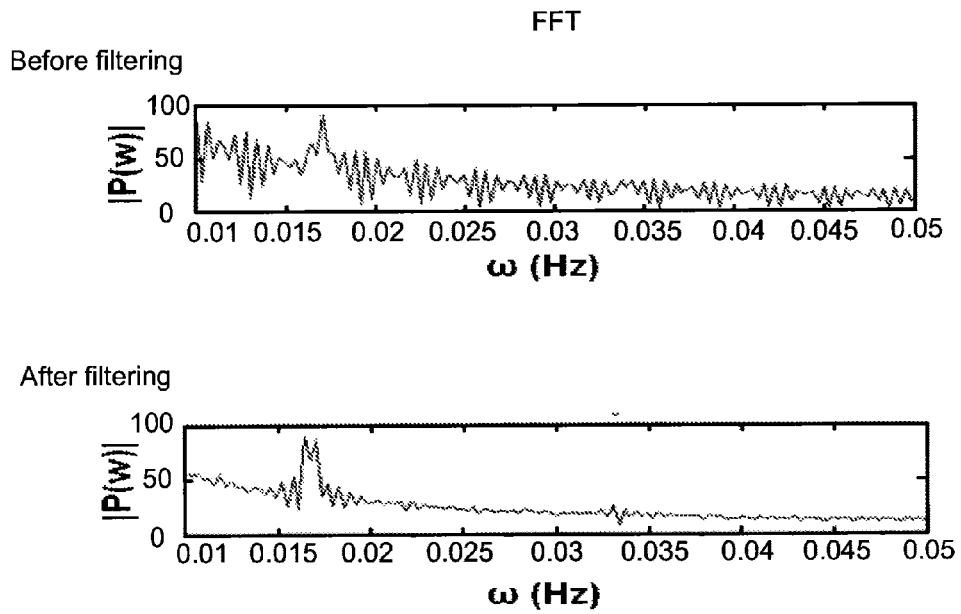
FIG. 3.2
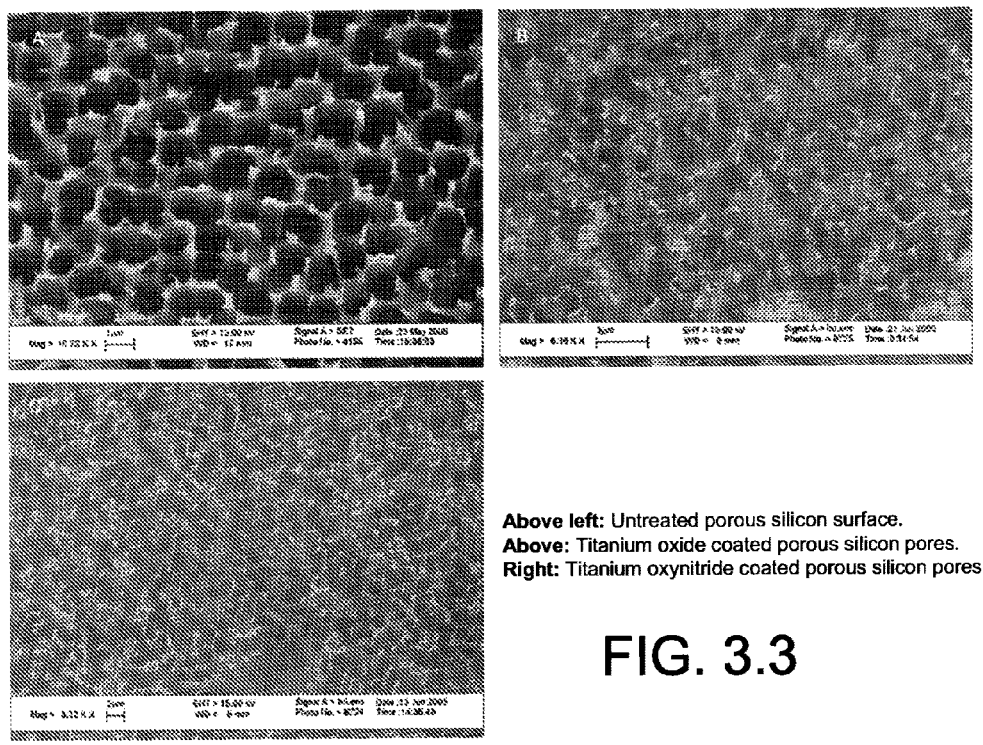
Above left: Untreated porous silicon surface.
Above: Titanium oxide coated porous silicon pores.
Right: Titanium oxynitride coated porous silicon pores.
FIG. 3.3

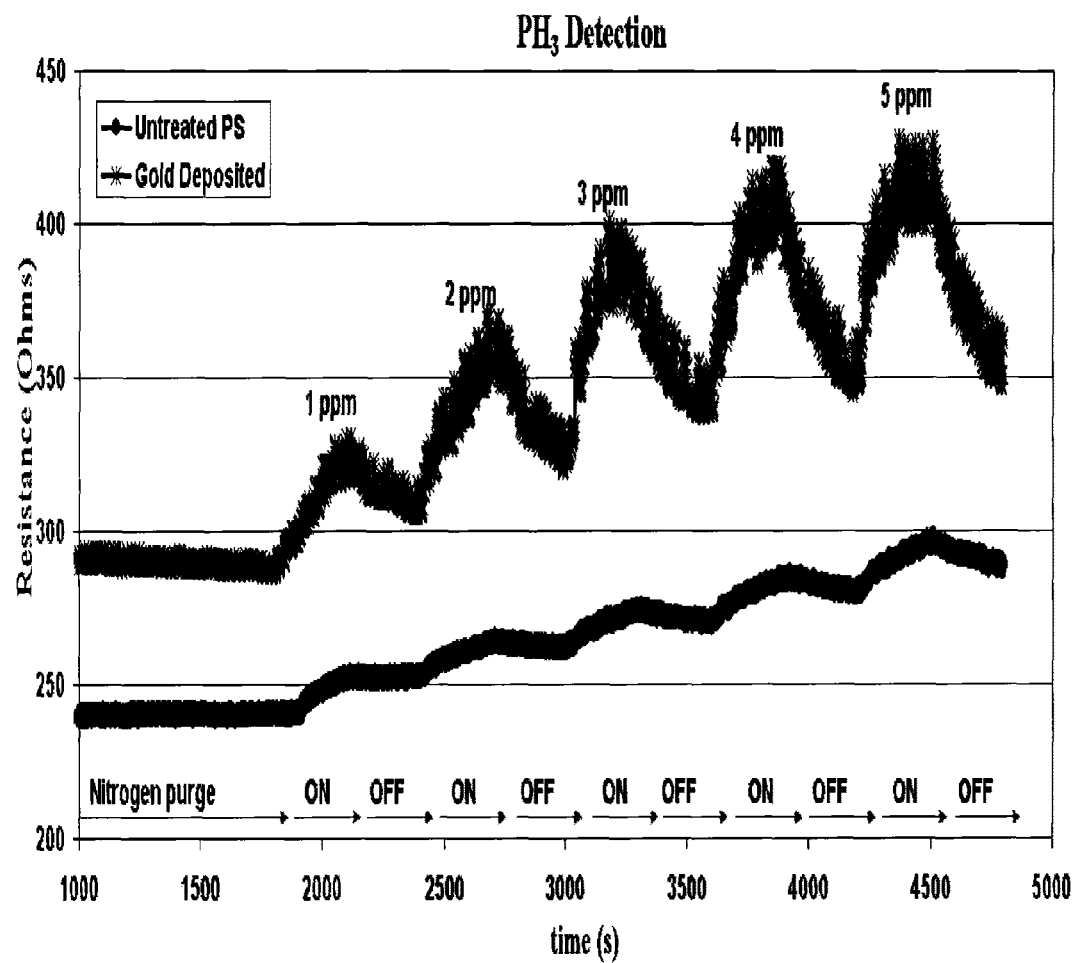
FIG. 4.1

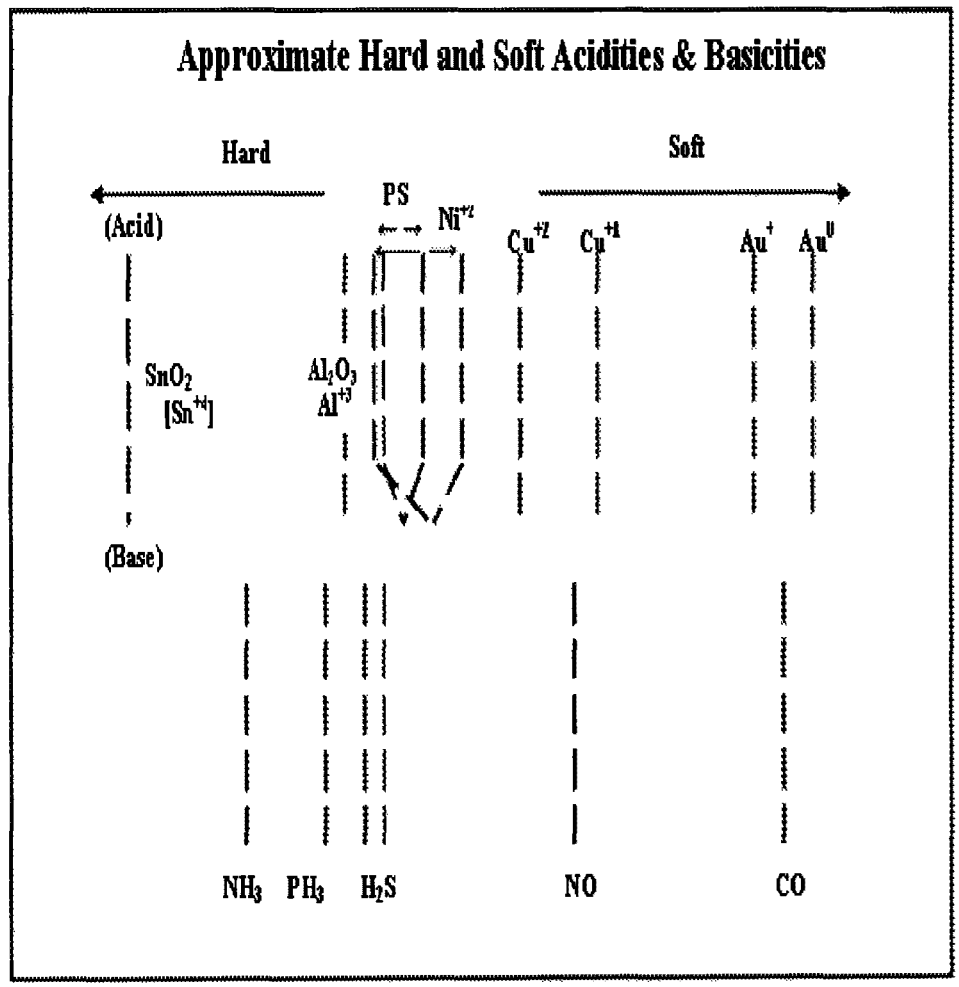
FIG. 4.2

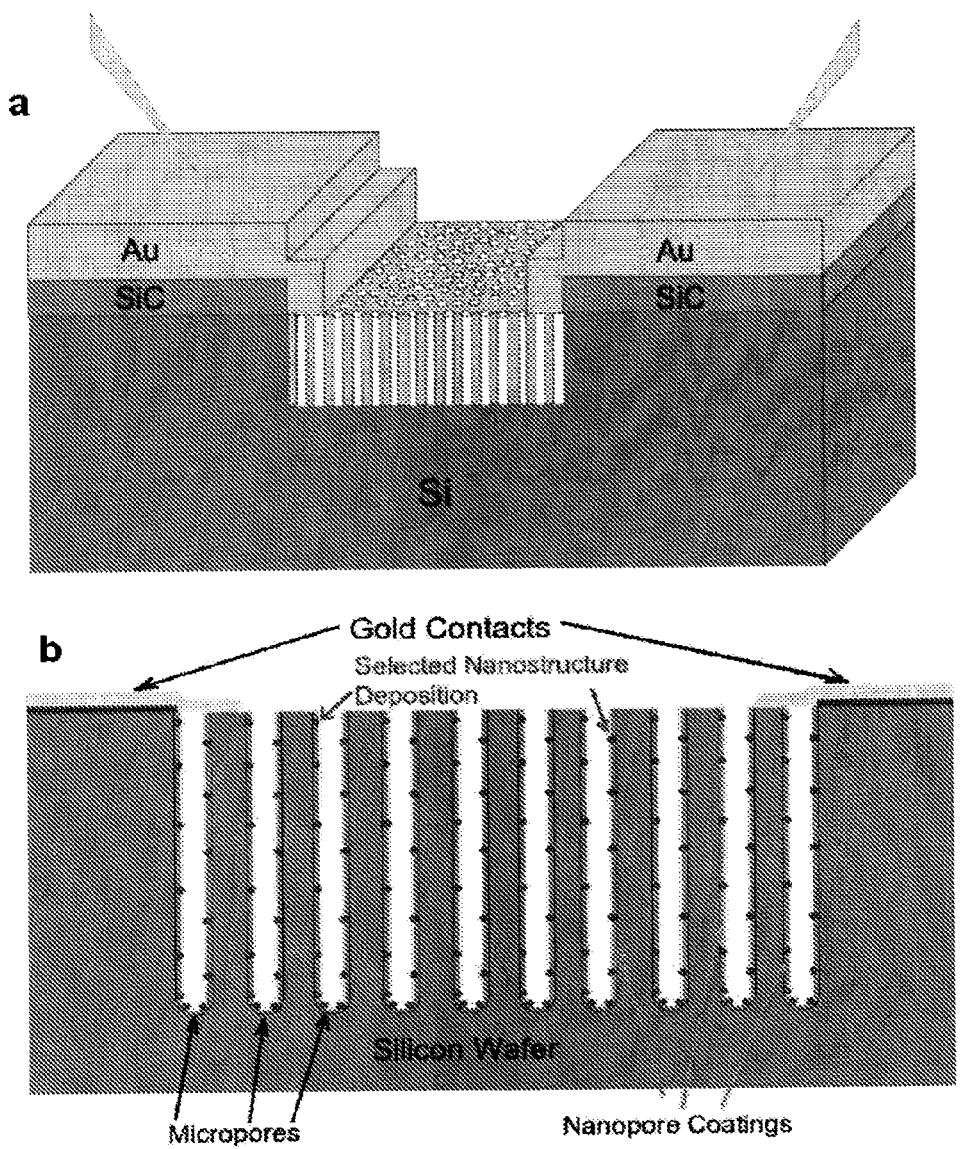
FIG. 4.3

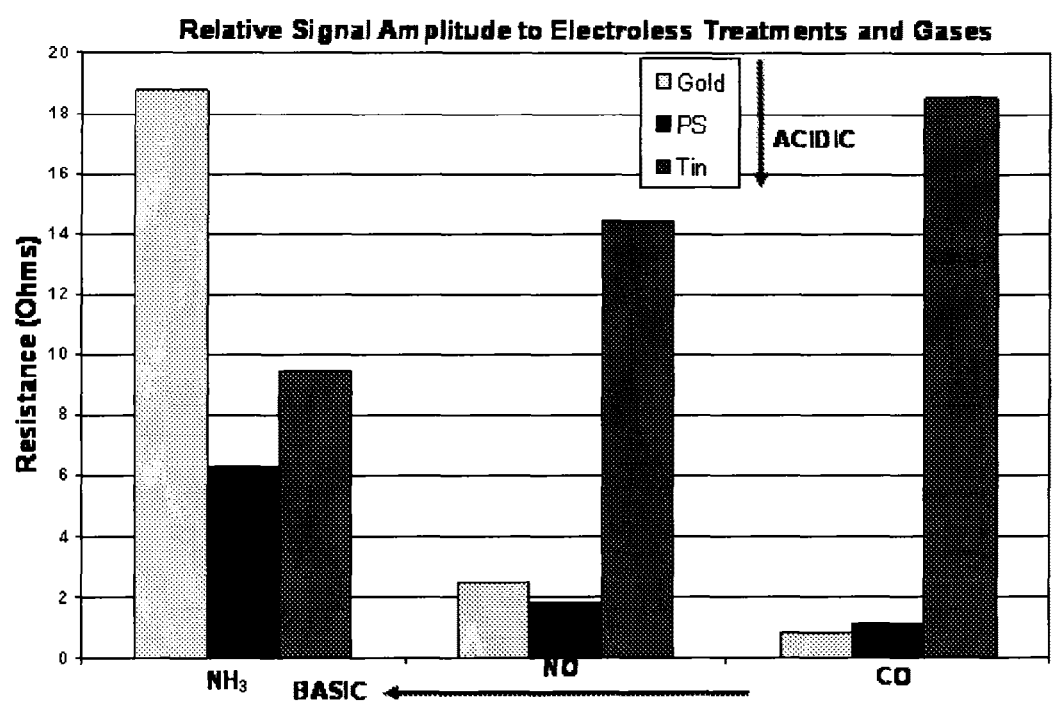
FIG. 4.4

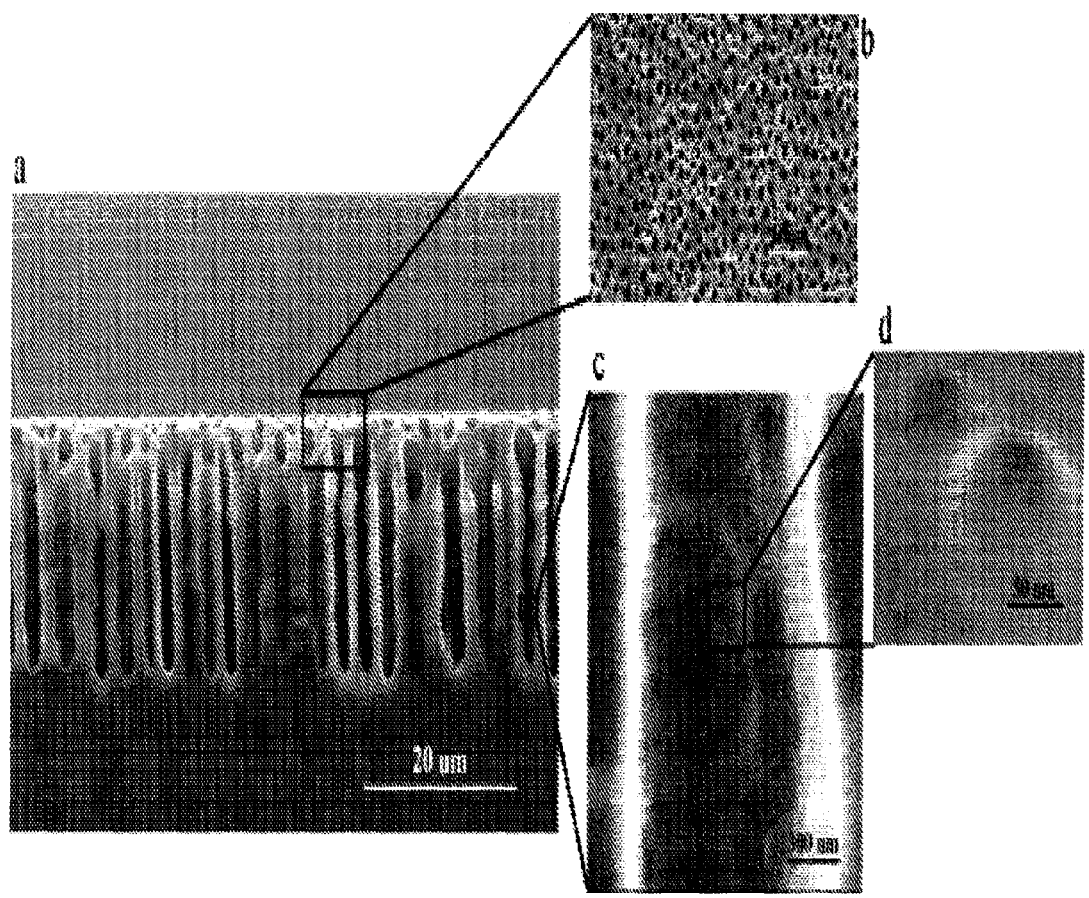
FIG. 5.1

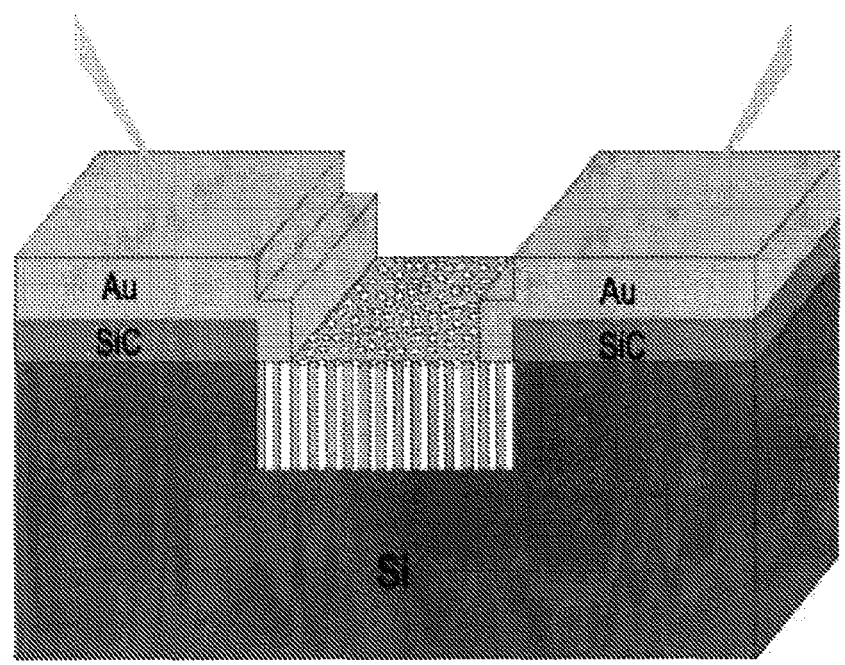
FIG. 5.2
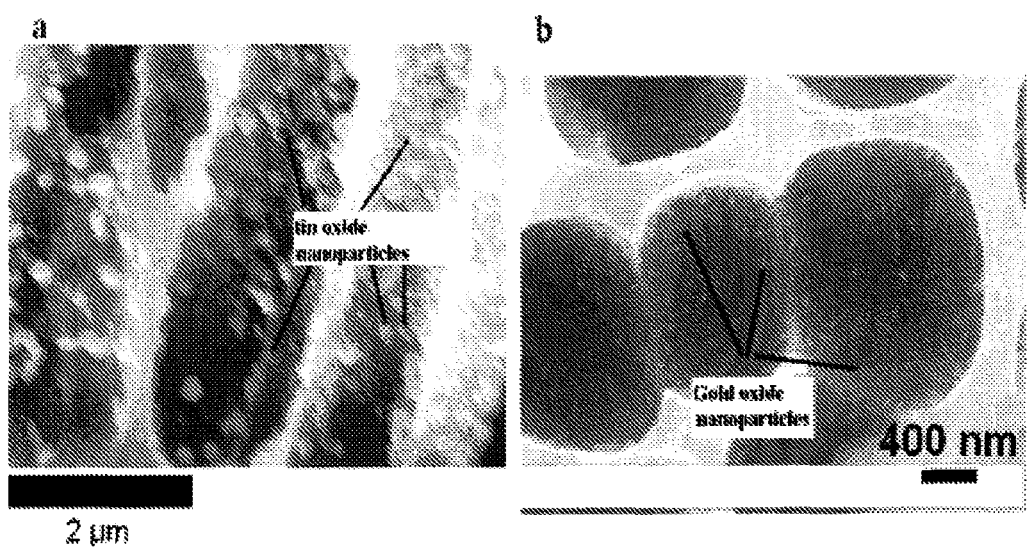
FIG. 5.3

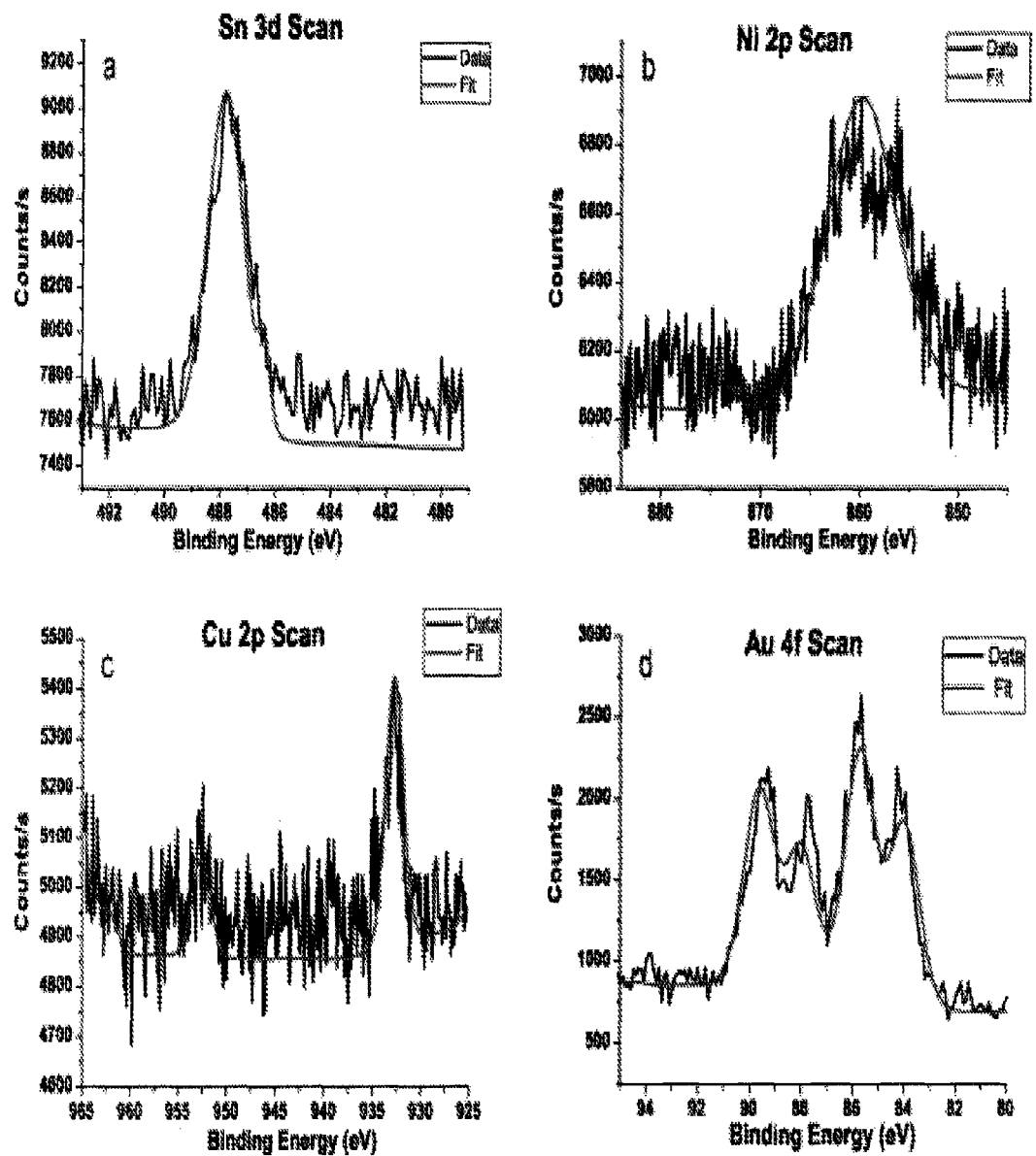
FIG. 5.4

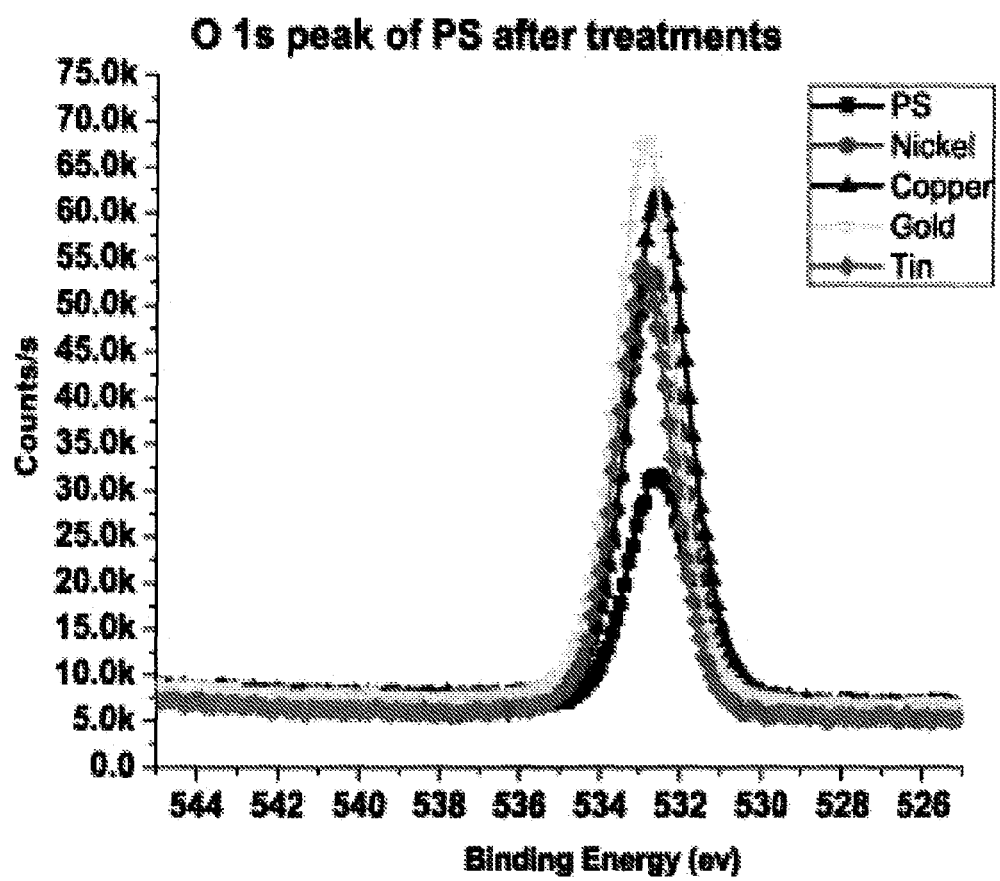
FIG. 5.5

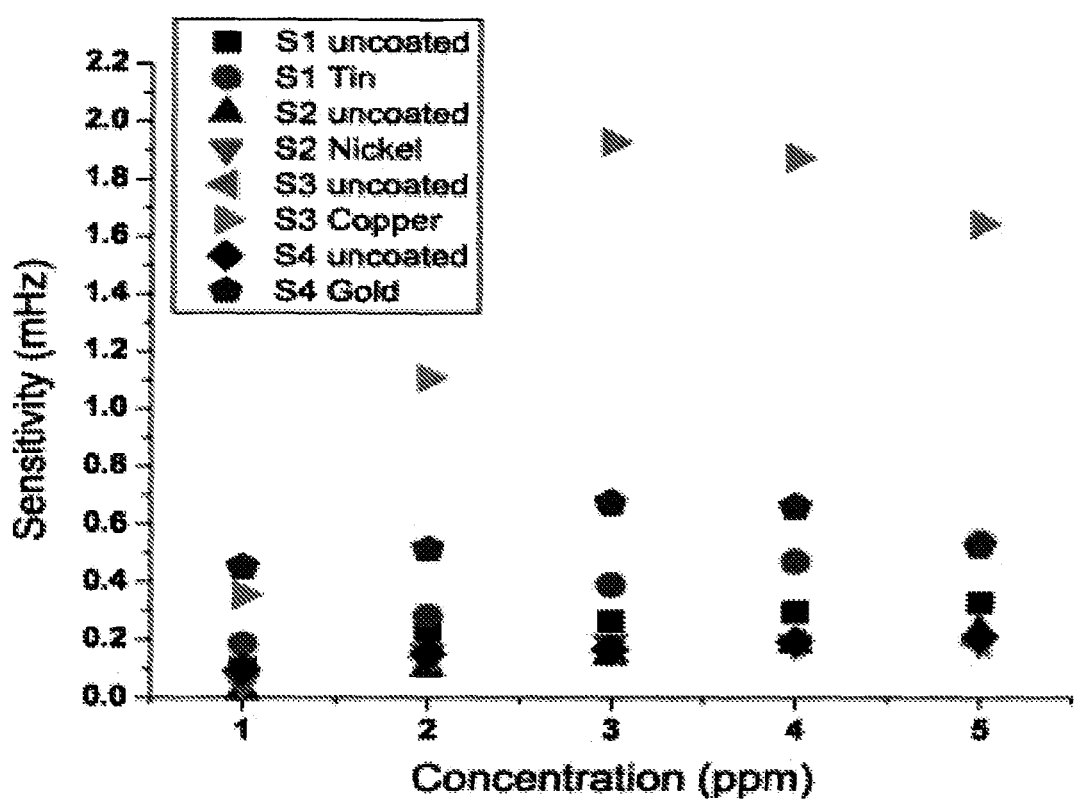
FIG. 5.6

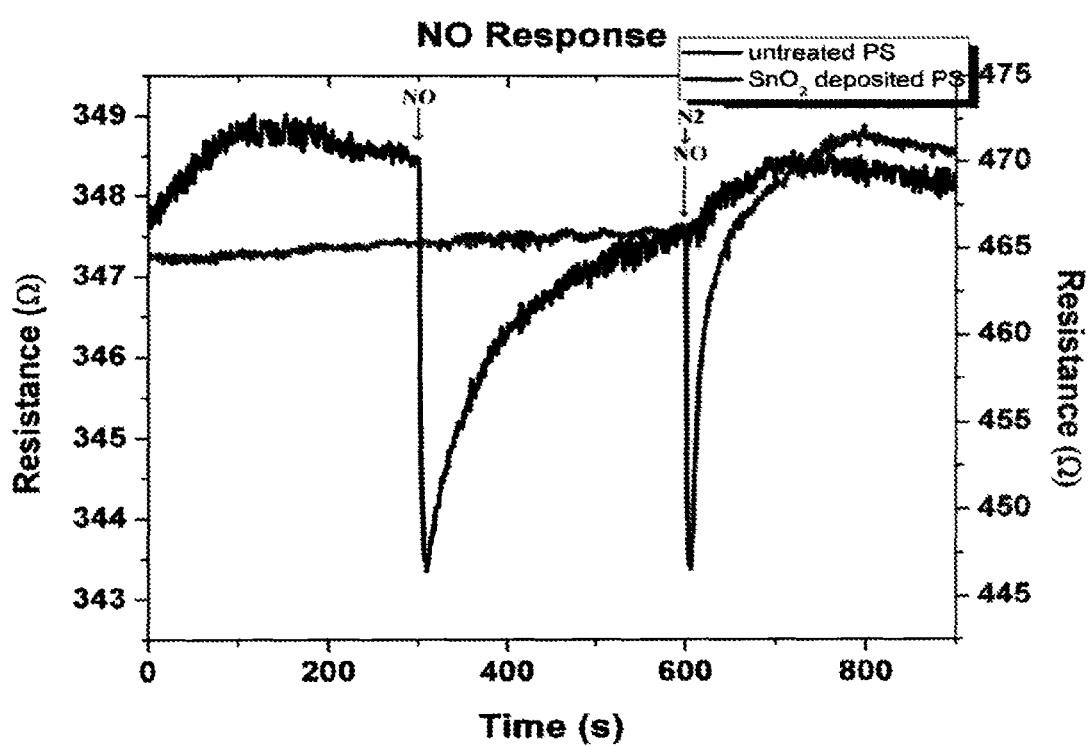
FIG. 5.7

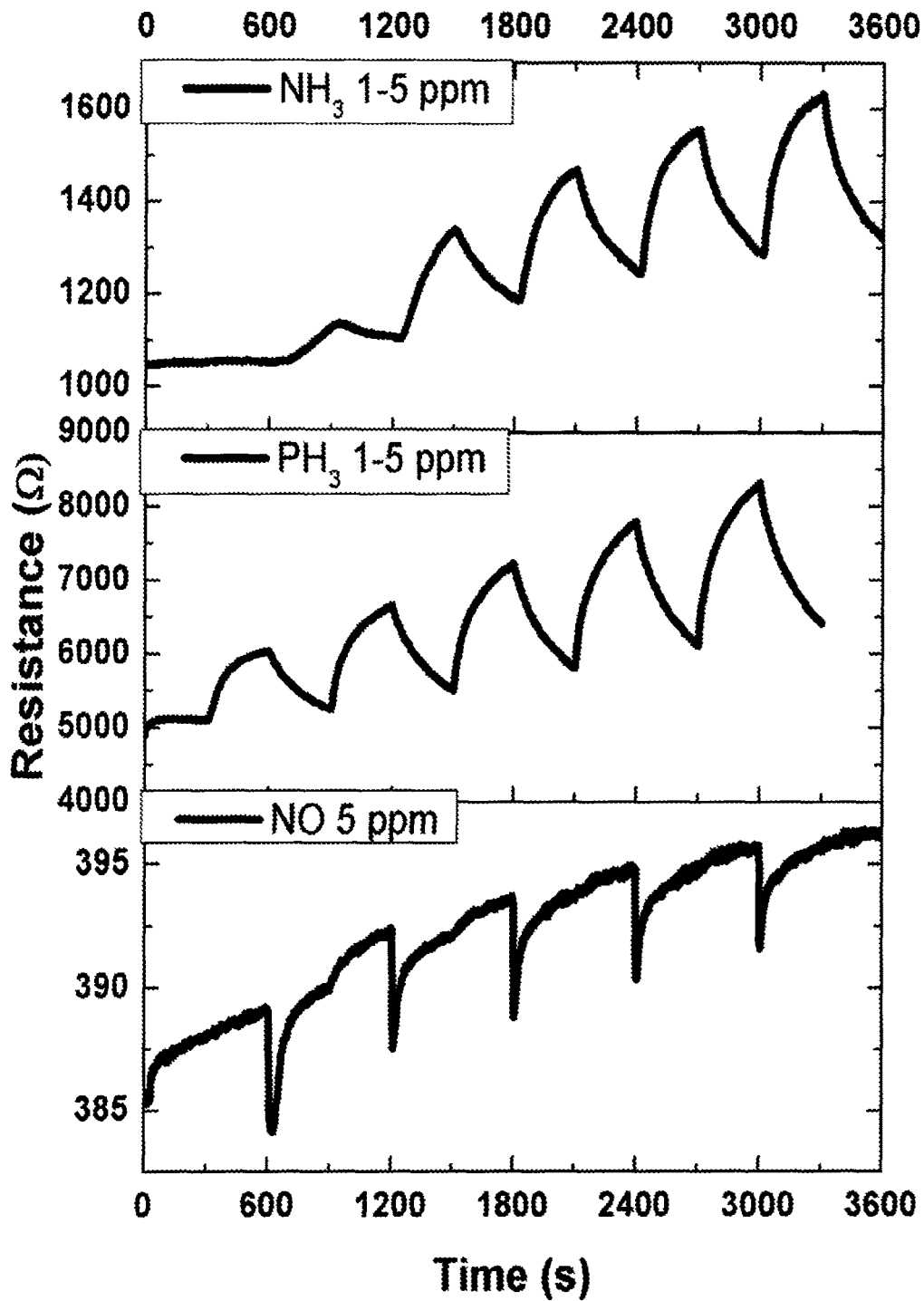
FIG. 5.8

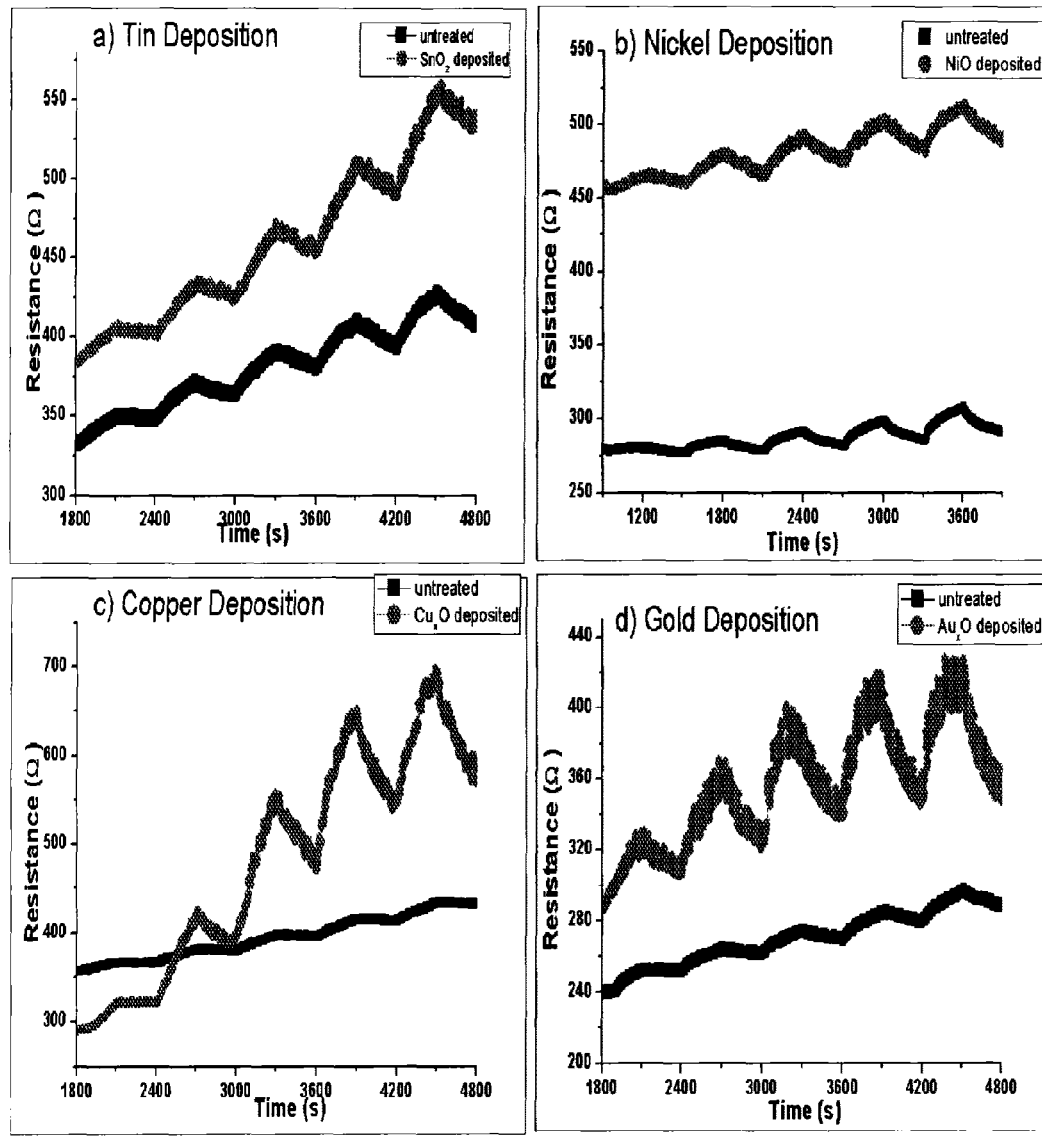
FIG. 5.9

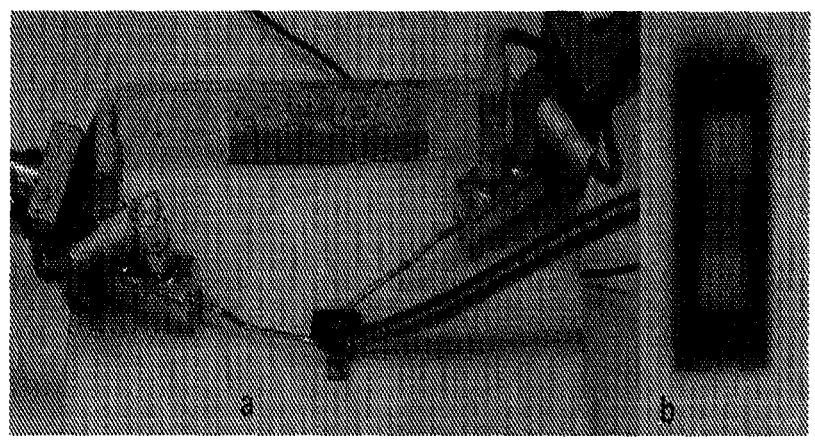
FIG. 5.10

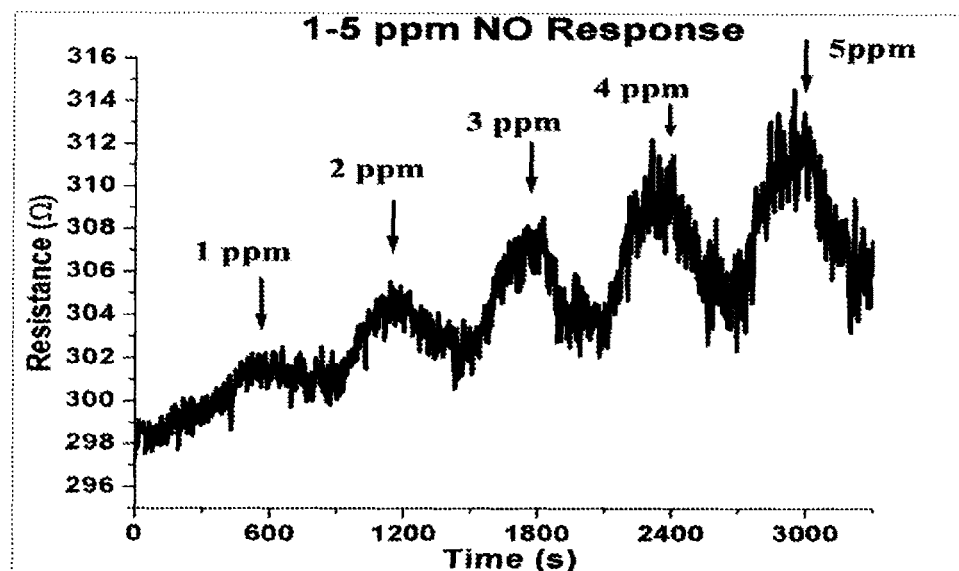
FIG. 6.1
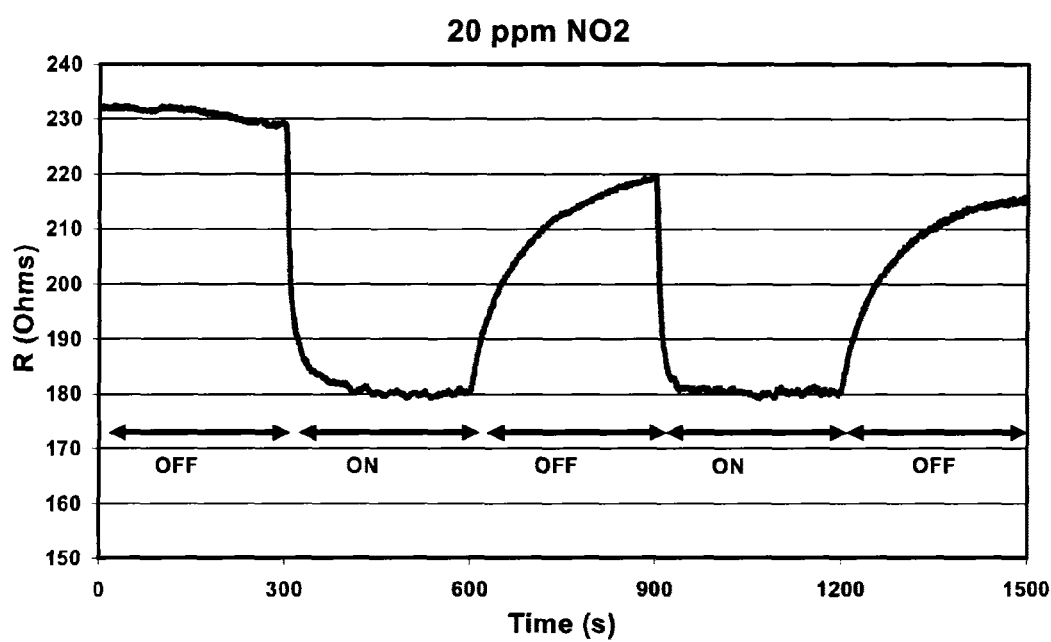
FIG. 6.2

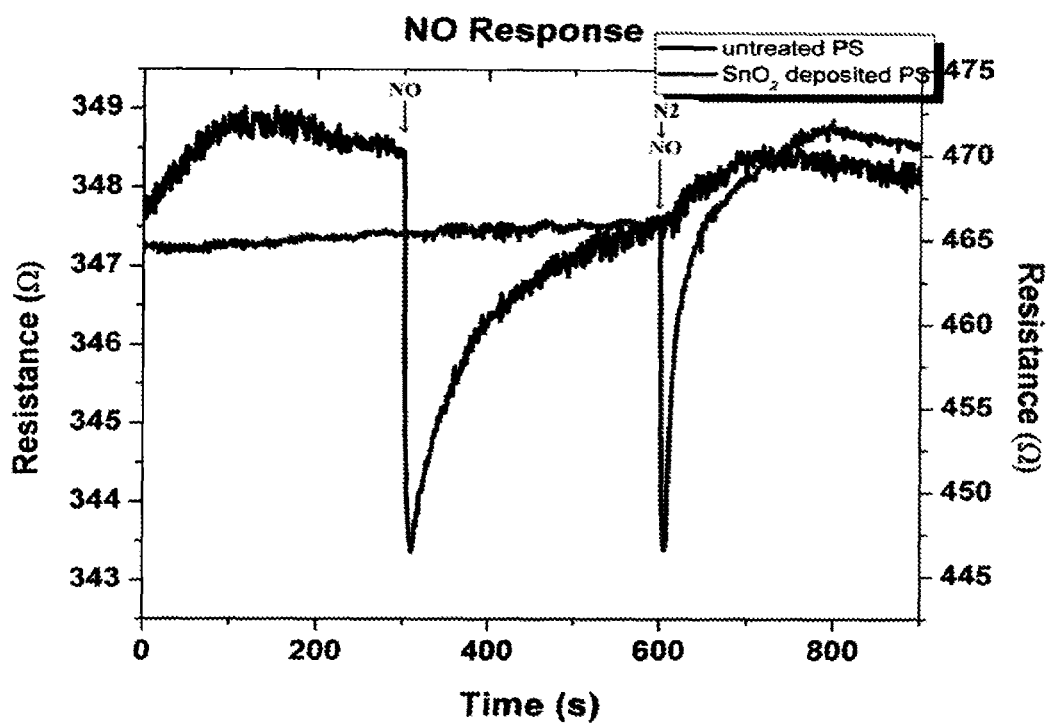
FIG. 6.3A
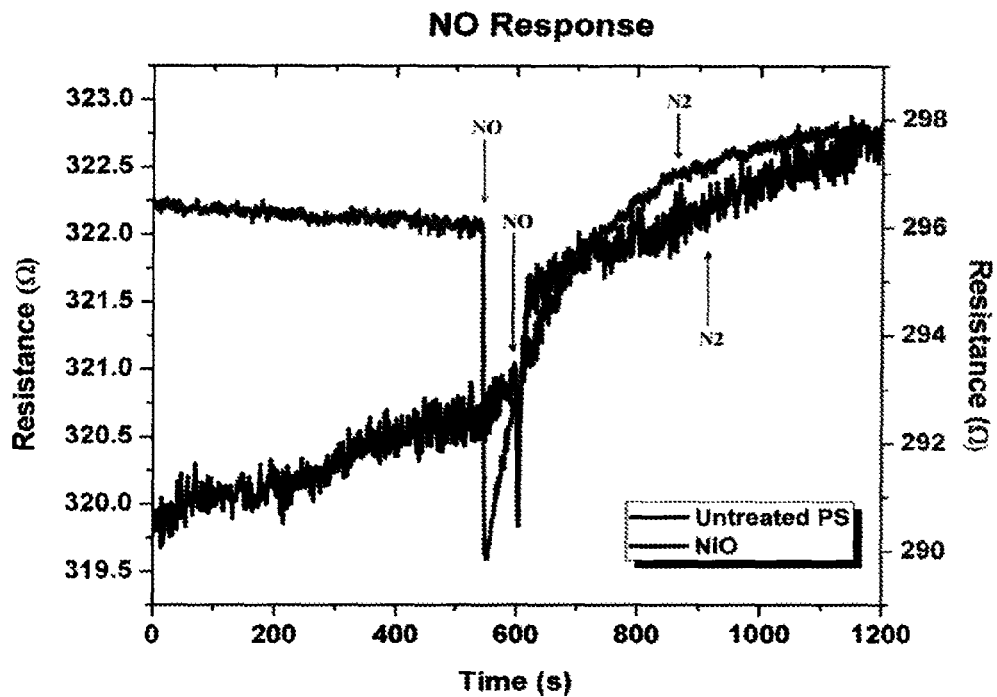
FIG. 6.3B

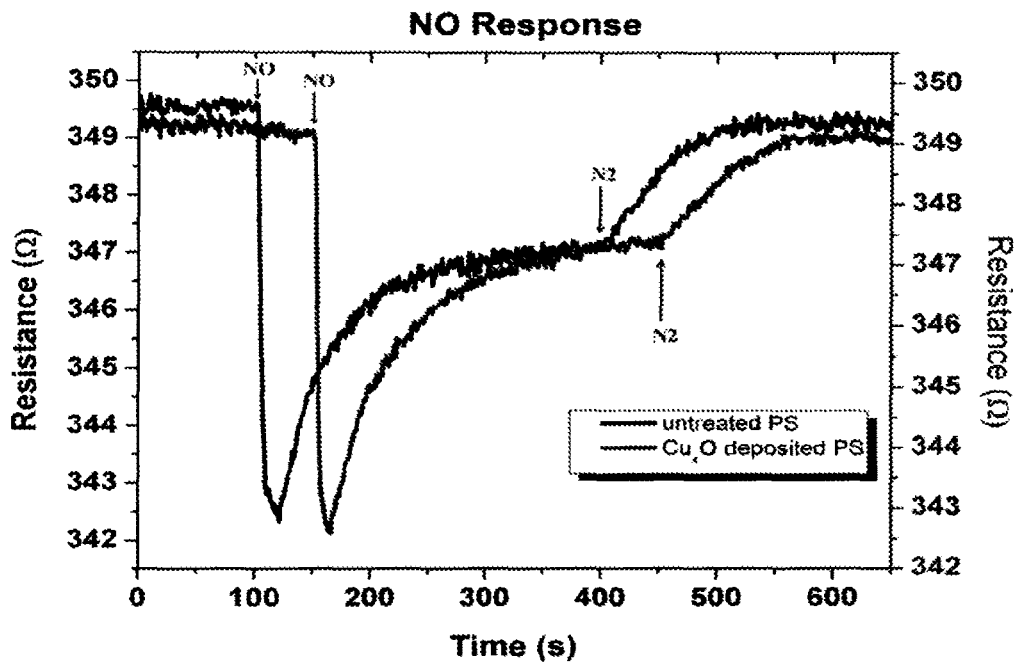
FIG. 6.3C
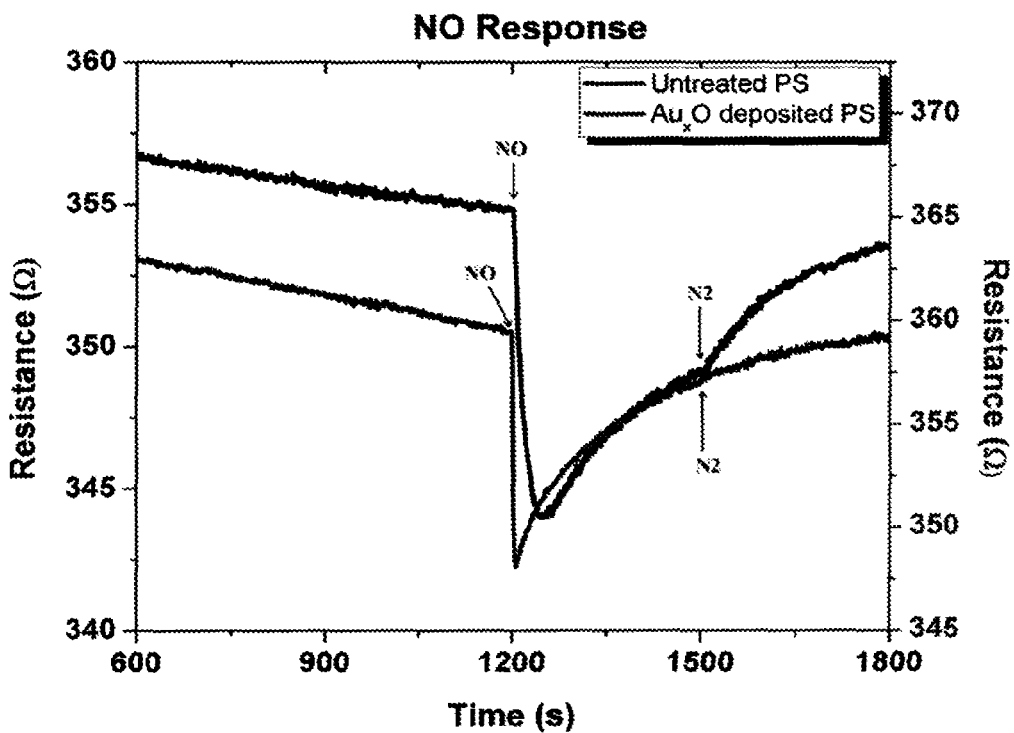
FIG. 6.3D

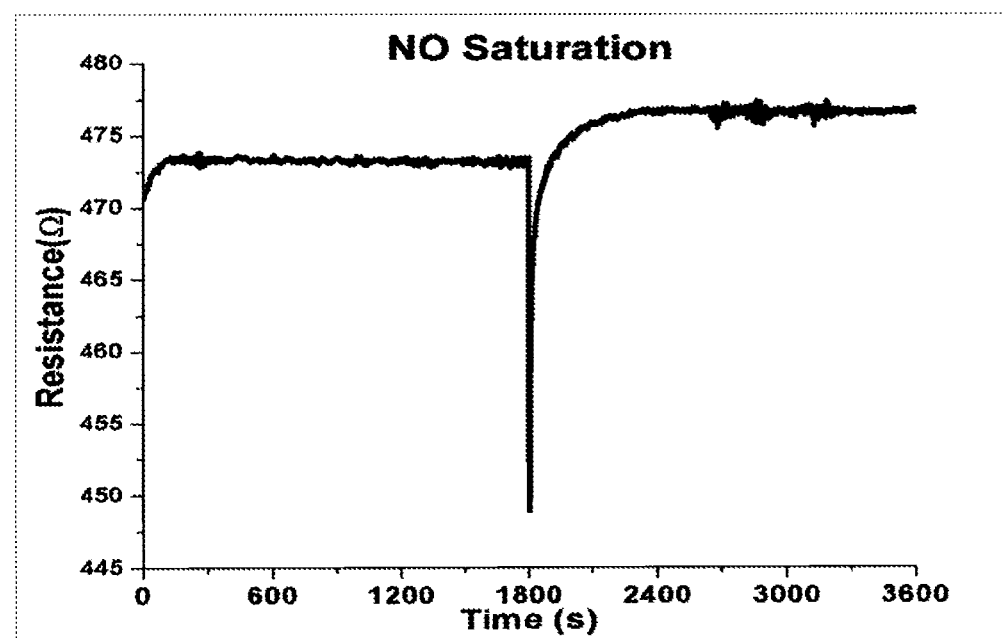
FIG. 6.3E
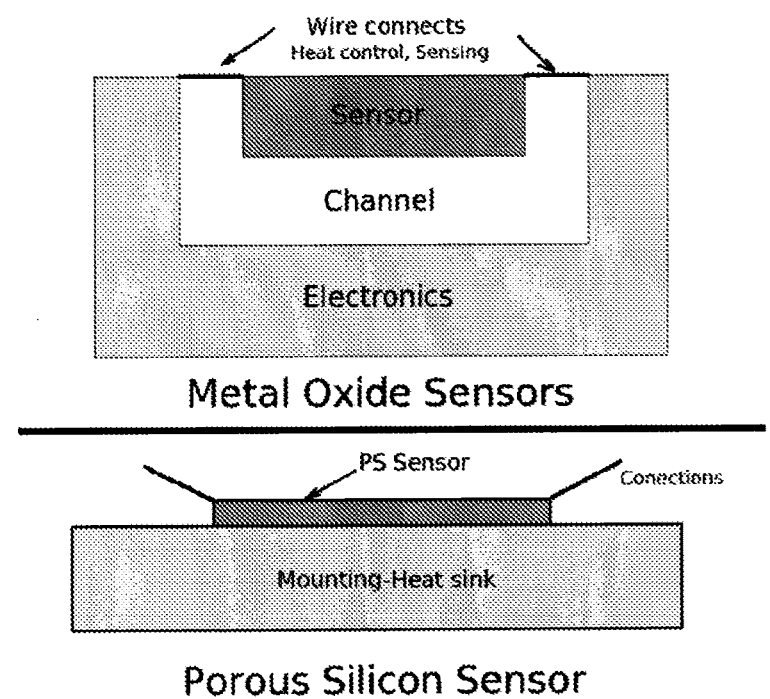
FIG. 6.4

GAS SENSORS, METHODS OF PREPARATION THEREOF, METHODS OF SELECTING GAS SENSOR MATERIALS, AND METHODS OF USE OF GAS SENSORS

CROSS-REFERENCE TO RELATED APPLICATION

This application is a continuation in-part application of PCT patent application PCT/US2009/054596 (WO 2010/022321) filed on Aug. 21, 2009, entitled "GAS SENSORS, METHODS OF PREPARATION THEREOF, METHODS OF SELECTING GAS SENSOR MATERIALS, AND METHODS OF USE OF GAS SENSORS", and claims priority to the PCT, where the PCT claims priority to copending U.S. Provisional Application entitled "GENERAL APPROACH TO CREATING SELECTIVE METAL COATINGS AT A NANO/MICROPOROUS POROUS SILICON INTERFACE FOR SENSOR APPLICATIONS" having Ser. No. 61/090,682, filed on Aug. 21, 2008, which is incorporated herein by reference.

FEDERAL SPONSORSHIP

This invention was made with Government support under Contract/Grant No. CTS 0608896, awarded by the National Science Foundation. The Government has certain rights in this invention.

BACKGROUND

Porous silicon (PS) has drawn considerable attention for sensor applications. Its luminescence properties, large surface area, and compatibility with silicon based technologies have been the driving force for this technology development. However, there exists a need in the industry to advance sensor technologies and the selection of sensors for specific gas(es).

SUMMARY

Embodiments of the present disclosure provide for methods of selecting a nanostructured deposit for a conductometric gas sensor, methods of detecting a gas based on the acidic or basic characteristic of the gas using a conductometric gas sensor, devices including conductometric gas sensors, arrays of conductometric gas sensors, methods of determining the acidic or basic characteristic of a gas, methods of treating a sensor, and the like.

One exemplary method of selecting a nanostructured deposit for a conductometric porous silicon gas sensor, among others, includes: exposing a gas to a plurality of testing conductometric porous silicon gas sensors, wherein each of the testing conductometric porous silicon gas sensors is operative to transduce the presence of a gas into an impedance change, wherein the impedance change correlates to the gas concentration, wherein the testing conductometric porous silicon gas sensor has a porous silicon layer, wherein one or more of the testing conductometric porous silicon gas sensors has a nanostructured deposit disposed on the porous silicon layer, wherein the nanostructured deposit is selected from the group consisting of: a nanostructured deposit having the characteristic of a hard acid, a nanostructured deposit having the characteristic of a intermediate acid, a nanostructured deposit having the characteristic of a soft acid, a nanostructured deposit having the characteristic of a hard base, a nanostructured deposit having the characteristic of a intermediate base, and a nanostructured deposit having the characteristic of a soft base, measuring an impedance change using each of the testing conductometric porous silicon gas sensors relative to a standard testing conductometric porous silicon gas sensor, and selecting the nanostructured deposit using the concept that the nanostructured deposit and the gas have complementary characteristics based on the interactions of two of the following: a hard acid, an intermediate acid, a soft acid, a hard base, an intermediate base, and a soft base, where such interaction between the gas and the nanostructured deposit determines the measured impedance change, wherein the combination of the nanostructured deposit and the gas generates a range of impedance changes, the greatest impedance change being determined by the maximum hard acid/soft base or hard base/soft acid mismatch between the gas and the nanostructured deposit.

One exemplary method of detecting a gas based on the acidic or basic characteristic of the gas using a conductometric porous silicon gas sensor, among others, includes: exposing a gas to one or more conductometric porous silicon gas sensors, wherein each of the conductometric porous silicon gas sensors is operative to transduce the presence of a gas into an impedance change, wherein the impedance change correlates to the gas concentration, wherein the conductometric porous silicon gas sensor has a porous silicon layer, wherein one or more of the conductometric porous silicon gas sensors has a nanostructured deposit disposed on the porous silicon layer, wherein the nanostructured deposit is selected from the group consisting of: a nanostructured deposit having the characteristic of a hard acid, a nanostructured deposit having the characteristic of a intermediate acid, a nanostructured deposit having the characteristic of a soft acid, a nanostructured deposit having the characteristic of a hard base, a nanostructured deposit having the characteristic of a intermediate base, and a nanostructured deposit having the characteristic of a soft base, wherein the nanostructured deposit used is based on the concept that the nanostructured deposit and the gas have complementary characteristics based on the interactions of two of the following: a hard acid, an intermediate acid, a soft acid, a hard base, an intermediate base, and a soft base, where such interaction between the gas and the nanostructured deposit determines the measured impedance change, wherein the greatest impedance change is obtained by using a nanostructured deposit and the gas promoting an interaction that generates the maximum acid-base mismatch; measuring the impedance change using one or more of the conductometric porous silicon gas sensors relative to a standard conductometric porous silicon gas sensor; and obtaining the greatest impedance change using the conductometric porous silicon gas sensor that has the nanoparticle deposit that interact with the gas to produce the maximum acid-base mismatch.

One exemplary device, among others, includes: a conductometric porous silicon gas sensor including a silicon substrate having a porous silicon layer, wherein a nanostructured deposit is disposed on a portion of the porous silicon layer, wherein the conductometric porous silicon gas sensor is operative to transduce the presence of a gas into an impedance change, wherein the impedance change correlates to the gas concentration, wherein if the gas of interest has the characteristic of a hard base, the nanostructured deposit does not have the characteristics of a hard acid, wherein if the gas of interest has the characteristic of a soft base, the nanostructured deposit does not have the characteristics of a soft acid, wherein if the gas of interest has the characteristic of an intermediate base, the nanostructured deposit does not have the characteristic of an intermediate acid, wherein if the gas of interest has the characteristic of a hard acid, the nanostructured deposit does not have the characteristics of a hard base, wherein if the gas of interest has the characteristic of a soft acid, the nanostructured deposit does not have the characteristic of a soft base, wherein if the gas of interest has the characteristic of an intermediate acid, the nanostructured deposit does not have the characteristic of an intermediate base.

One exemplary method of determining the acidic or basic characteristic of a gas, among others, includes: exposing a gas to a plurality of conductometric porous silicon gas sensors, wherein each of the conductometric porous silicon gas sensors is operative to transduce the presence of a gas into an impedance change, wherein the impedance change correlates to the gas concentration, wherein the conductometric porous silicon gas sensor has a porous silicon layer, wherein one or more of the conductometric porous silicon gas sensors has a nanostructured deposit disposed on the porous silicon layer, wherein the nanostructured deposit is selected from the group consisting of: a nanostructured deposit having the characteristic of a hard acid, a nanostructured deposit having the characteristic of a intermediate acid, a nanostructured deposit having the characteristic of a soft acid, a nanostructured deposit having the characteristic of a hard base, a nanostructured deposit having the characteristic of a intermediate base, and a nanostructured deposit having the characteristic of a soft base, wherein the nanostructured deposit used is based on the concept that the nanostructured deposit and the gas have complementary characteristics based on the interactions of two of the following: a hard acid, an intermediate acid, a soft acid, a hard base, an intermediate base, and a soft base, where such interaction between the gas and the nanostructured deposit determines the measured impedance change, measuring an impedance change using each of the conductometric porous silicon gas sensors relative to a standard conductometric porous silicon gas sensor, and determining if the gas has the characteristic of a hard acid, an intermediate acid, a soft acid, a hard base, an intermediate base, or a soft base, based on the impedance change of the conductometric porous silicon gas sensors.

One exemplary method of treating a porous silicon sensor, among others, includes: providing a porous silicon sensor having a porous silicon layer, wherein the porous silicon layer is contaminated so that the response of the porous silicon sensor is significantly reduced; and exposing the porous silicon layer to a rejuvenating solution, wherein after exposure to the rejuvenating solution the response of the porous silicon sensor is substantially the response of the porous silicon sensor prior to use.

Other systems, methods, features, and advantages of the present disclosure will be or become apparent to one with skill in the art upon examination of the following detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1.1A and 1.1B illustrate cross-section views of two embodiments of conductometric porous silicon (PS) gas sensors.

FIG. 1.2A-1.2I illustrate cross-section views of the conductometric PS gas sensors shown in FIG. 1.1B during a representative fabrication process.

FIG. 2.1(a) illustrates a digital image of a close up side view of a hybrid porous silicon film. FIG. 2.1(b) illustrates a digital image of a nanoparticle tin-oxide coating dispersed on the porous silicon micro/nanopores. FIG. 2.1(c) illustrates a digital image of 10 to 30 nm $Au_xO$ nanostructure dispersed on the porous silicon micro/nanoporous surface.

FIG. 2.2 illustrates a comparison of the response measured initially for sensors that are untreated, treated with electroless gold, or treated with electroless tin, and tested with 30 repeat pulses of 20 ppm $NO_x$, $NH_3$, or CO. The average impedance change is given in FIG. 2.2.

FIG. 2.3 illustrates the significantly improved sensitivity to ammonia vs. the average impedance changes given in FIG. 2.2.

FIG. 2.4 illustrates the improved $PH_3$ response to an electroless $Au_xO$ coating.

FIG. 2.5 illustrates the response to $NH_3$ after a sensor is subjected to a rejuvenation process.

FIG. 2.6 illustrates the estimated hard and soft acidities and basicities based on resistance changes relative to porous silicon.

FIG. 3.1 illustrates a gas sensor response to pulsing of ammonia between 0 and 5 ppm (in research grade nitrogen).

FIG. 3.2 illustrates a Fast Fourier Transform of PS gas response (FIG. 3.2(a)) before filtering and (FIG. 3.2(b)) after filtering.

FIG. 3.3a illustrates a digital image of a close up top view of a hybrid porous silicon films. FIG. 3.3b illustrates a digital image of 100-200 nm $TiO_2$ nanoparticles coating the porous silicon micropores. FIG. 3.3c illustrates a digital image of 10 nm $TiO_{2-x}N_x$ nanoparticles coating (60%) the porous silicon micropores.

FIG. 4.1 illustrates the improved $PH_3$ response to an electroless $Au_xO$ deposit. Here, 1, 2, 3, 4, and 5 ppm of $PH_3$ is pulsed onto the sensor surface every 300 s. For the first 1800 s an $N_2$ purge is applied for resistance stabilization.[25]

FIG. 4.2 illustrates the estimated hard and soft acidities and basicities based on resistance changes relative to porous silicon.

FIG. 4.3A illustrates a schematic diagram of the conductometric PS gas sensor.

FIG. 4.3B illustrates a schematic diagram of a hybrid etched nanopore covered microporous array coated with selected nanostructures on a c-Si wafer. Gold contacts are deposited onto the PS via a SiC insulation layer on the c-Si.

FIG. 4.4 illustrates a comparison of responses for sensors consisting of an untreated PS interface with those treated with gold or tin to form $SnO_x$ (x=1, 2) and gold clustered oxide $Au_xO$ nanostructured island deposits (FIG. 2.1). Note that the three bases, $NH_3$, NO, and CO introduced to the treated "p-type" silicon result in a positive resistance change and that the relative responses the strong (hard) base $NH_3$ and the weak (soft) bases NO and CO are distinct. The significant differences in relative response are maintained with improved interfaces whose S/N is up to two orders of magnitude greater (See FIG. 4.3).

FIG. 5.1A illustrates a side view and FIG. 5.1B illustrates a top view of micropore structure, FIG. 5.1C illustrates a micropore side view, and FIG. 5.1D illustrates a nanopore SEM image of a porous silicon etch within the silicon micropore.

FIG. 5.2 illustrates a porous Si gas sensor schematic. The resistance change is measured via precision microprobes when the porous silicon interface is exposed to a test gas. A SiC layer also serves as an insulation layer as the resistance response of the porous layer is measured through gold contacts.

FIG. 5.3A illustrates tin oxide nanoparticles deposited onto PS. FIG. 5.3B illustrates gold oxide nanoparticles deposited onto PS.

FIG. 5.4 illustrates XPS spectra for metal-oxide nanostructures deposited PS sensors and fitting curves (in red) to the spectra. FIG. 5.4A illustrates a XPS spectrum of a dominantly $SnO_x$ deposited sensor. SnO ($Sn^{2+}$) has peaks in the range of 485.6-487.0 eV, $SnO_2$ ($Sn^{4+}$) has peaks in the range of 486.1-487.1 eV. FIG. 5.4B illustrates a XPS spectrum of a dominantly $NiO_x$ deposited sensor. Nickel has an oxidation peak ($2p_{1/2}$) located ~871.8 eV for NiO ($Ni^{2+}$) and has peaks ($2p_{3/2}$) in the range of 853.6-857.2 eV. $Ni_2O_3$ ($Ni^{3+}$) shows peaks from 855.8 eV to 856.5 eV. FIG. 5.4C illustrates a XPS spectrum for a dominantly $Cu_xO$ deposited PS surface. CuO ($Cu^{2+}$) has peaks ($2p_{1/2}$) in the range of 952.5-952.7 eV and has peaks ($2p_{3/2}$) in the range of 933.3-934.3 eV. $Cu_2O$ ($Cu^{1+}$) has peaks in the range of 932.0-932.8 eV. FIG. 5.4D illustrates a XPS spectrum for Au $4f_{5/2}$ and Au $4f_{7/2}$ doublets which demonstrate minimal oxidation.

FIG. 5.5 illustrates O 1 s spectra of untreated and nanoparticle treated PS surfaces.

FIG. 5.6 illustrates the response change to $PH_3$ for metal oxides deposits formed with electroless metal treatments.

FIG. 5.7 illustrates the 1 ppm response for untreated (upper curve on left, first NO spike) and $SnO_2$ nanostructure treated PS (lower curve, spike around 600) to NO. The first region corresponds to an $N_2$ purge for base resistance stabilization until NO is introduced. Initially a transient $NO_2$ signal is observed. After 300 s of exposure, NO is turned off and the surface is purged with $N_2$. Note the scales to left (PS) and right (treated PS).

FIG. 5.8A illustrates the sensitivity test for 1, 2, 3, 4, 5 ppm $NH_3$, FIG. 5.8B) 1-5 ppm $PH_3$, and FIG. 5.8C) 5 ppm NO. The first region (600 s in the $NH_3$ and NO response and 300 s in the $PH_3$ response) corresponds to the $N_2$ purge of the sensor (in an open configuration) to condition the sensor, remove residual water, and obtain the optimal return to baseline for the open configuration used in these experiments. The sensor is exposed to the test gas for 300 s followed by a cut-off for the next 300 s. This cycle is run for 1 hr. The nanostructure deposition on the PS surface is tin oxide. Additional details are described in Example 5.

FIG. 5.9 illustrates a comparison of responses for $PH_3$[12] sensors with an untreated "p-type" PS interface to interfaces treated with $SnO_x$, NiO, $Cu_xO$, and gold clustered oxide, $Au_xO$ nanostructures. Nanostructured islands produced from the exemplar oxides (or of these exemplar oxides) greatly enhance sensitivity, as they produce a significant variation in response within themselves and up the untreated PS interface. The matrix of sensitivities relative to the untreated interface indicated in Table 1 in Example 4 corresponds to an increasing resistance due to the "p-type" PS interface. The drift in baseline, caused primarily by the open configuration used to make the measurements on a "sticky gas", can be greatly improved if the analyte gas is entrained in a channel upon exposure to the sensor.

FIG. 5.10A illustrates a configuration for gas sensor testing and FIG. 5.10B illustrates a top view of a sensor showing a PS surface between gold pads for electrical connection.

FIG. 6.1 illustrates the relative sensitivity of PS to 1, 2, 3, 4, and 5 ppm of NO for an untreated PS surface. The response is linear and close to 2 Ohms/ppm.

FIG. 6.2 illustrates the response of $NO_2$ to a "p-type" PS sensor used in this study. The return to baseline is not complete at this concentration as $NO_2$ sticks to the surface in this open experimental configuration (Ref. 16-FIG. 2). See the experimental section and note also the discussion in Ref. 5.

FIG. 6.3A-E illustrates the response to 1 PPM NO of untreated and $SnO_2$ (FIG. 6.3A (upper curve on left, first NO spike is untreated, and lower curve on left is treated and NO spike around 600)) to NO)), NiO (FIG. 6.3B (upper curve on left is treated and NO spike around 550, and lower curve on left is untreated with spike around 600)), $Cu_xO$ (FIG. 6.3C (upper curve on left, first NO spike at about 100 is for untreated, and lower curve on left is treated and NO spike around 160)), $Au_xO$ (FIG. 6.3D (upper curve on left, first NO curved spike is untreated, and lower curve on left is treated and NO sharp spike around 1200)) nanostructure treated PS. The first region corresponds to an $N_2$ purge for base resistance stabilization until NO is introduced. The sharp "transient" decrease in signal corresponds to the formation of $NO_2$. After 300 s of exposure, NO is turned off and the surface is purged with $N_2$. Note the scales to left (PS) and right (treated PS). Here the sensor is operated in an unsaturated mode. The saturation response to 10 ppm NO is depicted in FIG. 6.3E. Here the sensor is exposed to $N_2$ for resistance stabilization, followed by conversion of NO to $NO_2$ and subsequent increase and saturation of the response to NO. See text for discussion.

FIG. 6.4 illustrates the comparison of metal oxide (usually $SnO_2$ or $WO_3$) elevated temperature (150-500 C) heat controlled sensors separated from their electronics by a channel with a heat sunk PS sensor operating at room temperature and capable of operation to temperatures of at least 183° C.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

The term "detectable" refers to the ability to detect a signal over the background signal.

The term "detectable signal" is a signal derived from an impedance change upon the interaction of a gas with a porous silicon layer or a porous silicon layer having a nanostructured deposit on the porous silicon layer. The detectable signal is detectable and distinguishable from other background acoustic signals that are generated from the host. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, 40% or more difference between the detectable signal and the background) between detectable signal and the background. Standards and/or calibration curves and/or arrays of porous silicon sensors can be used to determine the relative intensity of the detectable signal and/or the background.

Discussion

Embodiments of the present disclosure include sensors, arrays of conductometric porous silicon (PS) sensors, devices including conductometric PS sensors, methods of making conductometric PS sensors, methods of using conductometric PS sensors, methods of selecting a nanostructured deposit for a conductometric PS sensor, methods of detecting a gas based on acidic or basic characterisitics of the gas using a conductometric PS sensor, methods of rejuvenating conductometric PS sensors, and the like.

The conductometric PS gas sensor (also referred to as a "PS gas sensor" or "conductometric PS sensor") is operative to measure an impedance change that corresponds to a gas concentration (e.g., a gas concentration can be determined based on the impedance change or the magnitude of the impedance change and this concentration can be independently evaluated for calibration). More particularly, the conductometric PS sensor transduces the presence of a gas into an impedance signal, which is measured by another device in communication with the conductometric PS sensor. Therefore, the term "measure" used in reference to the conductometric PS sensor can include the conductometric PS sensor in combination with another circuit or device (e.g., impedance analyzer, sensor and shunt circuit, and the like) to measure the impedance (e.g., the detectable signal). The conductometric PS can be used to detect gases or liquids. In particular, conductometric PS sensors, in accordance with the present disclosure, have a rapid and reversible response to analyte gases at room temperature.

Embodiments of the present disclosure provide for a concept that is predictive of significant and predictable changes in conductometric PS sensor sensitivity for a variety of gases. Rapidly responding, reversible, sensitive, and selective conductometric PS sensors are formed (1) with a highly efficient electrical contact to a porous silicon layer (e.g., a nanopore covered microporous layer) and (2) selective nanostructured deposit (e.g., nanostructure and/or nanostructured deposit), interaction, and modification of the porous silicon layer, using embodiments of the present disclosure. A nanostructured deposit of distinctly variable nanostructures can be chosen to be deposited on a portion of the porous silicon layer, where the resulting conductometric PS sensors provide a range of sensitivities for a given analyte using a concept complementary to that of hard and soft acid-base interactions (HSAB) and commensurate with a basis in dominant physisorption. Physisorption interaction involves intermolecular forces (e.g., a van der Waals or comparable attraction) between the gas and nanostructured deposit. Physisorption interaction does not involve a significant change in the electronic orbital patterns of the nanostructured deposit and the gas. A physisorption interaction is a reversible interaction of the nanostructured deposit with the gas. A physisorption interaction is not a chemisorption reaction that involves a chemical reaction that may not be reversible. The concept, based on the reversible interaction of hard acids and bases with soft bases and acids corresponds (1) to the inverse of the HSAB concept and (2) to the selection of conductometric PS sensor and a porous silicon surface (e.g., nanostructured deposit) and analyte materials which do not result in strong covalent or ionic bonding but rather represent a much weaker mixed orbital interaction where a significant HOMO-LUMO and additional orbital mismatches dominate so that the interaction is a reversible physisorption interaction. Embodiments of the present disclosure provide for notably higher sensitivities and selectivity based on impedance changes (See Example 1 and 2).

Embodiments of the present disclosure are advantageous for at least the following reasons: (1) its sensitivity and short recovery time, (2) its operation at room temperature as well as at a single, readily accessible, temperature with an insensitivity to temperature drift, (3) its potential operation in a heat-sunk configuration allowing operation to a surface temperature of 80° C. even in highly elevated temperature environments (in sharp contrast to metal oxide sensors), (4) its ease of coating with diversity of gas-selective materials to form sensor arrays, (5) its low cost of fabrication, (6) its low cost and ease of rejuvenation after contamination, (7) its low cost of operation, and (8) its ability to rapidly assess false positives by operating the sensor in a pulsed gas mode.

It should be noted that the time frame for measuring the gas concentration depends, in part, on the particular application and gas being measured, where the presence of the gas can be measured in a time frame as short as 2 seconds in some embodiments, while in other embodiments, the time frame for a precise concentration measurement may be longer. It should be noted that impedance includes contributions from one or more of resistance, capacitance, and inductance, and measurement of impedance includes the measurement of one or more of resistance, capacitance, and inductance. In an embodiment, the impedance analyzer measures the resistance and capacitance only.

Embodiments of the present disclosure can be used to measure the concentration of a gas when the gas or the gas mixture is known or substantially known. For example, if the environment that the conductometric PS sensor is to be used in is known to include ammonia, the conductometric PS sensor can be used to measure the concentration of ammonia. In another example, if the environment that the conductometric PS sensor is to be used is known to include ammonia and $H_2S$, then an array matrix of conductometric PS sensors (e.g., 2, 3, 4, 6, 8, or more) can be used to measure the concentration of each gas or the relative concentration of each gas. In an embodiment, the array of conductometric PS sensors can be designed so that each of the conductometric PS sensors can detect a specific gas. In addition, the array of conductometric PS sensors allows the concentration of the gases to be compared to one another on relative terms.

Embodiments of the present disclosure can be used to determine the type of gas(es) present in an environment. For example, although the exact gas in the environment is unknown or not known for certain, embodiments of the present disclosure can be used to determine if the gas is a hard, intermediate, or soft, acid or base, and/or its concentration or relative concentration. In particular, an array of conductometric PS sensors (e.g., 2, 3, 4, 6, 8, 10, or more) can be used where the array of conductometric PS sensors includes a variety of nanostructured deposits (e.g., each conductometric PS sensor has a different nanostructured deposit), where the variety of nanostructured deposits can range from a hard acid to a soft acid or a hard base to a soft base and in areas between these so that the gas type can be correlated to the type of nanostructured deposit based on the teachings of the present disclosure. Depending on the specificity desired, the number of conductometric PS sensors in the array with the variety of nanostructured deposits can range from two to several depending on the gas mixture to be analyzed. In this way, the acid/base type of the gas can be determined and/or the concentration of the gas can be determined.

The conductometric PS sensor includes a silicon substrate, a protective layer on a portion of the silicon substrate, a porous silicon (PS) layer (or region) on a portion of the silicon substrate that is exposed through the protective layer, and two or more distinct contacts disposed onto a portion of the PS region and the protective layer. A nanostructured deposit is disposed on and/or within the PS layer that are not covered by the contacts, which enables the conductometric PS sensor to respond more strongly to certain gases relative to others depending on the nanostructured metal or metal oxide deposit used.

The protective layer can include, but is not limited to, a silicon carbide layer, a silicon nitride layer, a polymer layer, a silicon oxynitride ($SiO_xN_y$) layer, an insulating dielectric film, a ceramic layer, a photoresist layer, a polyimide layer, and combinations thereof. In an effort to be clear, the protective layer may be referred to as the silicon carbide layer hereinafter, but the protective layer could be any one of the layers described above in other embodiments.

The PS layer can include a macroporous/nanoporous hybrid framework. The macropores can be about 0.5 to 20 μm deep and 1 to 3 μm in diameter, and the nanopores are about 1 to 20 nanometers in diameter. The nanopores are superimposed on the walls of the macropores. The contact can be disposed on and within the macroporous and nanoporous hybrid framework as well as extend above the PS layer and onto the protective layer (e.g., silicon carbide layer). In other words, the material fills in a portion of the PS layer and then forms a layer on top of the PS layer. The contacts are distinct and separated from one another by a space or area (e.g., a portion of the PS layer and a portion of the protective layer). The contact can include one or more contact portions. In other words, one portion can be disposed on the PS layer and one portion disposed on the protective layer, but the two portions are contiguous in that a single metal layer extends from the PS layer onto the top of the PS layer and onto the protective layer. The contacts can be made of a metal or a combination of metals such as, for example, gold, copper, silver, titanium, and combinations thereof. In an embodiment, the contact includes a pre-coating layer usually titanium, and a metal layer usually gold, disposed onto the pre-coating layer. The pre-coating layer can be used to improve the electrical connection of the contact to the PS layer.

As mentioned above, the exposed portion of the PS layer not covered by the contacts can have a nanostructured deposit on and/or within the PS layer (e.g., a combined macroporous/nanoporous hybrid framework). The nanostructured deposit can include, but is not limited to, a metal material, metal oxide material, metal oxynitride material, and combinations thereof. The nanostructured deposit can include, but is not limited to, tin (Sn), gold (Au), palladium (Pd), iridium (Ir), rhodium (Rh), vanadium (Va), ruthenium (Ru), platinum (Pt), titanium, oxides of each metal, oxynitrides of each metal, gold clustered oxides, and combinations thereof. In an embodiment, the nanostructured deposit can be a nanostructured deposit of discrete and/or clustered nanostructures and/or nanomaterials onto and/or with the PS layer. In another embodiment, the nanostructured deposit can be a layer of nanostructures and/or nanomaterials that are deposited onto and/or within the PS layer. In regard to the nanostructured deposit, the phrase "deposit on" includes deposited on and/or within the PS layer, unless otherwise stated.

Embodiments of the conductometric PS sensor having a nanostructured deposit on the PS layer to provide enhanced sensitivity (e.g., CO in the presence of $SnO_2$ nanostructures, $NH_3$ in the presence of gold clustered oxide nanostructures) and selectivity to certain gases (e.g., $NH_3$ in the presence of $NO_x$). In particular, concentrations of select gases can be measured in the presence with one or more additional gases, where selected gases are more strongly sensed (e.g., impedance change detected).

As briefly mentioned above, the conductometric PS sensor responds and is operative to measure an impedance change (e.g., an impedance magnitude change) across a first contact and a second contact that corresponds to a concentration of a gas in contact with the PS surface. The sensitivity of the conductometric PS sensor is defined as the relative increase in impedance over a time frame following exposure to a concentration of a gas of interest. It should also be noted that the sensitivity is, in part, a function of the gas of interest, the gas mixture exposed to the conductometric PS sensor, the PS layer, the processing and preparation of the porous silicon layer (e.g., cleaning with HF and HCl), the nature of the nanostructured deposit, the temperature of the system, the pressure of the system, and combinations thereof.

In general, the conductometric PS sensors have a gas detection lower limit of about 50 parts per billion (ppb), and the presence of the gas measured in as little as 2 seconds. In an embodiment, ammonia and phosphine can be measure at about 50 ppb. Other gas detection limits are given in the Examples.

The operating parameters of the conductometric PS sensor include, but are not limited to, a bias voltage, an AC voltage frequency, an AC voltage amplitude and combinations thereof. The conductometric PS sensors operate at a bias voltage of about 1 and 3000 millivolts DC. Also one can use an AC voltage frequency 100 and 100,000 Hz, an AC voltage amplitude between 1 and 1000 millivolts, or a combination thereof. The conductometric PS sensors operate preferably with no bias voltage, an AC voltage amplitude from 1 to 100 millivolts at an AC voltage frequency of 1000 Hz.

As mentioned briefly above, the impedance change can be measured with an impedance analyzer, a sensor and shunt circuit, or other impedance measurement devices. An embodiment of the sensor and shunt circuit uses a high impedance resistor in parallel with the sensor (conductometric PS sensor or components thereof). The resistor shunts the stray capacitance (removes high frequency noise), resulting in a resistive measurement.

The conductometric PS sensor can be used in a variety of ways including, but not limited to, a stand-alone detector, or a device including an array of stand-alone detectors. The conductometric PS sensor can be used to detect gases (e.g., combustion generated gases such as carbon monoxide, carbon dioxide, sulfur dioxides, nitrogen oxides, hydrogen sulfide, and hydrogen cyanide). In particular, conductometric PS sensors, in accordance with the present disclosure, can provide a rapid and reversible response to analyte gases (e.g., including hydrogen chloride (HCl), ammonia ($NH_3$), phosphine ($PH_3$), carbon monoxide (CO), sulfur dioxide ($SO_2$), hydrogen sulfide ($H_2S$) and nitric oxide ($NO_x$)) at room temperature. Additional details regarding analyte gases are described in the Examples.

In addition, the conductometric PS sensor can be used as an array, where multiple conductometric PS sensors are uniquely sensitive to different gases of interest thereby enabling an array to measure the concentration of multiple gases simultaneously (e.g., an appropriately treated conductometric PS sensor can be made to respond more strongly to one gas over a second gas). In addition, an array of conductometric PS sensors can be used to enhance sensing selectivity as the array of conductometric PS sensors provide multiple data points per tested sample which can be analyzed in a matrix format to provide selectivity for one gas over another based on the individual conductometric PS sensors within the conductometric PS sensor array. Thus, an array of conductometric PS sensors includes conductometric PS sensors sensitive to one gas over another and, in this sense, to select gases.

In this regard, the array of conductometric PS sensors can be used to detect multiple analytes simultaneously, while also enhancing sensing selectivity.

As noted above, the nanostructured deposit and the base porous silicon layer can include a nanostructure or nanomaterial (e.g., a nanoparticle that can include a nanosphere, a nanowire, a nanodisk, and a nanobelt) and/or a coated nanostructure or nanomaterial (i.e., a nanostructure having a material (e.g., a metal, a metal oxide, metalloid, or metalloid oxide) disposed on the nanostructure) can be deposited on the PS layer (e.g., macroporous/nanoporous framework). For example, the nanostructure or nanomaterial can be made of materials such as, but not limited to, metal oxides, silicon (Si), tin (Sn), chromium (Cr), iron (Fe), nickel (Ni), silver (Ag), titanium (Ti), cobalt (Co), zinc (Zn), platinum (Pt), palladium (Pd), osmium (Os), gold (Au), lead (Pb), iridium (Ir), molybdenum (Mo), vanadium (V), aluminum (Al), aluminum oxide ($Al_2O_3$, $AlO_x$), silicon oxide ($SiO_x$), tin oxide ($SnO_x$), chromia ($Cr_2O_3$), iron oxide ($Fe_2O_3$, $Fe_3O_4$, or FeO), nickel oxide (NiO), silver oxide (AgO), titanium oxide ($TiO_2$), cobalt oxide ($CO_2O_3$, $CO_3O_4$, or CoO), zinc oxide (ZnO), platinum oxide (PtO), palladium oxide (PdO), vanadium oxide ($VO_2$), molybdenum oxide ($MoO_2$), lead oxide (PbO), titanium oxide ($TiO_x$), titanium nitride ($TiN_x$), titanium oxinitride ($TiO_xN_y$), and combinations thereof. In this regard, by using these materials, the conductometric PS sensor can be designed to provide selectivity for a particular gas using methods described herein.

As mentioned above, embodiments of the present disclosure include methods of selecting a nanostructured deposit for a conductometric PS sensor. The nanostructured deposit can be selected so as to maximize the impedance change relative to a testing conductometric PS sensor (e.g., a background testing conductometric PS sensor or other conductometric PS sensors). By maximizing the impedance change, the conductometric PS sensor can be designed to most effectively detect the gas of interest. Further a range of gas sensitivities can be developed for a gas by varying the deposit on the porous silicon surface. Thus, for a gas or a gas mixture, an array of conductometric PS sensors can be used to measure the concentration of a gas or a mixture of gases or can be used to classify a gas as a hard, intermediate, or soft, acid or base, and its relative acidity or basicity relative to a given nanostructured deposit (or a group of nanostructured deposits in an array) can be evaluated. In addition, the nanostructured deposit can be selected so as to maximize the impedance change relative to a testing conductometric PS sensor where the gas of interest is in a gas mixture. Thus, the conductometric PS sensor can be designed to selectively detect a gas in a gas mixture. In addition, a device can include an array of conductometric PS sensors, so embodiments of the present disclosure enable the selection of the nanostructured deposit for each of the modified conductometric PS sensors in the array so as to maximize the impedance change measured for each gas. It should be noted that maximizing the impedance change does not always include the absolute maximum impedance change rather it can include the relative maximum impedance change relative to one or more other PS gas sensors that detect one or more other gases of interest and/or a baseline background gas (e.g., air). A matrix of these results is analyzed for the gas mixture.

In an embodiment, the method can include exposing a gas to a plurality of testing conductometric PS sensors. Each of the testing conductometric PS sensors is operative to transduce the presence of a gas into an impedance change, where the impedance change correlates to the gas concentration. In an embodiment, the testing conductometric PS sensor has a porous silicon layer. One or more of the testing conductometric PS sensors has a nanostructured deposit disposed on the porous silicon layer. The nanostructured deposit can be selected from: a nanostructured deposit having the characteristic of a hard acid, a nanostructured deposit having the characteristic of an intermediate acid, a nanostructured deposit having the characteristic of a soft acid, a nanostructured deposit having the characteristic of a hard base, a nanostructured deposit having the characteristic of an intermediate base, and a nanostructured deposit having the characteristic of a soft base.

The concept of chemical hardness/softness has its basis in the nature of metal ion complexation in aqueous solution. It is a generalization of the Lewis acid/base concept. The properties of acids and bases (e.g., gases or nanostructured deposits having the characteristic of a type of acid or base) can be described as hard and soft based upon the correlation of several atomic/molecular properties which include the ionization potential, I, the electron-affinity, A, and the chemical potential, $\mu$, in concert also with the HOMO-LUMO gap concept from molecular orbital theory. A few examples of the groups of hard, borderline, and soft acids and bases are given in Table 2 in the Examples. Whereas for a soft acid, the acceptor atom is of low positive charge, of large size, and has polarizable outer electrons, in a hard acid, the acceptor atom is of small size and not easily polarized. In a soft base, in precise contrast to a hard base, the donor atom is of low electronegativity, easily oxidized, and highly polarizable, with low-lying empty molecular orbitals. The HSAB principle was initially based on empirical observations. Yet, as it groups acids and bases, a basis for it has been developed in terms of DFT and follows the principle that soft-soft combinations depend mainly on covalent bonding and hard-hard combinations depend mainly on ionic bonding. Further the HSAB principle states that hard acids prefer to coordinate to hard bases whereas soft acids prefer to coordinate to soft bases. Additional details regarding the types of acids and bases are described in Examples 1 and 2.

In an embodiment, an intermediate acid has characteristics that are between a hard acid and a soft acid. In an embodiment, an intermediate base has characteristics that are between a hard base and a soft base.

Examples 1 and 2 will describe embodiments of different types of gases and nanostructured deposits in terms of a hard, an intermediate, or a soft, acid or base.

Next, an impedance change is measured using each of the testing conductometric PS sensors relative to a standard testing conductometric PS sensor. A standard testing conductometric PS sensor can be used to define a baseline with which to compare the impedance of the testing conductometric PS sensors having a nanostructured deposit. In an embodiment, a standard testing conductometric PS sensor would not be used, and matched base (standard) porous silicon surfaces would be used and compared to the testing conductometric PS sensors.

Subsequently, the nanostructured deposit can be selected to modify the base porous silicon layer of the sensor using the concept that the nanostructured deposit and the gas have complementary characteristics based on the interactions of two of the following: a hard acid, an intermediate acid, a soft acid, a hard base, an intermediate base, and a soft base. The reversible interaction (physisorption) between the gas and the nanostructured deposit determines the measured impedance change, which can be compared to the impedance change measured using the standard testing conductometric PS sensor. The combination of the nanostructured deposit and the gas to be sensed by the testing conductometric PS sensors generates a range of impedance changes, where the greatest impedance change is determined by the maximum acid-base mismatch between the gas and the nanostructured deposit. The maximum acid-base mismatch between the gas and the nanostructured deposit typically occurs when the gas to be tested is a hard base and the nanostructured deposit is a soft acid or when the gas to be tested is a hard acid and the nanostructured deposit is a soft base. Additional details are described herein and in Examples 1 and 2.

In an embodiment, if the gas to be sensed has the characteristic of a hard acid, a nanostructured deposit having the characteristic of a soft base is selected for use in a conductometric PS sensor to maximize the impedance change.

In an embodiment, if the gas to be sensed has the characteristic of a hard base, a nanostructured deposit having the characteristic of a soft acid is selected to maximize the impedance change.

In an embodiment, if the gas to be sensed has the characteristic of a hard acid, a nanostructured deposit that does not have the characteristic of a hard base is selected, since a hard acid and a hard base will not have a strong orbital mismatch between the gas and the nanostructured deposit and can interact chemically to form a strong ionic bond.

In an embodiment, if the gas to be sensed has the characteristic of a soft acid, a nanostructured deposit that does not have the characteristic of a soft base is selected since a soft acid and a soft base will not have a strong orbital mismatch between the gas and the nanostructured deposit and can interact chemically to form a covalent bond.

In an embodiment, if the gas to be sensed has the characteristic of a hard base, a nanostructured deposit that does not have the characteristic of a hard acid is selected since a hard base and a hard acid will not have a strong orbital mismatch between the gas and the nanostructured deposit and can interact chemically to form a strong ionic bond.

In an embodiment, if the gas to be sensed has the characteristic of a soft base, a nanostructured deposit that does not have the characteristic of a soft acid is selected since a soft base and a soft acid will not have a strong orbital mismatch between the gas and the nanostructured deposit and can interact chemically to form a strong covalent bond.

In an embodiment, if the gas to be sensed has the characteristic of an intermediate acid, a nanostructured deposit that does not have the characteristic of an intermediate base but is strongly hard or soft is selected since an intermediate acid and an intermediate base will not have a strong orbital mismatch between the gas and the nanostructured deposit.

In an embodiment, if the gas has the characteristic of an intermediate base, a nanostructured deposit that does not have the characteristic of an intermediate acid but is strongly hard or soft is selected since an intermediate base and an intermediate acid will have will not have a strong mismatch between the gas and the nanostructured deposit.

As mentioned above, two or more conductometric PS sensors (e.g., 3, 4, 5, 6, 10, 15, or more) can be exposed to a gas to produce a range of responses based on the selection of the nanostructured deposits used for a conductometric PS sensor that is to be used to detect a particular gas (e.g., to detect a specific gas). In this way, the most appropriate nanostructured deposits can be selected for a specific gas (e.g., the gas being tested) and a range of responses can be generated to obtain a clear identification. The following paragraphs describe a number of embodiments including the use of two and three conductometric PS sensors. However, additional conductometric PS sensors can be used. For example, five, ten, or more conductometric PS sensors can be used so that multiple nanostructured deposits having the characteristic of a hard acid (or base), a soft acid (or base), and/or an intermediate acid (or base), so that the most appropriate nanostructured deposit can be selected for use to detect the gas of interest.

In an embodiment, two conductometric PS sensors can be exposed to a gas. One of the conductometric PS sensors has a nanostructured deposit having the characteristic of a hard acid and the other of the conductometric PS sensors has a nanostructured deposit have a characteristic of a soft acid, where the use of this combination of sensors creates a range of impedance changes. In this way the measured impedance changes can be used to select an appropriate and/or optimum nanostructured deposit for a specific gas and indicates a range of potential conductormetric porous silicon sensors. In an alternative embodiment, the nanostructured deposit of one of the conductometric PS sensors can have a characteristic of a hard base, while the other of the conductometric PS sensors can have a nanostructured deposit having a characteristic of a soft base.

In another embodiment, three conductometric PS sensors can be exposed to a gas. One of the conductometric PS sensors has a nanostructured deposit having the characteristic of a hard acid. One of the other of the conductometric PS sensors has a nanostructured deposit having a characteristic of a soft acid, while the other of the conductometric PS sensors has a nanostructured deposit having a characteristic of an intermediate acid. The use of this combination of sensors creates a range of impedance changes with which a matrix of detection can be established. In this way the measured impedance changes can be used to select appropriate nanostructured deposits for a specific gas. In an alternative embodiment, the nanostructured deposit of one of the conductometric PS can have a characteristic of a hard base, another of the other of the conductometric PS sensors can have a nanostructured deposit having a characteristic of a soft base, and the other of the conductometric PS sensors can have a nanostructured deposit having a characteristic of an intermediate base.

One or more conductometric PS sensors are included in a device. The conductometric PS sensor includes a silicon substrate having a PS layer, where a nanostructured deposit is disposed on a portion of the PS layer.

If the gas to be sensed has the characteristic of a hard base, the nanostructured deposit which optimizes response should not have the characteristics of a hard acid. If the gas has the characteristic of a soft base, the nanostructured deposit should not have the characteristics of a soft acid. If the gas has the characteristic of an intermediate base, the nanostructured deposit should not have the characteristic of an intermediate acid but should be hard or soft. If the gas has the characteristic of a hard acid, the nanostructured deposit should not have the characteristics of a hard base. If the gas has the characteristic of a soft acid, the nanostructured deposit should not have the characteristic of a soft base. If the gas has the characteristic of an intermediate acid, the nanostructured deposit should not have the characteristic of an intermediate base but should be hard or soft.

The following are embodiments that describe the pairing of the characteristic of the gas and the nanostructured deposit to produce a maximum impedance change. The following embodiments are presented for illustrative purposes only, and additional pairings can be used to produce an appropriate device. As mentioned above, maximizing the impedance change for one gas does not include maximizing the absolute maximum impedance change for several gases rather it can include the relative maximum impedance change for these gases relative to one or more other conductometric PS sensors that detect one or more of these gases of interest and/or a baseline background gas (e.g., air).

In an embodiment, the gas has the characteristic of a hard acid and the nanostructured deposit has the characteristic of a soft base to produce a maximum impedance change. In an embodiment, the gas has the characteristic of a soft acid and the nanostructured deposit has the characteristic of a hard base to produce a maximum impedance change.

In another embodiment, the gas has the characteristic of a hard base and the nanostructured deposit has the characteristic of a soft acid to produce a maximum impedance change. In another embodiment, the gas has the characteristic of a soft base and the nanostructured deposit has the characteristic of a hard acid to produce a maximum impedance change.

In another embodiment, the gas has the characteristic of an intermediate base and the nanostructured deposit does not have the characteristic of an intermediate acid. The nanostructured deposit may be a hard acid or a soft acid but must be notably shifted in strength from the intermediate case.

In an embodiment, the gas has the characteristic of an intermediate acid and the nanostructured deposit does not have the characteristic of an intermediate base. The nanostructured deposit may be a hard base or a soft base but must be notably shifted in strength from the intermediate case.

As mentioned above, embodiments of the present disclosure include methods of cleaning or rejuvenating conductometric PS sensors. Over time, in the course of preparation, and/or after use, the surface of the conductometric PS sensor can become contaminated so that the conductometric PS sensor does not respond or the response is compromised. Embodiments of the conductometric PS sensor can be rejuvenated using one of a number of rejuvenating solutions. These rejuvenating solutions are applied by exposing the PS surface (e.g., with or without the nanostructured deposit on the PS surface) to one or more (e.g., sequentially or at the same time) of a variety of solutions as appropriate to the limited ranges of contamination. In an embodiment, the concentration and/or time of exposure is set so to not damage the sensor or cause deterioration of the sensor or sensor response.

In one embodiment, the PS surface contaminated with residual tetrabutyl-ammonium perchlorate associated with the etching process that quenches the sensor response is exposed to an acetonitrile soak (e.g., the concentration can range based on degree of contamination and the time for the soak, but the acetonitrile is not used in a manner or time frame to cause harm to the PS surface of sensor) to provide for its efficient removal and insure the best possible response.

In another embodiment, sensors which have lost their response to contamination resulting from continued exposure are treated with a dilute HF and/or HCl solution. A dilute HF (and/or HCl) solution is a solution having a concentration that rejuvenates the PS sensor without destroying or deteriorating the metal or metal oxide pre-coating so that the result is a PS sensor that functions normally or as it functioned prior to being contaminated.

In particular, the HF solution is made by diluting a standard HF solution (about 49% by volume HF) with an alcohol (e.g., methanol, ethanol, and the like) in a ratio of about 1:10 to 1:30 or about 1:20, to minimize the interaction with the metal pre-coating (e.g., titanium pre-coating). In an embodiment, the conductometric PS sensor can be exposed to the HF solution from a few minutes (e.g., 4 to 30 min or more) one or more times, depending on the conductometric PS sensor, the degree of contamination, and the like. FIG. 2.5 in Example 1 illustrates the impedance change before and after rejuvenation.

In particular, an embodiment of the method of treating a porous silicon sensor (e.g., a conductometric PS sensor) includes providing a porous silicon sensor having a porous silicon layer, where the porous silicon layer is contaminated so that the response of the porous silicon sensor is significantly reduced. The phrase "substantially reduced" refers to a porous silicon sensor that has a response that is less than about 50% of the porous sensor prior to use, but the rejuvenation method can be applied to any form of sensor whose response is less than that of the original sensor. The porous silicon sensor can be exposed to a dilute HF solution, for example. After exposure, the response of the porous silicon sensor is substantially the response of the porous silicon sensor prior to use. The term "substantially" refers to about 50%, about 60%, about 70%, about 80%, about 90%, about 95%, or about 99%. In other words, after exposure to the dilute HF solution the previously contaminated PS layer is rejuvenated or cleaned so that the porous silicon sensor after exposure has a response that is about 50%, about 60%, about 70%, about 80%, about 90%, about 95%, or about 99% prior to being contaminated.

Embodiments of the present disclosure also include methods of making conductometric PS sensors. In general, the conductometric PS sensor can be fabricated by first providing a silicon substrate having a protective layer, such as a silicon carbide layer, disposed on a first portion of the silicon substrate. Then, a first area on the silicon substrate is converted into a PS layer, where the first area does not have a silicon carbide layer disposed thereon. Next, a first contact (e.g., a first contact pre-coating (e.g., Ti or Cr) and the first contact (e.g., Au)) is formed onto a first portion of the PS layer and onto a first portion of the silicon carbide layer. The first portion of the silicon carbide layer is contiguous with the first portion of the PS layer as described above. A second contact (e.g., a second contact pre-coating (e.g., Ti or Cr) and the second contact (e.g., Au)) is formed onto a second portion of the PS layer and onto a second portion of the silicon carbide layer. The second portion of the silicon carbide layer is contiguous with the second portion of the PS layer as described above. A third portion of the PS layer is between the first portion and the second portion of the PS layer. The first and second contacts can be formed at the same time. Specifically, the first and the second contact pre-coatings are formed and then the first and second contacts are formed on the first and second contact pre-coatings, respectively. The first and second contact pre-coatings are advantageous in that the first and second contacts enable a superior electrical connection to be formed. In addition, the first and second contacts can be formed using a shadow mask technique.

Additional fabrication steps can be conducted. For example, an additional fabrication step includes cleaning the PS layer with a mixture of one part hydrochloric acid (about 44%) in about five parts methanol for about four hours, for example. In addition, a fabrication step for forming a nanostructured deposit on the porous silicon layer can be performed. Additional details regarding the fabrication of the conductometric PS sensor are described in reference to FIG. 1.2A through 1.2I.

After the conductometric PS sensor is formed, the conductometric PS sensor can be validated. In this regard, embodiments of this disclosure include methods of selecting a conductometric PS sensor having certain performance characteristics, methods of analyzing the data measured using the conductometric PS sensor, and methods of measuring the concentration of a gas. In addition, the method of validating includes detecting false positives (e.g., determining that an impedance change is from the gas of interest and not a response caused by another source) (See, U.S. Pat. Nos. 6,673,644, 6,893,892, and 7,141,859, each of which is incorporated herein by reference). Furthermore, the present disclosure provides methods of analyzing data for the conductometric PS sensor as well as for other devices and sensors.

Now having described the conductometric PS sensor, the following non-limiting figures are provided to provide additional details regarding the conductometric PS sensor.

FIG. 1.1A illustrates a cross-sectional view of a conductometric PS sensor 100a, while FIG. 1.1B illustrates a cross-sectional view of a conductometric PS sensor 100b. The conductometric PS sensor 100a shown in FIG. 1.1A includes a silicon substrate 102, a silicon carbide layer 104, a PS layer 112, a first contact pre-coating layer 118a, a first contact 114a, a second contact pre-coating layer 118b, and a second contact 114b. In FIG. 1.2H for example, the first contact pre-coating layer 118a (not shown for clarity), first contact 114a, a second contact pre-coating layer 118b (not shown for clarity), and the second contact 114b include a first PS metallized layer 116a and a second PS metallized layer 116b, respectively. As mentioned above in general, a first metal layer can disposed on a first portion of the PS layer (first PS metallized layer 116a) and a first portion of the silicon carbide layer to form the first contact 114a, while a second metal layer is disposed onto/within a second portion of the PS layer (second PS metallized layer 116b) and a second portion of the silicon carbide layer to form the second contact 114b (the first and second contact pre-coating layer 118a and 118b are not shown for clarity).

The first portion of the silicon carbide layer is contiguous with the first portion of the PS layer, while the second portion of the silicon carbide layer is contiguous with the second portion of the PS layer. The first portion of the PS layer and the second portion of the PS layer are not contiguous and a space (e.g., PS layer between these two portions) separates the two layers. The first portion of the silicon carbide layer and the second portion of the silicon carbide layer are not contiguous and space (e.g., silicon carbide layer) separates the two layers. As a result, the first contact 114a and the second contact 114b are separated from one another. The PS gas sensor is operative to measure an impedance change across the first contact and the second contact that can correspond to a gas concentration present in the total gas exposed to the PS gas sensor.

The PS layer 112 is fabricated from the silicon substrate 102 using techniques discussed above to form a nanoporous or a macroporous/nanoporous PS framework. A portion of each of the first and second contacts pre-coating layer 118a and 118b and the first and second contacts 114a and 114b is disposed within the PS layer 112, while the remaining portion of the first and second contacts pre-coating layer 118a and 118b and the first and second contacts 114a and 114b are disposed above the framework and extend above the PS layer 112 onto the silicon carbide layer 104. In other words, the first and second contacts pre-coating layer 118a and 118b and the first and second contacts 114a and 114b are included within the macroporous/nanoporous regions of the PS layer 112, while the remaining portion of the contacts are disposed above the PS layer 112 and on a portion of the silicon carbide layer.

The silicon substrate 102 can include wafers, such as, but not limited to, silicon wafers, doped silicon wafers, p-type boron doped silicon wafers. The silicon substrate 102 can have dimensions appropriate to form a PS region as well as appropriate for a particular application. The silicon carbide layer 104 can be deposited using PECVD (plasma enhanced chemical vapor deposition) at about 200° C. to 300° C. and at about 500 to 1000 mTorr, and preferably at 250° C. and about 800 mTorr in a Unaxis PECVD. $SiH_4$ (300 sccm), He (700 sccm), and $CH_4$ (100 sccm) with 50 W of power are usually used. The silicon carbide layer 104 can be between about 100 to 500 nanometers (nm) thick, and preferably 200 nm thick. As mentioned above, other materials can be used in place of the silicon carbide layer 104 such as, but not limited to, a silicon nitride layer, a polymer layer, an $SiO_xN_y$ layer, an insulating dielectric film, a ceramic layer, a photoresist layer, and a polyimide layer.

The PS layer 112 is a macroporous/nanoporous framework (i.e., a macroporous framework on which is superimposed a nanoporous layer). The macroporous framework can include pores approximately 1 to 2 µM wide and from about 0.5 to 20 µm deep and about 0.5 to 3 µm in diameter, while also having nanopores throughout the macroporous framework located on the walls of the micropores. The PS layer 112 can be prepared by electrochemically etching a portion of the silicon substrate with acetonitrile, hydrofluoric acid, tetrabutylammonium-perchlorate (TBAP), and water, for example. Additional details regarding the preparation of the PS layer 112 are presented in more detail above.

As described above, the first contact pre-coating layer 118a and the second contact pre-coating layer 118b can be disposed on the PS layer 112 and on the silicon carbide layer 104. Subsequently, the contacts 114a and 114b can be disposed on the first contact pre-coating layer 118a and the second contact pre-coating layer 118b, the PS layer 112, and on the silicon carbide layer 104. In general, the first contact pre-coating layer 118a and the second contact pre-coating layer 118b and the contacts 114a and 114b can be formed by exposing the PS layer 112 using electron-beam metal evaporation or PL induced metallization, for example. The first contact pre-coating layer 118a and the second contact pre-coating layer 118b can be made from titanium or chromium, for example, and can be about 100 to 300 angstroms thick or about 200 angstroms thick. The first and second contacts 114a and 114b can be made of metals, such as, but not limited to, gold (Au), silver (Ag), copper (Cu), and combinations thereof, and can be about 1000 to 4000 angstroms thick or about 3000 to 5000 angstroms thick to facilitate wire bonding.

As shown in FIGS. 1.1A and 1B, the PS gas sensors 100a and 100b include two contacts 114a and 114b. However, additional contacts (i.e., four, five, or more contacts) can be used in other embodiments.

For the purposes of illustration only, and without limitation, embodiments of the present disclosure will be described with particular reference to the below-described fabrication method. Note that not every step in the process is described with reference to the process described in the figures hereinafter. Therefore, the following fabrication process is not intended to be an exhaustive list that includes every step required for the fabrication of the embodiments of the PS gas sensors 100a.

FIG. 1.2A-1.2H illustrate cross-section views of the PS gas sensors 100a shown in FIG. 1.2A during a representative fabrication process. FIG. 1.2A illustrates a silicon substrate 102 having a silicon carbide layer 104 disposed thereon. FIG. 1.2B illustrates a mask 106 disposed onto the silicon carbide layer 104. The mask 106 can be made of materials such as, but not limited to, polymers.

FIG. 1.2C illustrates the etching of the silicon carbide layer 104 into two regions using reactive ion etching. FIG. 1.2D illustrates the removal of the mask 106 thereby exposing the two portions of the silicon carbide layer 104.

FIG. 1.2E illustrates the silicon substrate 102 after a portion of the silicon substrate 102 is electrochemically etched to form a PS region 112 disposed between the two portions of the silicon carbide layer 104.

FIG. 1.2F illustrates a mask 118 (e.g., a shadow mask) disposed onto the silicon carbide layer 104 and the PS region 112. The pattern of the mask 118 exposes two portions of the PS region 112. The shadow mask can be made of a metal (e.g., copper), but the shadow mask can be made of other materials such as polymer, composites, and other masking materials. This step can be performed without exposing the PS region 112 to water, which is advantageous because the exposure of PS to water will result in the decreased sensitivity of the surface due to oxidation.

FIG. 1.2G illustrates the formation of the first contact 114a and the second contact 114b onto the two exposed portions of the PS region 112. The first contact 114a and the second contact 114b can be disposed on the macroporous/nanoporous regions (116a and 116b) of the PS region 112. A portion of the first contact 114a and the second contact 114b are also disposed on portions of the silicon carbide layer 104 (the spatial relationships are described in more detail above). The first contact 114a and the second contact 114b can be disposed onto the two portions of the PS substrate 112 via techniques such as, but not limited to, electron-beam evaporation, sputtering, silk-screen printing, electroless plating, and electroplating.

It should be noted for reasons of clarity, the first contact pre-coating 118a and the second contact pre-coating 118b are shown in the figure. However, the first contact pre-coating 118a and the second contact pre-coating 118b are disposed on the macroporous/nanoporous regions (116a and 116b) of the PS region 112 prior to disposing the first contact 114a and the second contact 114b. The first contact pre-coating 118a and the second contact pre-coating 118b can be disposed onto the two portions of the PS substrate 112 via techniques such as, but not limited to, electron-beam evaporation, sputtering, silk-screen printing, electroless plating, and electroplating. In addition, the first contact pre-coating 118a and the second contact pre-coating 118b are not shown in FIG. 1.2H.

FIG. 1.2H illustrates the removal of the mask regions 118, thereby exposing the first contact 114a and the second contact 114B and the PS layer 112. Additional post processing steps can be performed on the structure. For example, the PS layer 112 can be treated with a mixture of HCl and methanol to enhance the gas detection characteristics.

FIG. 1.2I illustrates the addition of the nanostructured deposit 122 onto the PS layer 112. The nanostructured deposit 122 can be formed using techniques such, but not limited to, electron-beam evaporation, sputtering, silk-screen printing, electroless plating, and electroplating.

Embodiments of the present disclosure can be used to determine an acidic or basic characteristic of a gas or the type of gas (e.g., hard, intermediate, or soft, acid or base). A gas can be exposed to a plurality of conductometric PS sensors. Each of the conductometric PS sensors has a porous silicon layer. One or more of the conductometric PS sensors has a nanostructured deposit disposed on the PS layer. The nanostructured deposit is selected from: a nanostructured deposit having the characteristic of a hard acid, a nanostructured deposit having the characteristic of an intermediate acid, a nanostructured deposit having the characteristic of a soft acid, a nanostructured deposit having the characteristic of a hard base, a nanostructured deposit having the characteristic of a intermediate base, and a nanostructured deposit having the characteristic of a soft base. The nanostructured deposit used is based on the concept that the nanostructured deposit and the gas have characteristics based on the interactions (physisorption) of two of the following: a hard acid, an intermediate acid, a soft acid, a hard base, an intermediate base, and a soft base, where such interaction between the gas and the nanostructured deposit determines the measured impedance change.

Next, an impedance change is measured using each of the testing conductometric PS sensors relative to a standard testing conductometric PS sensor. A standard testing conductometric PS sensor can be used to define a baseline with which to compare the impedance of the testing conductometric PS sensors having a nanostructured deposit. In an embodiment, a standard testing conductometric PS sensor would not be used, and a matched (standard) porous silicon sensor would be used and compared to the testing conductometric PS sensors.

Subsequently, the method includes determining if the gas has the characteristic of a hard acid, an intermediate acid, a soft acid, a hard base, an intermediate base, or a soft base, based on the impedance change of the conductometric PS sensors. As noted above and in Examples 1 and 2, the interaction (physisorption) of a gas having a characteristic of a hard acid and a nanostructured deposit having the characteristic of a soft base yields a larger impedance change than the interaction of the gas with a nanostructured deposit having the characteristic of a hard base. Thus, comparing the various impedance changes for the different nanostructured deposits can provide information about the acidic or basic characteristic of the gas. In an embodiment, a single conductometric PS sensor could be used to provide information about the acidic or basic characteristic of the gas. For example, if the gas has a characteristic of a hard base and the nanostructured deposit on the conductometric PS sensor has the characteristic of a soft acid, then one would expect a maximum impedance change. In contrast, if the nanostructured deposit on the conductometric PS sensor has the characteristic of a hard acid, one would expect a small or very limited impedance change.

The following paragraphs provide examples of how the acidic or basic nature of the gas can be determined. It is to be noted that two or more conductometric PS sensors (e.g., 3, 4, 5, 7, 10, 15, or more) can be used to determine the acidic or basic nature of the gas.

In an embodiment, a) if one of the conductometric PS sensors has a nanostructured deposit having the characteristic of a hard acid and b) if one of the conductometric PS sensors has a nanostructured deposit having the characteristic of a soft acid, and the impedance change is greater for a), then the gas is not a hard base.

In another embodiment, a) if one of the conductometric PS sensors has a nanostructured deposit having the characteristic of a hard acid and b) wherein if one of the conductometric PS sensors has a nanostructured deposit having the characteristic of a soft acid, and the impedance change is greater for b) then the gas is not a soft base.

In an embodiment, a) if one of the conductometric PS sensors has a nanostructured deposit having the characteristic of a hard base and b) if one of the conductometric PS sensors has a nanostructured deposit having the characteristic of a soft base, and the impedance change is greater for a), then the gas is not a hard acid.

In another embodiment, a) if one of the conductometric PS sensors has a nanostructured deposit having the characteristic of a hard base and b) wherein if one of the conductometric PS sensors has a nanostructured deposit having the characteristic of a soft base, and the impedance change is greater for b) then the gas is not a soft acid.

As noted above, embodiments of the present disclosure include methods of detecting a gas based on the acidic or basic characteristic of the gas using a conductometric PS sensor. First, a gas or gas mixture of interest is exposed to one or more conductometric PS sensors. The conductometric PS sensor has a PS layer. One or more of the conductometric PS sensors has a nanostructured deposit disposed on the PS layer, where the nanostructured deposit is selected from: a nanostructured deposit having the characteristic of a hard acid, a nanostructured deposit having the characteristic of a intermediate acid, a nanostructured deposit having the characteristic of a soft acid, a nanostructured deposit having the characteristic of a hard base, a nanostructured deposit having the characteristic of a intermediate base, and a nanostructured deposit having the characteristic of a soft base. The nanostructured deposit used is based on the concept that the nanostructured deposit and the gas have characteristics based on the interactions (physisorption) of two of the following: a hard acid, an intermediate acid, a soft acid, a hard base, an intermediate base, and a soft base. Such interaction between the gas and the nanostructured deposit determines the measured impedance change, where the greatest impedance change is obtained by using a nanostructured deposit and the gas promoting an interaction that generates the maximum hard acid and soft base or hard base and soft acid mismatch as described herein.

In an embodiment, the gas has the characteristic of a hard acid and the nanostructured deposit has the characteristic of a soft base. In another embodiment, the gas has the characteristic of a hard base and the nanostructured deposit has the characteristic of a soft acid.

Next, an impedance change is measured using each of the testing conductometric PS sensors relative to a standard testing conductometric PS sensor. A standard testing conductometric PS sensor can be used to define a baseline with which to compare the impedance of the testing conductometric PS sensors having a nanostructured deposit. In an embodiment, a standard testing conductometric PS sensor would not be used, and matched base (standard) porous silicon sensor would be used and compared to the testing conductometric PS sensors.

Subsequently, the greatest impedance change can be obtained using the conductometric PS sensor that has a nanostructured deposit that interacts with the gas to produce the maximum orbital acid-base mismatch as described herein.

EXAMPLES

Now having described the embodiments of the present disclosure, in general, the following examples describe some additional embodiments of the present disclosure. While embodiments of the present disclosure are described in connection with the examples and the corresponding text and figures, there is no intent to limit embodiments of the present disclosure to this description. On the contrary, the intent is to cover all alternatives, Modifications, and equivalents included within the spirit and scope of embodiments of the present disclosure.

Example 1

Brief Summary of Example 1

Within the framework of nanotechnology, we outline a general concept which facilitates significant and predictable changes in sensor sensitivity for a variety of gases. Rapidly responding, reversible, sensitive, and selective porous silicon-based sensors are formed (1) with a highly efficient electrical contact to a nanopore covered microporous channel array and (2) selective nanostructure coating, interaction, and modification of the nanopores. Distinctly variable nanostructures are chosen to provide a range of sensitivities for a given analyte using a concept complementary to that of hard and soft acid-base interactions (HSAB) and commensurate with a basis in dominant physisorption. The concept, based on the reversible interaction of hard acids and bases with soft bases and acids corresponds (1) to the inverse of the HSAB concept and (2) to the selection of sensor and analyte materials which do not result in strong covalent or ionic bonding but rather represent a strong HOMO-LUMO and additional molecular orbital mismatch. The technology implemented on "phase-matched" nanoporous silicon layers positioned on porous silicon micropores facilitates the application of nanostructured metals, metal oxides, and catalytic coatings, providing for notably higher sensitivities and selectivity. Materials which include electroless gold ($Au_xO$), tin ($SnO_2$), copper ($Cu_xO$), nickel (NiO), and nanoalumina provide for the detection of gases including $NH_3$, $PH_3$, CO, NO, $H_2S$, and $SO_2$ in an array-based format to the sub-ppm level. The value of this conductometric sensor technology results from a combination of (1) its sensitivity and short recovery time, (2) its operation at room temperature as well as at a single, readily accessible, temperature with an insensitivity to temperature drift, (3) its potential operation in a heat-sunk configuration allowing operation to a surface temperature of 80° C. even in highly elevated temperature environments (in sharp contrast to metal oxide sensors), (4) its ease of coating with a diversity of clearly mapped gas-selective materials form sensor arrays, (5) its low cost of fabrication and operation, (6) its low cost and ease of rejuvenation following contamination, and (7) its ability to rapidly assess false positives using FFT techniques, operating the sensor in a pulsed gas mode.

Introduction:

Because of the strongly interacting nature of nanostructures, arrayed configurations capable of highly distinct, predictable, and inexpensively calibrated responses for a prescribed set of analyte gases, at room temperature, would represent ideal devices for a diversity of applications. Efforts to form such devices utilizing a hybrid nanoporous/microporous silicon medium as the transduction site have produced individual gas sensors.[1-4] Here, we discuss a general approach to facilitate significant changes in sensor surface sensitivity for a variety of gases thus leading to the selective coating of these sensors to create, in combination, microfabricated arrays with integrated CMOS circuits. The general approach to a "materials selection table" is based on a concept complementary to that of hard and soft acid and base interactions (HSAB) first put forth by Pearson, et al.,[5] and later correlated within the context of Density Functional Theory (DFT) and Chemical Reaction Theory (CRT) by Pearson, Parr,[6,7] and their coworkers. Most recently this correlation of DFT and CRT has been further clarified by Cohen, Wasserman[8], and others.[9] The general approach to conductometric sensor development is commensurate with a basis in physisorption and has now been formulated to create highly variable surface interactions based upon a diversity of nanostructure modified coatings. The technology is implemented on "phase matched" nanoporous silicon layers positioned on porous silicon micropores which facilitate the application of nanostructured metals, metal oxides, and nanoparticle catalytic coatings, and provides for notably higher sensitivities and selectivity.

Development of the Sensor Platform:

Porous silicon (PS) micro/nanoporous interfaces, generated from "p-type" silicon, within themselves and after being transformed within the framework of nanotechnology offer the means to develop highly efficient nanostructure modified sensors. This is exemplified in FIG. 2.1.[2-4] FIG. 2.1(*a*) illustrates a close up side view of a hybrid porous silicon film. FIG. 2.1(*b*) illustrates a nanoparticle tin-oxide coating dispersed on the porous silicon micro/nanopores. FIG. 2.1(*c*) illustrates 10 to 30 nm $Au_xO$ nanostructure dispersed on the porous silicon micro/nanoporous surface. The select preparation of the nanopore coated micropore structure in FIG. 2.1(*a*) is detailed elsewhere[10] It is this etched PS structure which provides both for a combination of rapid Fickian diffusion[2(a)] into the readily observable micropores followed by limiting Knudsen diffusion[11] into the nanopore wall coating of the micropores. Select nanostructured metals, metal oxides, and nanoparticle catalytic coatings can be deposited on the "nanostructure phase matched" nanopore covered PS micropores, providing for distinct, variable, and notably higher sensitivities and selectivity. Metals which include electroless gold, tin, copper, and nickel as well as nano-alumina, magnesia, titania, and zirconia provide for the detection of gasses NO, $NO_2$, CO, $NH_3$, $PH_3$, $H_2S$, and HCl at the sub-ppm level.[2-4,10]

Results obtained with electroless tin and gold coatings[2,4] are presented in FIGS. 2.1(*b*) and (*c*), respectively. Here, the introduction of electroless tin produces an $SnO_x$ (x=1, 2) coating whereas the introduction of electroless gold results in the formation of the gold clustered oxide nanostructures, $Au_xO$ (FIG. 2.1(*c*)) positioned within the micropores.

The introduction of nanostructures to the micro/nanoporous PS framework selectively modifies the impedance response to considerably improve gas detection. In a set of initial experiments[2,4,12] we determined that the introduction of $SnO_x$ and $Au_xO$ nanostructures to the micro/nanoporous framework to produce the enhanced sensitivity for PS (FIG. 2.2) is considerably less than that for the nanostructured deposition illustrated in FIG. 2.1. FIG. 2.2 illustrates a comparison of the response measured initially for sensors that are untreated, treated with electroless gold, or treated with electroless tin, and tested with 30 repeat pulses of 20 ppm $NO_x$, $NH_3$, or CO. The average impedance change is given in FIG. 2.2.

The $SnO_x$ coated sensor, in particular, allows the room temperature detection of CO at the sub-ppm level considerably below that of other PS sensors.[13-15] This room temperature operational $SnO_x$ coated sensor should be compared with PS-based sensors whose resistances exceed hundreds of k$\Omega$ operating on a 2V bias,[13] $SnO_2$ sensors operating at 300° C.-500° C.,[14] and similar gas sensors operating at 2-5 V.[15] The sensitivity of these nanocoated tin oxide sensors exceeds that of other tin oxide sensors by at least an order of magnitude and at room temperature. Further, more recent electroless gold treatments of improved PS micro/nanoporous surfaces (for approximately 30 s) have lead to the substantial improvement in sensitivity (signal/nose) for ammonia presented in FIG. 2.3.[4] FIG. 2.3 illustrates the significantly improved sensitivity to ammonia vs. the average impedance changes given in FIG. 2.2. The experiments are run in an identical configuration.

We have now carried out an extensive study involving the sensing of phosphine for several nanostructure modified PS surfaces. These specific experiments, carried out in the manner already indicated,[2, 4, 10] will be discussed in more detail elsewhere[16] and are summarized in Table 1. The results which we have obtained for phosphine are exemplified for an $Au_xO$ nanostructure coated micro/nanoporous PS surface in FIG. 2.4[16]. FIG. 2.4 illustrates the improved $PH_3$ response to an electroless $Au_xO$ coating. Here, 1, 2, 3, 4, and 5 ppm of $PH_3$ is pulsed onto the sensor surface every 300 s. For the first 1800 s an $N_2$ purge is applied for resistance stabilization. FIG. 2.4 demonstrates that the impedance change for an $Au_xO$ nanostructure coated surface is close to five times that of the untreated surface. Table 1 also includes additional new data obtained for NO[16] with electroless copper, nickel, and gold treatments for $Cu^{+1,+2}$ and $Ni^{+2}$ oxides, and gold (0, +1) clustered oxide nanostructured coatings. These individual studies will also be discussed in more detail elsewhere.

The results we have obtained for several nanostructure modified PS surfaces for the gases $NH_3$, $PH_3$, and NO are summarized in Table 1 where the ratio of impedance changes are given for the various nanostructure coatings relative to the naked micro/nanoporous PS structure. In addition, the data obtained for CO, a weak base, demonstrates a significant response increase upon exposure of this gas to an $SnO_x$ (x is dominantly 2) (hard acid) nanostructure coated surface whereas the data obtained for $H_2S$ (intermediate base) indicates a significant increase in response for an $Au_xO$ nanostructured oxide (weak acid) coated surface.

TABLE 1

$\Delta R$(coating)/$\Delta R$(uncoated) values are shown for $PH_3$, NO, and $NH_3$ impedance changes.

| | Coating | | | |
|---|---|---|---|---|
| Test Gas | Tin ($SnO_2$) | Nickel (NiO) | Copper ($Cu_xO$) | Gold ($Au_xO$) |
| $PH_3$ | 2 | 2.5 | 4 | 5 |
| NO | 7-10 | 3.5 | 1 | 1.5 |
| $NH_3$ | 1.5 | (1.5-2) | (2-2.5) | ~3 |

Comparison is to an uncoated PS sensor. The nanostructured coatings deposited to the PS surface are indicated in the Table. Base resistance of the sensors used in these experiments varies from 300 to 500 $\Omega$. Further data points for CO, $PH_3$, and $H_2S$ are discussed in the text.

FIG. 2.2-2.4 and Table 1 suggest that the proper combination of nanocoating techniques can be used to produce combinations of array-based devices of varying sensitivity to a variety of gases and that this matrix of array responses can be used in tandem to selectivity analyze gas mixtures. For example, an array of an untreated, $SnO_x$ nanocoated, and gold clustered oxide coated sensors could be used to sensitively test for the presence and relative concentrations of ammonia and nitric oxide. This nanostructured $SnO_x/Au_xO$ sensor coating provides a basis for developing a sensitive room temperature detector that could be installed as a simple sensor system for asthmatics.[2]

It remains to assess whether an underlying principle dictates the behavior that we have observed. We suggest that such a principle exists and that it is possible to extend this technology[17] to additional gases with the development of a more general selective coating technology based on the extrapolation of the concepts of hard and soft acids and bases, (HSAB), developed by Pearson and others.[5-9] Here, by monitoring the trends in hard and soft acid and base behavior; first order selections can be made for the appropriate modification of the PS hybrid interface with nanostructured metal/metal oxide and catalytic coatings to create selectivity for a number of gases.[4(a),10(c),17] The development of selective nanostructured coatings that reversibly complex with a gas (physisorption) can be based on a selected combination of hard Lewis acids with soft Lewis bases and vice versa as well as with the trends associated with the classification of the hard and soft nature of these acids and bases.

Hard and Soft Acids and Bases (HSAB) as the Basis for the Construction of Nanostructured Sensor Surfaces:

The concept of chemical hardness/softness first developed by Pearson[5] has its basis in the nature of metal ion complexation in aqueous solution. It is a generalization of the Lewis acid/base concept. The HSAB concept, as it correlated with chemical reactivity theory (CRT), was given a deep foundation in density functional theory[7] by Parr and coworkers,[7] following an initial correlation with molecular properties established by Pearson and Parr.[6] More recently, conflicts underlying the correlation of the DFT and CRT theories have been largely resolved by Cohen and Wasserman[8] to obtain a further refinement of the concepts of electronegativity and hardness.

The properties of acids and bases can be described as hard and soft based upon the correlation of several atomic/molecular properties which include the ionization potential, I, the electron affinity, A, and the chemical potential, $\mu$, in concert also with the HOMO-LUMO gap concept from molecular orbital theory. A few examples of the groups of hard, borderline, and soft acids and bases are given in Table 2. Whereas for a soft acid, the acceptor atom is of low positive charge, of large size, and has polarizable outer electrons, in a hard acid, the acceptor atom is of small size and not easily polarized. In a soft base, in precise contrast to a hard base, the donor atom is of low electronegativity, easily oxidized, and highly polarizable, with low-lying empty molecular orbitals. The HSAB principle was initially based on empirical observations. Yet, as it groups acids and bases, a basis for it has been developed in terms of DFT and follows the principle that soft-soft combinations depend mainly on covalent bonding and hard-hard combinations depend mainly on ionic bonding. Further the HSAB principle states that hard acids prefer to coordinate to hard basis whereas soft acids prefer to coordinate to soft bases.

TABLE 2

Selective nanostructured coatings are based on the combination of hard acids and soft bases and vice versa, exemplified by the groupings indicated below.

| | Hard | Borderline | Soft |
|---|---|---|---|
| Acids | $H^+$, $Li^+$, $Na^+$, $K^+$ $Be^{2+}$, $Mg^{2+}$, $Ca^{2+}$ $Cr^{2+}$, $Cr^{3+}$, $Al^{3+}$ $SO_3$, $BF_3$, $Sn^{+4}$ | $Fe^{2+}$, $Co^{2+}$, $Ni^{2+}$ $Cu^{2+}$, $Zn^{2+}$, $Pb^{2+}$ $SO_2$, $BBr_3$, $Sn^{2+}$ | $Cu^+$, $Au^+$, $Ag^+$, $Tl^+$, $Hg^+$ $Pd_2^+$, $Cd_2^+$, $Pt_2^+$, $Hg_2^+$ $BH_3$ |
| Bases | $F^-$, $OH^-$, $H_2O$, $NH_3$ $CO_3^{2-}$, $NO_3^-$, $O_2$ | $NO_2$, $SO_3^{2-}$, Br $N_3^-$, $N_2$, $H_2S$ $C_6H_5N$, SCN | $H^-$, $R^-$, $CN^-$, CO, I $SCN^-$, $R_3P$, $C_6H_5$ $R_2S$ |

Within the HSAB-DFT framework, the electronic chemical potential,[6,7a,18]

$$\mu = (\partial E(N)/\partial N)_{v_e} = (\delta E/\delta \rho)_{v_e} \qquad (1)$$

is a global quantity, where E(N) is the ground state energy of a system of N electrons in the electrostatic potential energy, $v_e$, due to its nuclei (fixed). E is a functional (Eq. 1) of the electron density, $\rho$. The 3 point finite difference approximation for $\partial E(N)/\partial N$ gives $\mu \approx -(I+A)/2$ with I the ionization potential and A the electron affinity so that $\mu$ is the negative of the Mulliken electronegativity, $\omega_M$.

$$\chi_M \approx -\mu = (I+A)/2 \qquad (2)$$

The absolute hardness, $\eta$ of a species, is defined[6,19] as $$\eta = (\partial^2 E(N)/\partial N^2)_{v_e} = (\partial \mu/\partial N)_{v_e} \approx (I-A) \qquad (3)$$

and the absolute softness[20] is the inverse of the hardness $$S = \eta^{-1} \approx (\partial N/\partial \mu)_{v_e} \qquad (4)$$

The approximation in Eq. 3 arises from the finite difference formula.

Unlike the chemical potential, the hardness is not constrained to be constant everywhere throughout a system, having local values for which $\eta$ is simply a global average. Parr and coworkers[7] have defined a local hardness which corresponds to the change in chemical potential with electron density in different parts of a molecule, complex, or simply a system. Cohen and Wasserman,[8] in their formulation of CRT, define a generalization to include a hardness matrix that incorporates both the self-hardness of individual species and the mutual hardness for pairs of species combining in a system. They also provide a description of local softness as they demonstrate how the reactivity of a species depends on its chemical context. Within this context, as interacting constituents separate, the hardness matrix becomes diagonal in the self-hardness. Further, it is possible to establish a more general description of electronegativity (Eq. 2) equalization. Of equal importance are the correlations which define the connection between CRT and DFT theories as they can be used to provide a description of those molecular orbitals (MO's) involved in the process of electron transfer from an acid to a base.

Within the context that we have outlined, if two systems B and C are brought together, electrons will flow from the system of lower $\chi$ (Eq. 2) to that of higher $\chi$ to equilibrate the chemical potentials. If we consider that in solid-solid interactions, the equilibration of the Fermi levels is the analog of the chemical potential, it is not difficult to envision the extrapolation of these concepts to the interaction of a molecule with an interface.

Within the context of interacting molecular systems B and C, as a first approximation to an acid-base interaction, the fractional number of electrons transferred can be defined by[5]

$$\Delta N = (\chi_C - \chi_B)/2(\eta_C - \eta_B) \quad (5)$$

where the difference in electronegativity drives the electron transfer and the sum of the hardness parameters acts as a resistance. This expression, while approximate, is useful because it expresses the nature of the initial interaction between B and C using properties of the isolated systems as would provide the backdrop for the first order categorizations given in Table 1. Whereas the absolute chemical potential and hardness are molecular parameters, the flow of electrons is from a specific occupied molecular orbital of B to a specific empty orbital in C. Thus, the overlap between the exchanging orbitals will be critical in determining energy change and the nature of chemical interaction.

The correlation of hardness and softness with molecular orbital theory follows readily from the Frontier orbital concept of chemical reactivity theory.[22] Here, within the context of Koopman's theorem, the frontier orbital energies can be correlated with the expressions for chemical potential (Eq. 1, 2), hardness (Eq. 3), and softness (Eq. 4) as $$-\epsilon_{HOMO} = I, \quad -\epsilon_{LUMO} = A \quad (6)$$

where now the concept of hardness reduces to the statement: hard molecules have a large HOMO-LUMO gap and soft molecules have a small HOMO-LUMO gap.[5] Thus, the criteria that hard acids prefer to coordinate to hard bases and soft acids to soft bases is, in one sense, a HOMO-LUMO matching criteria. Alternatively, Politzer[23] has shown that the softness of atoms correlates with their polarizability.

In contrast to the driving force of the HSAB concept, to create sensitive, rapidly responding, and reversible porous silicon gas sensors, we wish to reverse the process described above commensurate with a basis in physisorption with minimal chemical interaction. This would suggest a result to which the data in Table 1 attest, that the general approach to conductometric chemical sensor development should follow the inverse of the HSAB concept of acid-base chemical interaction. The changes in response of the nanostructure modified porous silicon interfaces outlined in Table 1 can be correlated with this inverse behavior.

Interaction with Nanostructure Modified Porous Silicon Surfaces:

A first order comparison of the response date in Table 1 with the exemplary list of hard, borderline, and soft acids and bases in Table 2 clearly demonstrates that hard bases such as ammonia (and ~phosphine) respond most strongly (impedance change) when exposed to a nanostructured $Au_xO$ surface corresponding to a soft acid ($Au^{O, +1}$). In contrast, the soft bases CO (and NO) display a maximum response (change in resistance) upon interaction with the borderline to hard acid $SnO_x$ ($Sn^{+2, +4}$). Note also (FIG. 2.1) the minimum response of the untreated PS surface to CO and the subsequent decrease for an $Au_xO$ nanostructure treated surface. This decrease in an already small if negligible impedance response is consistent with the impedance change expected for the interaction of a weak acid with a weak base.

The responses outlined in Table 1 and FIG. 2.2-2.4 in concert with Table 2 can be correlated further to generate the materials positioning Table 3, FIG. 2.6. Here, based exclusively on the relative responses of the gases we have studied with several nanostructured coatings, we position the five bases $NH_3$, $PH_3$, $H_2S$, NO, and CO relative to the porous silicon ($Si^{+1 \ to \ +4}$) and the PS modified acidic interfaces generated with a nanostructured $SnO_x$ ($Sn^{+2, +4}$), $Al_2O_3$ ($Al^{+3}$), NiO ($Ni^{+2}$), $Cu_xO$ ($Cu^{+1, +2}$), and $Au_xO$ ($Au^{0, +1}$) coating. The basis for this table is the correlation of relative responses or impedance changes summarized in FIG. 2.2-2.4 and Table 1. Note, however, that we are correlating the interaction of gaseous bases with nanostructured surfaces. The location of each of these bases is thus evaluated based upon their observed interactions with the range of treated PS surfaces. The data in Table 1 certainly suggests that a general approach to conductometric (PS) sensor development should have as its driving force the combination of a weakly acidic sensor surface with a strongly basic interacting molecule or vice-versa. (Similar comments would apply to a strongly or weakly basic surface). Within the framework of molecular orbital theory, we attempt to find a mismatch between the HOMO-LUMO gaps associated with the gaseous base and surface acid orbitals. This mismatch is as it should be to produce rapidly responding, "reversible," sensor configurations, minimizing either strong covalent or strong ionic bonding.

With a focus to sensor array development, the data in Table 1, when correlated with the exemplary information reflected in Table 2, would appear to suggest the "finer" materials positioning indicated in Table 3 in FIG. 2.6 within especially similar molecular analogs. We have constructed Table 3 in FIG. 2.6 within the framework of Table 2 considering, to first order, the hard acid strength which we associate with an $Sn^{+4}$ ($SnO_2$) configuration, the soft acid strength to be associated with an $Au^{0,+1}$ ($Au_xO$) configuration, and the intermediate (borderline) acid strength we associate with the porous silicon hybrid surface, where the silicon oxidation state ($Si_xO_y$) can vary from +1 to +4[24]. Superimposed relative to this structure, we consider the locations of intermediate $Ni^{+2}$, soft and intermediate $Cu^{+1,+2}$, and the comparatively strong acid state with which we associate $Al^{+3}$ ($Al_2O_3$).

A larger impedance change associated with $SnO_x$ suggests that ammonia lies closer to porous silicon than to the extremely strong $Sn^{+4}$ acid site. The inherently hard basic character of ammonia is also consistent with the strong impedance change observed for the $Au_xO$ nanostructure coated surface. The behavior of ammonia is also strongly mimicked by phosphine which displays an expected and strong increasing impedance change relative to PS associated with $Cu_xO$ and $Au_xO$ nanostructure modified surfaces. The expected decrease in impedance response as a result of a ($Ni^{+2}$) oxide nanostructure coating, as it exceeds that of the PS structure, suggests that it lies to the soft acid side of the untreated hybrid PS surface, however, lying in close proximity. Thus, the broad nature of the $Ni^{+2}$ and hybrid PS regions indicated in the Table. The response to the hybrid structure and an "$Al_2O_3$" nanostructure treated surface appear virtually identical. Therefore, we anticipate that phosphine lies equally close to $Al_2O_3$ and PS with $NH_3$, a harder base, on the hard base side of $PH_3$. This also suggests that the acid character of $Sn^{+4}$ is considerably harder than that of $Al^{+3}$.

The NO radical has a considerably different molecular orbital makeup and electron shell structure than ammonia or phosphine as it represents a weak base. The open shell nature of NO would suggest a very different interaction with the hybrid PS and nanostructure treated PS surfaces. However, not surprisingly, the soft base-hard acid interaction of NO with an $SnO_2$ nanostructured coating leads to a substantial impedance change relative to PS. This signals the reversible interaction of a hard acid with a soft base. Further, the response to gold, copper, and nickel treated surfaces, while considerably muted relative to a tin treated surface, suggests that NO should be positioned directly below the copper ($Cu^{+1,+2}$) systems and intermediate to gold ($Au^{0,+1}$) and nickel ($Ni^{+2}$). The interaction with $Ni^{+2}$ suggests a greater separation from nickel than gold. Further, while PS and $Ni^{+2}$ may lie in a similar intermediate region, the larger impedance change observed with a $Ni^{+2}$ surface suggests that $Ni^{+2}$ lies to the hard acid side of PS acting as a harder acid coating on the PS surface. Hence the broader nature of the $Ni^{+2}$ and PS regions indicated in Table 3 in FIG. 2.6.

Discussion:

A general approach to facilitate significant and predictable changes in sensor surface sensitivity for a variety of gases has been formulated based on a complementary theory to the well known concept of hard and soft acid and base interactions by Pearson and others.[5-9] We suggest that nanostructured sensor surfaces for conductometric array-based devices be constructed from a finders table by first establishing whether the gas to be detected classifies as a hard or soft acid or base and subsequently developing a range of nanostructured coatings which encompass as wide a range of acidity and basicity as possible so as to create an array of responses. In addition, the correlation with trends in the proton affinity (PA), essentially the gas phase basicity, of those gases considered in Table 3 in FIG. 2.6 and the previous discussion also bears serious consideration.[25] However, as an overriding principle, the maximum response (impedance change) is to be expected from combinations of hard acids with soft bases and vice versa. While there are other factors, including steric effects, polarization[23], and the nature of the open or closed shell character of interacting molecules to consider, we suggest that the acid/base makeup of the nanostructure modified PS sensor surface and the mismatch of the hard and soft acid/base character of the species to be detected is the primary driving forces for creating an efficient detector. The conductometric sensors, which we formulate using the conceptual modification of the HSAB principle which we present, are simply designed and can operate with less than 1 mW of power, being potentially sensitive as well as selective to a wide variety of gases while operated at room temperature. These rapidly ($\leq 2$ s) and reversibly responding devices, with an inherent low voltage and lower power,[2,4,10] can be readily integrated with CMOS electronics into arrays of sensors.

The value of the conductometric porous silicon sensor platform, for which we can now generate a "materials selection table"[17] to create arrayed devices, results from a combination of (1) its sensitivity and short recovery time, (2) its operation at room temperature as well as at a single, readily accessible, temperature with an insensitivity to temperature drift, (3) its potential operation in a heat-sunk configuration, allowing operation to a surface temperature of 80° C. even in high elevated temperature environments (in sharp contract to metal oxide sensors), (4) its ease of coating with diversity of clearly mapped gas-selective materials for form sensor arrays, (5) its low cost of fabrication and operation, (6) its low cost and ease of rejuvenation following contamination, and (7) its ability to rapidly assess false positives using FFT techniques, as we operate the sensor in a pulsed gas mode.[26]

An important problem which plagues chemical sensors is the potential contamination of the sensor surface and the elimination of the sensor response over a long period of time. We have managed to treat sensors which have stopped responding for over one year as we rejuvenate their response[4] (a). The ammonia response of such a sensor to 1, 2, 3, 4, and 5 ppm of ammonia before and after the rejuvenation process is shown in FIG. 2.5. FIG. 2.5 illustrates the response to $NH_3$ after a sensor is subjected to a rejuvenation process. The recovery of the sensor is clearly indicated.

Ex. 1 References, each of which is incorporated herein by reference:

1) Seals L, Tse L A, Hesketh P J, Gole J L. Rapid, reversible, sensitive porous silicon gas sensor. J Appl Phys 2002; 91:2519-2523.
2) (a) Lewis S, DeBoer J, Gole J L, Hesketh P. Sensitive, selective, and analytical improvements to a porous silicon gas sensor. Sens Actuators B: Chem 2005; 110; 54-65. (b) Gole J L, Lewis 5, Lee S, Nanostructures and porous silicon: activity at interfaces in sensors and photocatalytic reactors. Phys Stat Sol A 2007; 204: 1417-22 and references therein.
3) Gole J L. Photoluminescence induced metallization for low resistance contacts. Tech Adv. Invited, MRS Bulletin 2003; 28:263.
4) (a) Ozdemir S, Gole J L. Porous silicon gas sensors for room temperature detection of ammonia and phosphine. Chem Sens 8: Chem (Gas, Ion, Bio) Sens and Analytical Systems, ECS Transactions. 2008; 16(11):379-387. (b) Gole J L, Corno J, Ozdemir S, Prokes S, Shin H-C. Phys Stat Solid, in press.
5) See for example
   a) Pearson R G. Hard and soft acids and bases—the evolution of a chemical concept. Coordin Chem Rev 1990; 100:403-25. See also
   b) Pearson R G. Hard and soft acids and bases. J Am Chem Soc 1963; 85:3533-3539.
   c) Pearson R G Chemical hardness. 1997; Weinheim: John Wiley VCH.
   d) Pearson R G. Chemical hardness and density functional theory. J Chem Sci 2005; 117(5):369-377.
   e) Pearson R G. Absolute electronegativity and hardness: application to inorganic chemistry. Inorg Chem 1988; 27:734-740.
6) Parr R G, Pearson R G. Absolute hardness: companion parameter to absolute electronegativity. J Am Chem Soc 1983; 105:7512-7516.
7) (a) Parr R G, Yang W. Density functional theory of atoms and molecules. 1989; Oxford University Press: New York. (b) Geerlings P, De Proft F, Langenaeker W. Chem Rev 2003; 103:1793.
8) Cohen M H, Wasserman A. J Phys Chem 2007; 111:2229-2242.
9) Zhan C G, Nichols J A, Dixon D A. Ionization potential, electron affinity, electronegativity, hardness, and electron 10) (a) Gole J L, Lewis S E. Nanostructure and morphology modified porous silicon sensors. Quantum Sensing and Nanophotonic Devices—Nanostructures in Silicon, SPIE-Proceedings 2005; 5732:573-583. (b) Gole J L, Lewis, SE, Fedorov A, Prokes S. Nanostructures and porous silicon: activity and phase transformation in sensors and photocatalytic reactors. Physical Chemistry of Interfaces and Nanomaterials IV, SPIE-Proceedings 2005; 1-12:5929-08. (c) Ozdemir S, Gole J L. The potential of porous silicon gas sensors. Current Opinions in Solid State and Materials Science 2008; 11:92-100.
11) Kottke P A, Fedorov A G, Gole J L. Multiscale mass transport in porous silicon gas sensors. Modern Aspects of Electrochemistry, M. Schlesinger editor, Springer, 2008; 43:139-168.
12) Gole J L, Fedorov A G, Hesketh P, Burda C. From nanostructures to porous silicon: sensors and photocatalytic reactors. Phys. Stat Sol (C) 2004; 1(S2):S188-197.
13) Foucaran A, Pascalk-Delannoy F, Giani A, Sackda A, Commette P, Boyer A. Porous silicon layers used for gas sensor applications. Thin Sol Films 1997; 297:317.
14) Moseley P T. Solid state gas sensors. Meas Sci Technol 1997; 8:223.
15) Schechter I, Ben-Chorin M, Kuz A. Sensitive, selective and tunable nanostructure modified porous silicon gas sensor. Anal Chem 1995; 67:3727.
16) Ozdemir S, Gole J L. Work in preparation.
17) Gole J L. A general approach to creating selective metal coatings at a nano-microporous porous silicon interface for sensor applications. 2006a; Continuation in part; patent Applied for.
18) Parr R G, Donnelly R A, Levy M, Palke W E. J Chem Phys 1978; 68:3801.
19) Parr R G, Pearson R G. J Am Chem Soc 1983; 105:7512.
20) Yang W, Parr R G, Proc Natl Acad Sci USA 1985; 82:6723.
21) (a) Yang W, Parr R G, Pucci R. J Chem Phys 1984; 81:2862. (b) Parr R G, Yang W. J Am Chem Soc 1984; 106:4049.
22) Fukui K, Yonezawa T, Shingu H. J Chem Phys 1952; 20:722.
23) Politzer P. Relationship between the charge capacity and the hardness of neutral atoms in group. J Chem Phys 1987; 86: 1072.
24) Gole J L, White M G, Wang T-H, Watkins C, Street S C, Dixon D A, The surprising oxidation state of fumed silica and the nature of water binding to silicon oxides and hydroxides. Submitted.
25) Dixon D A. Private communication. See J L Gole and D A Dixon to be published
26). Lewis S E, DeBoer J R, Gole J L. A pulsed system frequency analysis for device characterization and experimental design. Sens Actuator B: Chem 207; 122:20-29.

Example 2

Brief Introduction to Ex. 2

Porous silicon surface modification methods have been employed for detecting different gas molecules; including $H_2O$, ethanol, methanol, isopropanol, $CO_x$, $NO_x$, $NH_3$, $O_2$, $H_2$, HCl, $SO_2$, $H_2S$ and $PH_3$.

Introduction:

Porous silicon (PS) has drawn considerable attention for sensor applications. Its luminescence properties, large surface area, and compatibility with silicon based technologies have been the driving force for this technology development. Recently biochemical [1-3], microfluidic flow [4], temperature and pressure [5], magnetic [6-7], chemical ion [8] and gas sensors have been reported. Chemical functionalization of the large surface areas, which can be generated in PS, shows the potential for developing a variety of gas sensors. Humidity [9-14], organic solvents [15-23], $CO_x$, $NO_x$ [27-32], $NH_3$, $O_2$ [27], $H_2$ [24-26], HCl, $SO_2$, $H_2S$, and $PH_3$ have all been detected. In this Example, following a recent publication [*9] in which this work is summarized, we discuss our current gas sensor design and note the capabilities of other porous silicon gas sensors.

Nanopore covered microporous PS interfaces have been formed to provide an active scaffolding for the creation of sensor [33,*34] and microreactor [*34, 35] configurations. Rapidly responding (≤2 s), reversible, and sensitive (≤2 ppm) PS gas sensors (PSGS), operating at room temperature, and based on a uniquely formed highly efficient electrical contract to the nanopore covered microporous array, are transformed on the basis of a general theory for surface modification by introducing active nanoparticles to establish gas selectivity (FIG. 2.1 of Example 1). FIG. 2.1a illustrates a close up side view of a hybrid porous silicon film. FIG. 2.1b illustrates a nanoparticle tin-oxide coating dispersed on porous silicon micro/nanopores. FIG. 2.1c illustrates 10 to 30 nm $Au_xO$ nanosructures dispersed on the on porous silicon surface.

Given the proper preparation of the nanopore coated micropore structure, subsequent treatments with HCl can provide a significant enhancement of the UV light induced photoluminescence (PL) emission from these surfaces [33, *36,37]. Combination of PL induced metallization and electron beam deposition is used to form a unique low-resistance contact to PS. Sensing of HCl, $NH_3$, CO, $NO_x$, $SO_2$, $H_2S$, and $PH_3$ at or below the ppm level at bias voltages as low as 100 mV and contact resistances as low as 20Ω [*36] has been accomplished [33]. However, the distinguishing feature of this PSGS which is more typically operated in the 1-3 V range is the ability to incorporate not only high sensitivity and selectivity but also the ability to respond rapidly and accurately over a broad range of environmental temperature, pressure, and humidity. With an extremely low power requirement (watch battery) this PSGS sensor provides a combination of high sensitivity (ppb range) and room temperature operation that typical gas sensors do not offer. Furthermore, the sensor shows the potential for operation in elevated temperature combustion environments. Within a framework that is readily amenable to integration into standard CMOS/MEMS technology, novel surface coatings form the basis for operation of sensor arrays operating in concert or employing a divided gas flow in multiple gas environments. This combination, with ready replacement and sensor rejuvenation, can simplify a potentially complex and costly detection process.

A general approach to facilitate significant changes in sensor surface sensitivity for a variety of gases, based on a complementary theory to the well known concept of strong and weak acid and base interactions by Pearson and others [38] and commensurate with several established gas-surface interactions [39, 40], has now been formulated [41] to create selective surface coatings. The technology as implemented [33, 41] on 'phase matching' nanoporous silicon layers positioned on porous silicon micropores facilitates the application of nanostructured metals, metal oxides, and nanoparticle catalytic coatings, providing for notably higher sensitivities. Within this framework, novel signal filtering techniques [33, *42], operative in a pulsed gas environment, are introduced as a means to reliably eliminate false positive signals. A PS nanostructure coated microstructured hybrid configuration when coated with tin oxide ($NO_x$, CO) and gold nanostructures ($NH_3$) provides a greatly increased sensitivity to the indicated gases (FIG. 2.2). FIG. 2.2 illustrates a comparison of response for sensors that are untreated with electroless gold, or treated with electroless tin, and tested with 30 repeat pulses of 20 ppm $NO_x$, $NH_3$, or CO. Their average impedance change is given.

Sensing of $NH_3$ and $NO_x$ for asthmatics and the HCl, $PH_3$, and formaldehyde products of methamphetamine is possible at or below the 100 ppb level. The introduction of gold and tin-based nanostructures to the micro/nanoporous PS framework, through electroless metal treatments, selectively modifies the impedance response to considerably improve the detection of $NH_3$, CO, and $NO_x$ (FIG. 2.2) [38]. The introduction of $SnO_2$ and $Au_xO$ nanostructures to the micro/nanoporous framework to produce the enhanced sensitivity for PS (FIG. 2.2) is considerably less than that for the nanostructured deposition illustrated in FIG. 2.1. The $SnO_x$ coated sensor, in particular, allows the room temperature detection of CO at the ppm level considerably below that of other PS sensors [43-45]. This $SnO_2$ coated sensor should be compared with PS-based sensors whose resistances exceed hundreds of kΩ operating on a 2V bias [43], $SnO_2$ sensors operating at 300° C.-500° C. [44], and similar gas sensors operating at 2-5 V [45]. The sensitivity of these nanocoated tin oxide sensors exceeds that of other tin oxide sensors by at least an order of magnitude and at room temperature. Further, more recent electroless Au treatments of the surface for about 30 s have lead to the improvement in sensitivity for ammonia indicated in FIG. 2.3. Recent results for phosphine indicate detection levels much less than 1 ppm. FIG. 2.3 illustrates the significantly improved sensitivity to ammonia vs. the impedance response given in FIG. 2.2. These new results have been obtained with applied voltages of 3V after further electroless Au treatment of the surface for about 30 s.

FIGS. 2.2 and 2.3 suggest that the proper combination of nanocoating techniques can be used to produce combinations of array-based devices of varying sensitivity to a variety of gases and that this matrix of array responses can be used in tandem to selectivity analyze gas mixtures. For example, an array of an untreated $SnO_2$ nanocoated, and gold clustered oxide sensors could be used to sensitively test for the presence and relative concentrations of ammonia and nitric oxide [33]. A nanostructured tin oxide sensor coating provides a basis for developing a very sensitive room temperature nitric oxide detector that could be installed in a simple sensor system for asthmatics [33]. The outlined nanocoatings are formed using electroless metal solutions [46], however, there are several additional complimentary modes that might be used to produce gas selective nanocoatings on the nano/micropores of PS. These include short-term electron beam deposition and direct nanoparticle diffusion into the PS micropores so as to promote the required interaction with the nanopore covered PS micropores. An extension to the detection of several methamphetamine manufacture by-produces including $PH_3$ [47], acetone [48], and benzene [49] (in addition to $NH_3$ [33, 37] and HCl [33, 37]) can be made possible using specially designed aluminum oxide (e-beam) or aluminosilicate nanostructured surfaces [47], nickel (electroless) or zirconium oxide based (nanostructured $ZrO_2$ nanoshells [50] deposited into the micropores of PS) nanostructured surfaces [48], and nitrided titanium dioxide [49] ($TiO_{2-x}N_x$ [51, 52]) nanostructure coatings.

It is possible to extend the technology to a more expanded list of gases with the development of a more general selective coating technology based on the extrapolation of the concepts of hard and soft acids and bases set forth in the literature by R. G. Pearson and others [41]. By monitoring the trends in hard and soft acid and base behavior, first order selections for appropriate modifications of the PS hybrid interface with nanostructured metal/metal oxide coatings to create selectivity for a number of gases can be made. The development of selective nanostructured coatings that reversibly complex with a gas can be based on the combination of hard Lewis acids with soft Lewis bases and on the trends associated with the classification of the hard and soft nature of these acids and bases.

Through the introduction of gas pulsing techniques and frequency analysis, the linear low pressure gas response of the PS sensor can be separated from the effects of pressure, temperature, and humidity, and acquired, and filtered on a drifting baseline, further increasing sensitivity. FIG. 3.1 illustrates a gas sensor response to pulsing of ammonia between 0 and 5 ppm (in research grade nitrogen). FIG. 3.1 depicts a test in which the concentration of ammonia (in $N_2$) being delivered to the sensor was pulsed between 0 and 5 ppm at a frequency of 1/60 s (0.017 Hz) [33]. The baseline for the device increases during the test as the adsorption and desorption of ammonia equilibrate, however, the baseline can also be affected by low frequency changes in temperature and pressure. By introducing an Fast Fourier Transform (FFT) analysis to the rapidly reversible, linearly responding, PS gas sensor, the gas response can now be acquired and filtered on a drifting baseline or in the presence of external noise sources (FIG. 3.1). FIG. 3.2 illustrates a Fast Fourier Transform of PS gas response (a) before filtering and (b) after filtering.

This measurement technique further increases device performance by allowing (1) the signal strength to be empirically calculated at a known frequency (0.017 Hz in this case) and (2) the noise sources to be characterized and isolated [*42].

The FFT technique was developed and implemented to characterize weakly responding sensors. However, this data analysis method for the PS gas sensor also offers the ability to operate below saturation and provides several safeguards against false positive identification. The FFT module filters erroneous signals associated with the PS sensor. If the false positive is associated with the delivered gas, attributes of the "time-delay" module become unstable and the dataset is withdrawn [*42]. These sensors can be operated for mixed gas identifications and configured into array formats.

A linear response for the sensors provides both rapid detection of and quick recovery from the presence of the gas. This means that rather than waiting for the response to saturate (which would take several minutes) before a measurement is taken, for an unsaturated response (FIG. 3.1) the slope of the sensor's rising resistance can be monitored in seconds and that this PSGS can operate with only minor degradation for months of continual testing.

The ready rejuvenation of a severely poisoned sensor is also feasible and cost effective. FIG. 2.5 demonstrates the signal obtained from a sensor which was heavily contaminated and rendered completely insensitive for over a one year period.

Based on the formation of low resistance contacts to the PS interface, the sensor suites can be extended to develop microreactors in which visible light absorbing quantum dot (QD) photocatalysts are placed within the pores of PS and excited using PS electroluminescence or photoluminescence. Properly employed these microreactors might then be used to form 'solar pumped' sensors [34,37]. This is exemplified by the highly efficient light absorbing titania-based nanocolloids, produced in a nanoscale exclusive synthesis at room temperature, that can be nitrided in seconds to provide nitrogen doped [51,52], stable and environmentally benign $TiO_{2-x}N_x$ photocatalysts. whose optical response can be tuned across the entire visible region [51,52]. Tunability throughout the visible is found to depend upon the degree of nanoparticle agglomeration and upon the ready ability to seed the nanoparticles with metals (metal ions) including Pd and additional active dopants.

Films constructed from colloidal solutions of $TiO_{2-x}N_x$ and $Pd—TiO_{2-x}N_x$ on a quartz surface have been found to be photocatalytically active for the total oxidation of ethylene to carbon dioxide under UV and incandescent light illumination at room temperature [52]. These results provide strong evidence that novel materials which can be synthesized at room temperature can be conveniently used to coat the PS surface to produce, under visible light illumination, strongly oxidizing photocatalytic centers. The strategy of such an effort should be to generate uniquely optimized photocatalytic films by modifying the nature of those centers that produce the photocatalytic activity. FIG. 3.3 indicates an effort toward this goal as $TiO_2$ and $TiO_{2-x}N_x$ nanoparticles have now been deposited onto the PS framework. This effort has yielded about 60% coverage at the present time and shows considerable promise [*34]. FIG. 3.3a illustrates a close up top view of a hybrid porous silicon films. FIG. 3.3b illustrates 100-200 nm $TiO_2$ nanoparticles coating the porous silicon micropores. FIG. 3.3c illustrates 10 nm $TiO_{2-x}N_x$ nanoparticles coating (60%) the porous silicon micropores.

The value of the PS gas sensor technology we have summarized results from a combination of (1) its sensitivity and short recovery time, (2) its operation at room temperature as well as at a single, readily accessible, temperature with an insensitivity to temperature drift, (3) its potential operation in a heat-sunk configuration allowing operation to a surface temperature of 80° C. even in highly elevated temperature environments (in sharp contrast to metal oxide sensors), (4) its ease of coating with diversity of gas-selective materials to form sensor arrays, (5) its low cost of fabrication, (6) its low cost and ease of rejuvenation after contamination, (7) its low cost of operation, and (8) its ability to rapidly assess false positives by operating the sensor in a pulsed gas mode.

Conclusion:

Porous silicon (PS) has gained considerable interest in the past two decades. Gas sensors have represented one of the important applications of PS. A large surface area and the relative ease of modification of this surface has evolved a variety of sensor configurations. Sensitivity and selectivity changes have been observed as $Au_xO$, Pd, $TiO_2$, $TiO_{2-x}N_x$ and $SnO_2$ are placed on the PS surface. Organic vapors, $H_2O$, $CO_x$, $NO_x$, $NH_3$, $O_2$, $H_2$, HCl, $SO_2$, $H_2S$, and $PH_3$ have been detected. We found that a model paralleling the hardness of Lewis acids and bases can be used to guide surface coatings which interact selectivity with various molecules. The results presented show that PS can be utilized as a promising gas sensor as the PS surface modification is better understood.

Ex. 2 References, each of which is incorporated herein by reference:

[1] Francia D G, Ferrara L V, Manzo S, Chiavarini S. Towards a label free optical porous silicon DNA sensor. Biosense Bioelectron 2005; 21:661-5.

[2] Rendina I, Rea I, Rotiroti L, Stefano D L. Porous silicon-based optical biosensors and biochips. Physica E 2007; 38:188-92.

[3] Benilov A, Cabrera M, Skryshevsky V, Martin J R. Porous silicon localization for implementation in matrix biosensors. Mat Sci Eng B—Solid 2007; 139:221-5.

[4] Pagonis D N, Petropoulos A, Kaltsas G, Nassiopoulou A G, Tserepi A. Novel microfluidic flow sensor based on a microchannel capped by porous silicon. Phys Stat Sol A 2007; 204:1474-9.

[5] Pramanik C, Saha H, Gangopadhyay U. An integrated pressure and temperature sensor based on nanocrystalline porous silicon. J Micromech Microeng 2006; 16:1340-8.

[6] Granitzer P, Rumpf K, Krenn H. Ferromagnetic nanostructures incorporated in quasi-one-dimensional porous silicon channels suitable for magnetic sensor applications. J Nanomaterials 2006; 2006:1-7.

[7] Belkacem W, Mliki N, Belhi R, Saikaly, Yangui. Nanostructures cobalt on porous silicon substrate: structure and magnetic behaviour. Phys Stat Sol A 2007; 204:3321-32.

[8] Mery E. Alekseev S A, Zaitsev V N, Barbier D. Covalent grafting ion-exchange groups on porous silicon for Microsystems applications. Sens Actuators B: Chem 2007; 126: 120-5.

[*9] Gole J L, Lewis E L. Porous silicon-sensors and future applications. In: Kumar V, editor, Nanosilicon, Elsevier, 2007:149-75.

[10] Björkqvist M, Salonen J, Paski J, Laine E. Characterization of thermally carbonized porous silicon humidity sensor. Sens Actuators A: Phys 2004; 112:244-7.

[11] Rittersma Z M, Splinter S, Bödecker, Bnecke W. A novel surface-micromachined capacitive porous silicon humidity sensor. Sens Actuators B: Chem 2000; 68:210-7.

[12] Foucaran A, Sorli B, Garcia M, Pascal-Delannoy F, Giani A, Boyer A. Porous silicon layer coupled with thermoelectric cooler: a humidity sensor. Sens Actuators A: Phys 2000; 79:189-93.

[13] Björkqvist M, Salonen J, Laine E, Niinistö L. Comparison of stabilizing treatments on porous silicon sensor applications. Phys Stat Sol A 2000; 182:123-6.

[*14] Björkqvist M, Paski J, Salonen J, Lehto V, Studies on the hysteresis reduction in thermally carbonized porous silicon humidity sensor. IEEE Sense J 2007; 6:542-7.

[15] Salgado G G, Becerril D T, Santiesteban J H, Andres E R. Porous silicon organic vapor sensors. Opt Mater 2006; 29:51-5.

[16] Barillaro G, Diligenti A, Marola G, Strambini L M. A silicon crystalline resistor with an adsorbing porous layer as gas sensor. Sens Actuators B: Chem 2005; 105:278-82.

[17] Iraji zad A, Rahimi F, Chavoshi M, Ahadian M M. Characterization of porous poly-silicon as a gas sensor. Sens Actuators B: Chem 2004; 100:341-6.

[*18] Archer M, Christophersen M, Fauchet P M. Electrical porous silicon chemical sensor for detection of organic solvents. Sens Actuators B: Chem 2005; 106:347-57.

[19] Dorvee J, Sailor M J. A low-power sensor for volatile organic compounds based on porous silicon photonic crystals. Phys Stat Sol A 2005; 202:1619-23.

[**20] King H B, Ruminski A M, Snyder J L, Sailor M J. Optical-fiber-mounted porous silicon photonic crystals for sensing organic vapor breakthrough in activated carbon. Adv Mater 2007; 19:4530-4.

[21] Rocchia M, Rossi A M, Zeppa G. Determination of ethanol content in wine through a porous silicon oxide microcavity. Sens Actuators B: Chem 2007; 123:89-93.

[22] Stefano L D, Alfieri D, Rea I, Rotiroti L, Malecki K, Moretti L, Corte F G D, Rendina I. An integrated pressure-driven microsystem based on porous silicon for optical monitoring of gaseous and liquid substances. Phys Stat Sol A 2007; 204:1459-63.

[23] Vrkoslav V, Jelinek I, Trojan T, Jindrich J. Dian J. Porous silicon with β-cyclodextrin modified surface photoluminescence sensing of organic molecules in gas and liquid phase. Physica E 2007; 38:200-4.

[*24] Rahimi F, Iraji zad A, Razi F. Characterization of porous poly-silicon impregnated with Pd as a hydrogen sensor. J Phys D: Appl Phys 2005; 38:36-40.

[25] Rahimi F, Iraji zad A. Characterization of Pd nanoparticle dispersed over porous silicon as a hydrogen sensor. J Phys D: Appl Phys 2007; 40:7201-9.

[26] Arakelyan V M, Galstyan V E, Martirosyan K S, Shahnazaryan G E, Aroutiounian V M, Soukiassian P G. Hydrogen sensitive gas sensor based on porous silicon/$TiO_2$, structure. Physica E 2007; 38:219-221.

[27] Boarino L, Baratto C, Geobaldo F, Amato G, Comini E, Rossi A M, Faglia G, Lerondel G, Sberveglieri G. $NO_2$ monitoring at room temperature by a porous silicon sensor. Mat Sci Eng B—Solid 2000; 69-70:

[28] Baratto C, Faglia G, Comini E, Sberveglieri G, Taroni A, Ferrara V L, Quercia L, Francia G D. A novel porous silicon sensor for detection of sub-ppm $NO_2$ concentrations. Sens Actuators B: Chem 2001; 77:62-6.

[**29] Massera E, Nasti I, Quercia L, Rea I, Francia G D. Improvement of stability and recovery time in porous-silicon based $NO_2$ sensor. Sens Actuators B: Chem 2004; 102:195-7.

[30] Pancheri L, Oton C J, Gaburro Z, Soncini G, Pavesi L. Very sensitive porous silicon $NO_2$ sensor. Sens Actuators B: Chem 2003; 89:237-9.

[31] Chakane S, Gokarna A, Bhoraskar S V. Metallophthalocyanine coated porous silicon gas sensor selective to $NO_2$. Sens Actuators B: Chem 2003; 92:1-5.

[32] Subramanian N S, Sabaapathy V, Vickraman, Kumar G V, Sriram R, Santhi B. Investigations on Pd:$SnO_2$/porous silicon structures for sensing LPG and $NO_2$ gas. Ionics 2007; 13:323-8.

[33] Lewis S, DeBoer J, Gole J L, Hesketh P. Sensitive, selective, and analytical improvements to a porous silicon gas sensor. Sens Actuators B: Chem 2005; 110:54-65.

[*34] Gole J L, Lewis S, Lee S, Nanostructures and porous silicon: activity at interfaces in sensors and photocatalytic reactors. Phys Stat Sol A 2007; 204:1417-22 and references therein.

[35] Gole J L, Fedorov A, Hesketh P, Burda C. From nanostructures to porous silicon: sensors and photocatalytic reactors. Phys Stat Sol C 2004; 1:188-97.

[36a] Gole J L, Seals L T, Lillehei P T. Patterned metallization of porous silicon from electroless solution for direct electrical contact. J Electrochem Soc 2000; 147:3785-9.

[*36b] Gole J L, Seals L T, DeVincentis J A, Lillhei P T, Prokes S M, Dixon D A. Chloride salt enhancement and stabilization of the photoluminescence for a porous silicon surface. Phys Rev B 2000; 61:5615.

[36c] Gole J L. Photoluminescence induced metallization for low resistance contacts. Tech Adv, Invited, MRS Bulletin 2003; 28:263.

[37] Seals L, Tse L A, Hesketh P J, Gole J L. Rapid, reversible, sensitive porous silicon gas sensor. J Appl Phys 2002; 91:2519-2523.

[38] Pearson R G. Hard and soft acids and bases—the evolution of a chemical concept. Coordin Chem Rev 1990; 100:403-25.

[39] Albert K J, Lewis N S, Shauer C L, Sotzing G A, Sitizel S E, Vaid T P, Walt D A. Cross-reactive chemical sensor arrays. Chem Rev 2000; 100:2595-2626.

[40] Kwon C W, Poquet A, Mornet S, Campet G, Deliville M H, Treguer M, Portier J. Electronegativity and chemical hardness: two helpful concepts for understanding oxide nanochemistry. Mater Lett 2001; 51:402-403.

[41] Gole J L. A General Approach to Creating Selective Metal Coatings at a Nano-microporous Porous Silicon Interface for Sensor Applications. Continuation in part; patent Applied for, (2006a).

[*42] Lewis S E, DeBoer J R, Gole J L. A pulsed system frequency analysis for device characterization and experimental design. Sensor Actuator B: Chem 2007; 122:20-29.

[43] Foucaran A, Pascalk-Delannoy F, Giani A, Sackda A, Comette P, Boyer A. Porous silicon layers used for gas sensor applications. Thin Sol Films 1997; 297:317.

[44] Moseley P T. Solid State Gas Sensors. Meas Sci Technol 1997; 8:223.

[45] Schechter I, Ben-Chorin M, Kuz A. Sensitive, selective and tunable nanostructure modified porous silicon gas sensor. Anal Chem 1995; 67:3727.

[46] (a) Schlesinger M, Paunovic M. Modern Electroplating, 4th edn., New York, John Wiley and Sons, 2000; (b) Fundamentals of Electrochemical Deposition, $2^{nd}$ edn. New York, Wiley, 2006.

[47] Weller G L, Pratt S J. Measuring phosphine: how sensors work. In: Wright E J, Webb M C, Nightly H, editors, Proceedings of the Australian Postharvest Technical Conference Canberra 25-27 Jun. 2003.

[48] Dirkson J A, Duval K, Ring T A. NiO thin film formaldehyde gas sensor. Sensor Actuator B: Chem 2001; 80:106-115 and references therein.

[49] Mabrook M, Hawkins P. Benzene sensing using thin films of titanium dioxide operating at room temperature. *Sensors* 2002; 2:374-382.

[49] Gole J L, Prokes S M, Glembocki O J, Yang R. Unique properties of selectivity form $ZrO_x$ nanostructures-light enhancement from a metal oxide. Adv Mater 2006; 18:664.

[51] Gole J L, Stout J, Burda C, Lou Y, Chen X. Highly efficient formation of visible light tunable $TiO_{2-x}N_x$ photocatalyst and their transformation at the nanoscale. *J Phys Chem B* 2004; 108:1230-1240.

[52] Gole J L, Chen X, Lou Y, Samia A C S, Burda C. Formation of oxynitride as the photocatalytic enhancing site nitrogen-doped titania nanocatalysts comparison to a commercial nanopowder. Adv Funct Mater 2005; 15:41-49.

[52] Gole J L, Kumar S, Fedorov A G, Photodegregation of ethylene using visible-light responsive surfaces prepared from titania nanoparticle slurries. J Appl Catalysis Envir 2005; 57:93.

Example 3

Brief Introduction

A concept, complementary to that of hard and soft acid-base interactions (HSAB-dominant chemisorption) and consistent with dominant physisorption to a semiconductor interface, is presented. We create a matrix of sensitivities and interactions with several basic gases. The concept, based on the reversible interaction of hard-acid surfaces with soft bases, hard-base surfaces with soft acids, or vice versa, corresponds 1) to the inverse of the HSAB concept and 2) to the selection of a combination of semiconductor interface and analyte materials, which can be used to direct a physisorbed vs chemisorbed interaction. The technology, implemented on nanopore coated porous silicon micropores, results in the coupling of acid-base chemistry with the depletion or enhancement of majority carriers in an extrinsic semiconductor. Using the inverse-HSAB (IHSAB) concept, significant and predictable changes in interface sensitivity for a variety of gases can be implemented. Nanostructured metal oxide particle depositions provide selectivity and complement a highly efficient electrical contact to a porous silicon nanopore covered microporous interface. The application of small quantities (much less than a monolayer) of nanostructured metals, metal oxides, and catalysts which focus the physisorbtive and chemisorbtive interactions of the interface, can be made to create a range of notably higher sensitivities for reversible physisorption. This is exemplified by an approach to reversible, sensitive, and selective interface responses. Nanostructured metal oxides developed from electroless gold ($Au_xO$), tin ($SnO_2$), copper ($Cu_xO$), and nickel (NiO) depositions, nanoalumina, and nanotitania are used to demonstrate the IHSAB concept and provide for the detection of gases, including $NH_3$, $PH_3$, CO, NO, and $H_2S$, in an array-based format to the sub-ppm level.

Introduction

In order to meet the criteria necessary for the detection, monitoring, and transformation of a diversity of materials and effluents, gas sensors and microreactors adopt a multitude of configurations. Conductometric gas sensors can be made to consist of a sensitive surface layer that can be transformed through the introduction of nanostructures. These sensors, which are conducive to the rapid and reversible transduction of sub-ppm levels of analyte gas, offer a most attractive subgroup.[1,2] Because of the strongly interacting nature of nanostructures, arrayed configurations capable of highly distinct, predictable, and inexpensively calibrated responses for a prescribed set of analyte gases, at room temperature, would represent ideal devices for a diversity of applications. Efforts to form such devices utilizing a hybrid nanoporous/microporous silicon medium as the transduction site have produced individual gas sensors.[1-4]

Here, we outline a concept, based on the inverse of the Hard and Soft Acid-Base interaction model (IHSAB), which suggests a general approach to optimally design sensors with improved sensitivity for a variety of gases. This concept also complements microreactor design. The selective fractional deposition of nanostructured materials to the surface of a prepared semiconductor interface can be used to create, in combination, microfabricated arrays with integrated (CMOS) circuits. The IHSAB principle/approach is complementary to that of hard and soft acid and base interactions (HSAB) first put forth by Pearson, et al.[5] and later correlated within the context of density functional theory (DFT) and Chemical Reactive Theory (CRT) by Pearson, Parr,[6,7] and their coworkers. The IHSAB approach to conductometric sensor development which we develop correlates with a basis in physisorption. In contrast, microreactor design correlates with a basis in chemisorptive interaction. The application of the IHSAB concept creates highly variable surface interactions using a diversity of nanostructured oxide fractional depositions.

Nanoporous silicon layers positioned on porous silicon micropores facilitate the application of nanostructured metals, metal oxides, and catalytic nanoparticles, and provide for notably higher sensitivities and selectivity. These depositions can be made to produce a dominant physisorptive (sensors) or chemisorptive (microreactors) character at the semiconductor interface as the deposited nanostructured metal oxides act as antennas to focus the nature of the surface interaction. Here, we consider primarily physisorption as it applies to sensor development. However, complementary principles and the HSAB concept can be applied to microreactor design.

Results and Discussion

The Inverse of the Hard and Soft Acid Base Concept as the Basis for the Construction of Nanostructure Directed Physisorption at Sensor Interfaces An analyte can donate electrons to a "p-type" porous silicon (PS) semiconductor surface and these electrons combine with holes, thus reducing the number of majority charge carriers. This leads to an increased resistance. The process is reversed for an "n-type" semiconductor as the majority charge carriers, electrons, increase and the resistance decreases. We suggest that the IHSAB concept as it promotes physisorption can be applied in concert with and in complement to the behavior of an extrinsic semiconductor to provide a range of responses that can be used to design and create sensor arrays.

The concept of chemical hardness/softness first developed by Pearson[5] has its basis in the nature of metal ion complexation in aqueous solution. The HSAB theory is a generalization of the Lewis acid/base concept and correlates with chemical reactivity theory (CRT).[8] It was given a deep foundation in density functional theory[7] by Parr and coworkers, following an initial correlation with the molecular properties established by Pearson and Parr.[6] More recently, conflicts underlying the correlation of the DFT and CRT theories have been largely resolved by Cohen and Wasserman[8] and Zhan et. al.[9] who have further refined the concepts of electronegativity and hardness.

The properties of acids and bases can be described as hard and soft based upon the correlation of several atomic/molecular properties which include the ionization potential, I, the electron affinity, A, and the chemical potential, $\mu$. These can be correlated, in concert with the HOMO-LUMO gap concept from molecular orbital theory as the Kohn-Sham orbitals replace the molecular orbitals[7a]. Examples in terms of groups of hard, borderline, and soft acids and bases are given in Table 1, Ex. 3. For a soft acid, the acceptor atom is of low positive charge, of large size, and has polarizable outer electrons. In a hard acid, the acceptor atom is of small size and not easily polarized. In a soft base, in precise contrast to a hard base, the donor atom is of low electronegativity. It is easily oxidized, and highly polarizable, with low-lying unoccupied molecular orbitals. The HSAB principle was initially based on empirical observations. Yet, as it groups acids and bases, a basis for it has been developed in terms of DFT. This basis follows the principle that soft-soft combinations produce significant covalent bonding and hard-hard combinations produce significant ionic bonding. The HSAB principle states that hard acids prefer to coordinate to hard bases whereas soft acids prefer to coordinate to soft bases. The driving principle to promote physisorption represents the inverse (IHSAB) of the concept to form strong chemical bonds.

TABLE 1

Exemplary Hard, Borderline, and Soft Acids and Bases[a].

| | Hard | Borderline | Soft |
|---|---|---|---|
| Acids | $H^+$, $Li^+$, $Na^+$, $K^+$ | $Fe^{2+}$, $Co^{2+}$, $Ni^{2+}$ | $Cu^+$, $Au^+$, $Ag^+$, $Tl^+$, $Hg^+$ |
| | $Be^{2+}$, $Mg^{2+}$, $Ca^{2+}$ | $Cu^{2+}$, $Zn^{2+}$, $Pb^{2+}$ | $Pd^{2+}$, $Cd^{2+}$, $Pt^{2+}$, $Hg^{2+}$ |
| | $Cr^{2+}$, $Cr^{3+}$, $Al^{3+}$ | $SO_2$, $BBr_3$, $Sn^{2+}$ | $BH_3$ |
| | $SO_3$, $BF_3$, $Sn^{+4}$, $Ti^{+4}$ | $NO_2$, $NO^+$ | |
| Bases | $F^-$, $OH^-$, $H_2O$, $NH_3$ | $NO_2^-$, $SO_3^{2-}$, $Br^-$ | $H^-$, $R^-$, $CN^-$, CO, $I^-$ |
| | $CO_3^{2-}$, $NO_3^-$, $O_2^-$ | $N_3^-$, $N_2$, $H_2S$ | $SCN^-$, $R_3P$, $C_6H_5$ |
| | | $C_6H_5N$, SCN | $R_2S$ |

[a]Inorganic Chemistry, J. E. Huheey, E. A. Keiter, R. L. Keiter, 4th Edition, Harper Collins College Publishers.

Within the HSAB-DFT framework, the electronic chemical potential[6,7(a),10]

$$\mu = (\partial E(N)/-\partial N)\upsilon_e = (\delta E/\delta \rho)\upsilon_e \quad (1)$$

is a global quantity. Here E(N) is the ground state energy of a system of N electrons in the electrostatic potential energy, $\upsilon_e$, due to its nuclei (fixed) and E is a functional of the electron density, ρ. The 3 point finite difference approximation for $\partial E(N)/\partial N$ gives $\mu \approx -(I+A)/2$ with I the ionization potential and A the electron affinity.

μ is then the negative of the Mulliken electronegativity, $X_M$.

$$X_M \approx -\mu(I+A)/2 \quad (2)$$

The absolute hardness, η of a species, is defined[6,11] as $$\eta = (\partial^2 E(N)/\partial N^2) - \upsilon_e = (\partial \mu/\partial N)\upsilon_e \approx (I-A) \quad (3)$$

and the absolute softness[12] is the inverse of the hardness $$S = \eta^{-1} \approx (\partial N/\partial \mu) - \upsilon_e \quad (4)$$

The approximation in Eq. 3 arises from the use of the finite difference formula.

Unlike the chemical potential, the hardness is not constrained to be constant everywhere throughout a system, having local values for which η is a global average. Parr and coworkers[7,12,13] have defined a local hardness which corresponds to the change in chemical potential with electron density in different parts of a molecule, complex, or, simply, a system. Cohen and Wasserman[8] define a generalization to include a hardness matrix that incorporates both the self-hardness of individual species and the mutual hardness for pairs of species combining in a system. The idea of a local hardness is critical to the interpretation of the IHSAB and HSAB model on a surface. Cohen et. al.[8] also provide a description of local softness as they demonstrate how the reactivity of a species depends on its chemical context. As interacting constituents separate, the hardness matrix becomes diagonal in the self-hardness. It is possible to establish a more general description of electronegativity (Eq. 2) equalization[8] and of those molecular orbitals (MO's) involved in the process of electron transfer from an acid to a base.[8]

If two systems B and C are brought together, electrons will flow from the system of lower χ (Eq. 2) to that of higher χ to equilibrate the chemical potentials. For solid-solid interactions, equilibration of the Fermi levels represents the analog of chemical potential[8] equilibration. Therefore, it is not difficult to envision the extrapolation of these concepts to the interaction of a molecule with a particle decorated interface. To the first approximation of an acid-base interaction, the fractional number of electrons transferred can be defined by $$\Delta N = (X_C - X_B)/2(\eta_C - \eta_B) \quad (5)$$

where the difference in electronegativity drives the electron transfer and the sum of the hardness parameters acts as a resistance. This expression, while approximate, is useful because it defines the nature of the initial interaction between two systems using properties of the isolated systems. Whereas the absolute chemical potential and hardness are molecular parameters, the flow of electrons is from a specific occupied molecular orbital of B to a specific empty orbital in C. Thus, the overlap between exchanging orbitals will be critical in determining energy change and the nature of chemical interaction.

The correlation of hardness and softness with molecular orbital theory can be obtained from the Frontier orbital concept of chemical reactivity theory.[14] Here, within the context of Koopman's theorem for both the ionization energy and the electron affinity, the frontier orbital energies can be correlated with the expressions for chemical potential (Eq. 1, 2), hardness (Eq. 3), and softness (Eq. 4) as $$-\epsilon_{HOMO} = I, \quad -\epsilon_{LUMO} = A. \quad (6)$$

The concept of hardness thus reduces to the statement: hard molecules have a large HOMO-LUMO gap and soft molecules have a small HOMO-LUMO gap.[5] Thus the criteria that hard acids prefer to coordinate to hard bases and soft acids to soft bases is, in one sense, a HOMO-LUMO matching criteria. In complement, Politzer[15] has shown that the softness of atoms correlates with their polarizability. Here we promote a HOMO-LUMO mismatch to induce physisorption.

In contrast to the driving force of the HSAB concept and chemisorptive interaction, to create sensitive, rapidly responding, and reversible porous silicon gas sensors, it is necessary to avoid processes which lead to strong ionic or covalent bonding. Rather, we emphasize the inverse correlation focused on physisorption with minimal chemical interaction. This would suggest the result, which the data in Table 2, Ex. 3, and the following sections exemplify, that a general approach to conductometric chemical sensor development should follow the inverse of the HSAB concept of acid-base chemical interaction. The changes in response of nanostructure particle modified porous silicon interfaces outlined in the following discussion can be correlated with this inverse (IH-SAB) behavior.

TABLE 2

Ex. 3. Response to Nanostructured Depositions.

|  | Tin (SnO$_2$) | Nickel (NiO) | Copper (Cu$_x$O) | Gold (Au$_x$O) |
|---|---|---|---|---|
| PH$_3$ | 2 | 2.5 | 4 | 5 |
| NO | 7-10 | 3.5 | 1 | 1.5 |
| NH$_3$ | 1.5 | (1.5-2) | (2-2.5) | ~3 |

ΔR (coating)/ΔR(uncoated) values are shown for PH$_3$, NO, and NH$_3$ resistance changes. Comparison is to an uncoated PS sensor for the analyte gases at 1 ppm. The nanostructured coatings deposited to the PS surface are indicated in the Table. Base resistances of the sensors used in these experiments vary from 300 to 500 Ω. Further data points for CO (SnO$_2$), and H$_2$S (Au$_x$O) are discussed in the text.

Physisorption and the Response of a Sensor Platform

The introduction of nanostructures to the micro/nanoporous PS framework can selectively modify the resistance response to considerably improve gas detection. In a set of initial experiments,[2,4,16] we determined that the concentration of SnO$_2$ and Au$_x$O nanostructures on the micro/nanoporous framework needed to produce an enhanced sensitivity for PS (FIG. 4.4) is notably less than the nanostructure deposition illustrated in the Experimental section. The deposited nanostructures are sparsely interspersed onto the micro/nanoporous framework. An SnO$_x$ deposited sensor, in particular, allows the room temperature detection of CO at the sub-ppm level considerably below the sensitivity of other PS sensors.[17-19] This SnO$_2$ deposited sensor can be compared with PS-based sensors whose resistances exceed hundreds of kΩ, operating on a 2 V bias,[17] SnO$_2$ sensors operating at 300° C.-500° C.,[18] and similar gas sensors operating at 2-5 V.[19] It has been possible to considerably improve the basic hybrid PS sensor micro/nanoporous interface. With this improvement, electroless gold treatments of the PS interface forming Au$_x$O nanostructured deposits have lead to a substantial increase in sensitivity (signal/noise) for ammonia.[4] However, the ratio of the improvement in response of the Au$_x$O nanostructure deposited hybrid PS surface to that of an untreated PS surface closely parallels that for FIG. 4.4 and is again duplicated by the newly expanded and reproduced response array for NH$_3$ presented in Table 2 (Ex. 3). The results outlined in FIG. 4.4 and the newly obtained data in Table 2, Ex. 3, are fundamental to the development of the IHSAB concept which we outline in this study.

We have performed extensive additional studies involving the sensing of a number of gases, including the sensing of phosphine, for several nanostructure modified PS surfaces. These specific experiments, carried out in a manner similar to that previously described,[2,4,20,21] are summarized in Table 2, Ex. 3. The preparation of each surface, will be discussed in considerable detail elsewhere.[21] Table 2, Ex. 3, presents several correlated responses. The results which we have obtained for phosphine, the most complicated system we have studied, ($NH_3$ is of similar complexity) are depicted for an $Au_xO$ nanostructure coated micro/nanoporous PS surface in FIG. 4.1.[21] $PH_3$ is known to display an even greater degree of interaction with a nanostructured surface and have a higher sticking coefficient than $NH_3$.[2,20,21] The tendency toward the equilibration of adsorption and desorption, also manifest in ammonia, can produce a gradual increase in the sensor baseline. Although we operate the sensors in an unsaturated mode,[2,20] the sensor response and recovery time scales are distinctly different. The observed baseline drift can also result from weak chemisorptions of $PH_3$ superimposed on a dominant physisorption.[21] Purging the sensor surface with ultrahigh purity (UHP) nitrogen for longer durations, following exposure to the 300 s $PH_3$ gas pulse (FIG. 4.1), enhances the return to the initial baseline. This return to baseline can also be further improved by more tightly constraining the gas flow path to the sensor surface from its current design for operation at atmospheric pressure. In addition, the application of FFT pulsing techniques can be used to average out the effects of the baseline drift.

FIG. 4.1 demonstrates that the resistance change for $PH_3$ resulting from an $Au_xO$ nanostructure deposited surface is close to five times that of the untreated surface. Further data obtained for electroless tin, copper, and nickel treatments are indicated in Table 2, Ex. 3. Table 2, Ex. 3 also includes additional new data obtained for NO[22] with electroless tin, copper, nickel, and gold treatments to the hybrid PS interface form $Sn^{+4}$, $Cu^{+1,+2}$, and $Ni^{+2}$ oxides, and $Au_xO$ [$Au^{0,+1}$] clustered oxide nanostructured deposits. The individual studies, which allow the detection of $PH_3$ and NO to <300 and 650 ppb respectively, the prescription for their formation, and their row matrix of responses will be discussed in more detail for each individual gas.[21] However, the summarized improvement obtained for NO with $SnO_2$ and NiO deposits vs. the hybrid PS structure is apparent.

Table 2, Ex. 3 summarizes the results we have obtained for several nanostructure modified PS surfaces for the gases $NH_3$, $PH_3$, and NO at the one ppm level. The ratio of resistance changes are given for the various nanostructure deposits relative to an untreated micro/nanoporous PS structure. In addition, the data obtained for CO, a weak base, demonstrates a significant response increase upon exposure of this gas to an $SnO_2$ (hard acid, Table 1, Ex. 3) nanostructure coated surface. The response increases by at least an order of magnitude relative to the untreated PS surface. In contrast, although the response of the PS surface is quite small, the $Au_xO$ treated PS surface response has clearly decreased for CO, signalling the chemical interaction of a weak base with a weak acid interface. Further data obtained for $H_2S$[16] (an intermediate base, Table 1, Ex. 3) indicates a significant increase in response (between 1.5 and 2) for an $Au_xO$ nanostructured oxide (weak acid) coated surface relative to the untreated PS surface. The observed ratios in Table 2, Ex. 3 demonstrate that the same relative signal improvements for $NH_3$ and NO, for the new data presented in Table 2, Ex. 3, are as indicated in FIG. 4.4. The ratios of responses are thus maintained for an extended group of experiments. For ammonia, the data in FIG. 4.4 has been improved to provide responses over two orders of magnitude larger as a result of improvements in the optimization of the anodization and nanostructure deposition processes. The response change, now on the order of $1000\Omega$ for 20 ppm $NH_3$ with respect to the untreated porous silicon sensor, corresponds to a similar enhancement increase after an $Au_xO$ nanostructure treatment is applied.

FIGS. 4.1 and 4.4 and Table 2 (Ex. 3) suggest that the proper combination of nanodeposition techniques can be used to produce combinations of array-based multiple sensor devices of varying sensitivity to a variety of basic gases. The matrix of array responses can be correlated to selectively analyze gas mixtures. For example, a sensor array consisting of an untreated, $SnO_x$ nanostructure coated, and gold clustered oxide nanostructure coated sensor can be used to sensitively test for the presence and relative concentrations of ammonia and nitric oxide. A nanostructured $PS/SnO_2/Au_xO$ sensor combination could provide the basis for developing a sensitive room temperature detector that could be installed as a simple sensor system for asthmatics, for example.[2]

Interaction with Nanostructure Modified Porous Silicon Surfaces

Here, we assess whether the underlying IHSAB principle described above dictates the response that we have observed from several sensor, basic gas, interactions. We suggest that this principle can be extended to the detection of additional gases with the development of a selective nanostructure deposition approach which facilitates reversible physisorption. This approach is based on creating those conditions which represent the inverse of the concept of hard and soft acids and bases developed by Pearson and others,[5-9] based on the creation of significant covalent or ionic bonds which should lead to a significant chemisorptive surface interaction. We suggest that, by monitoring the trends in hard and soft acid and base behavior, first order selections can be made for the appropriate modification of the PS hybrid interface with nanostructured metal/metal oxide coatings to create a range of selectivities for a number of gases.[4,16(c),22] The development of selective nanostructured coatings that reversibly complex with a gas can be based on an IHSAB concept where we now combine hard Lewis acids with soft Lewis bases or soft Lewis acids with hard Lewis bases. To establish this combination, we follow the trends established for the classification of the hard and soft nature of acids and bases.[5-7]

A first order comparison of the response data in Table 2, Ex. 3 with the exemplary list of hard, borderline, and soft acids and bases in Table 1, Ex. 3 clearly demonstrates that hard bases such as ammonia (and ~phosphine) respond most strongly (resistance change) when exposed to a nanostructured $Au_xO$ surface corresponding to a soft acid ($Au^{0,+1}$). In contrast, the soft bases CO (and NO) display a maximum response (change in resistance) upon interaction with the borderline to hard acid $SnO_x$ ($Sn^{+2,+4}$). Note also the minimum response of the untreated PS surface to CO and the subsequent decrease for the $Au_xO$ nanostructure treated surface displayed in FIG. 4.4. These properties have not changed over an extended period as we observe no clearly measureable response with either an untreated or an $Au_xO$ nanostructure treated PS surface. The decrease in an already small if negligible resistance response for hybrid PS is consistent with the expected effect of chemisorption for the interaction of a weak acid with a weak base to create a stronger, more covalent, chemical bond which does not facilitate electron transfer.

The responses outlined in Table 2, Ex. 3 in concert with FIGS. 4.1 and 4.4 and Table 1, Ex. 3 can be correlated further to generate the materials positioning depicted in FIG. 4.2. This positioning diagram is generated based on the relative responses for the gases we have studied, with several nanostructured deposits over an extended period. We position the five bases $NH_3$, $PH_3$, $H_2S$, NO, and CO relative to the porous silicon ($Si^{+1\ to\ +4}$) and the PS modified acidic interfaces generated with a nanostructured $SnO_x$ ($Sn^{+2,+4}$), $Al_2O_3$ ($Al^{-+3}$), NiO ($Ni^{+2}$), $Cu_xO$ ($Cu^{+1,+2}$), and $Au_xO$ ($Au^{0,+1}$) deposit. The basis for the positioning of $H_2S$ in FIG. 4.2 is the correlation of the relative responses for one ppm $H_2S$ with an $Au_xO$ deposited surface compared to an untreated PS surface[20] and to the data for $NH_3$, $PH_3$, and NO in Table 2, Ex. 3. Based on ionization potential as well as proton affinity data, we suggest that $H_2S$ lies close to but probably to the soft acid side of $PH_3$. The basis for the positioning of CO is its virtually non-existent response to $Au_xO$ and its substantial response to $SnO_2$ summarized in FIG. 4.4 and re-evaluated in several experimental tests. Data for $Al_2O_3$ deposits has been generated only for phosphine for which the response is found to be virtually identical to the hybrid PS interface. Thus the acid strength of the alumina modified PS surface as well as the untreated PS surface and the base strength of $PH_3$ are closely aligned.

We are correlating the interaction of gaseous bases with nanostructured surfaces. The location of each of these bases is evaluated based upon their observed interaction with the range of treated PS surfaces. The data in Table 2, Ex. 3 suggest that a general approach for optimal PS conductometric sensor response based on physisorption should have as its driving force the combination of a weakly acidic sensor surface with a strongly basic interacting molecule or vice-versa. (Similar comments would apply to a strongly or weakly basic surface). Within the framework of molecular orbital theory, we attempt to promote a mismatch between the HOMO-LUMO gaps associated with the acidic and basic orbitals. This mismatch is, as it should be, to produce rapidly responding, "reversible", sensor configurations, minimizing either strong covalent or ionic bonding and maximizing a physisorbed interaction. By promoting this interaction, we minimize the effect of chemical bond formation which inhibits the transfer of electrons to the modified PS interface.

With a focus on sensor array development, the data in Table 2, Ex. 3, can be correlated with the exemplary information reflected in Table 1, Ex. 3. The correlation suggests the materials positioning indicated in FIG. 4.2 within especially similar molecular analogues. We have constructed FIG. 4.2 within the framework of the acid and base character outlined in Table 1, Ex. 3 considering, to first order, the hard acid strength which we associate with an $Sn^{+4}$ ($SnO_2$) configuration, the soft acid strength to be associated with an $Au^{0,+1}$ ($Au_xO$) configuration, and the intermediate (borderline) acid strength we associate with the porous silicon hybrid surface. Here, the silicon oxidation state ($Si_xO_y$) is considered to vary from +1 to +4.[23] Superimposed relative to this structure, we insert the results outlined in Table 2, Ex. 3 for the intermediate acid $Ni^{+2}$, the soft and intermediate acids $Cu^{+1,+2}$, and the comparatively strong acid state with which we associate $Al^{+3}$ ($Al_2O_3$).

There are several additional factors that we take into account in constructing FIG. 4.2. A larger resistance change associated with $SnO_2$ suggests that ammonia lies closer to porous silicon than to the strong $Sn^{+4}$ acid site. The inherently hard basic character of ammonia is also consistent with the strong resistance change observed for its interaction with the $Au_xO$ nanostructure deposited surface (Table 2 (Ex. 4)). The behavior of ammonia is also strongly mimicked by phosphine which displays an expected strong increase in resistance change relative to the "p-type" PS surface associated with $Cu_xO$ and $Au_xO$ nanostructure modified surfaces. We observe a decrease in the magnitude of the resistance response increase relative to the untreated PS surface as a result of a ($Ni^{+2}$) oxide nanostructure deposition. This suggests that the ($Ni^{+2}$) treated surface lies to the soft acid side of the untreated hybrid PS surface. The remaining interactions with NO and $NH_3$ suggest a ($Ni^{+2}$) acid strength in closer proximity to PS. This defines the broader relative response for the $Ni^{+2}$ and hybrid PS regions indicated in FIG. 4.2. As we have noted for phosphine, the responses to the hybrid PS structure and an "$Al_2O_3$" nanostructure treated surface appear virtually identical. Therefore, we anticipate that phosphine lies equally close to $Al_2O_3$ and PS with $NH_3$, a stronger base, on the hard base side of $PH_3$. This also suggests that the acid character of $Sn^{+4}$ considerably exceeds that of $Al^{+3}$. More recent preliminary results[24] obtained working with MgO treated $TiO_2$ and $TiO_2$ nanostructures prepared using sol-gel methods show a 4 to 5 fold increase in resistance change compared to the untreated hybrid PS surface response to $PH_3$. These responses, thought to be dominated by the action of $Ti^{+4}$, suggest the response of a harder acid than $Sn^{+4}$ with a moderately strong base, $PH_3$.

The doublet NO radical has a singly occupied HOMO as compared to the doubly occupied HOMO of closed shell ammonia or phosphine and represents a weak base. The open shell nature of NO would suggest a very different interaction with hybrid PS and the nanostructure treated PS interface. In addition, NO can bind an electron which $NH_3$ and $PH_3$ cannot. The soft base-hard acid interaction of NO with a $SnO_2$ nanostructured coating leads to a substantial resistance change relative to PS. This is the signature of the reversible interaction of a strongly acidic surface with a weak base. Further, the response to gold, copper, and nickel treated surfaces, while considerably muted relative to the tin treated surface, suggests that NO should be positioned directly below the copper ($Cu^{+1,+2}$) systems and intermediate to gold ($Au^{0,+}_1$) and nickel ($Ni^{+2}$). The interaction of NO with $Ni^{+2}$ suggests a greater separation from nickel than from gold. While PS and $Ni^{+2}$ may lie in a similar intermediate region, the larger resistance change observed for NO with a $Ni^{+2}$ surface suggests that the ($Ni^{+2}$) modified PS surface lies to the hard acid side of PS, acting as a harder acid deposited to the PS surface. This again suggests a broader range for the relative response of the $Ni^{+2}$ and PS regions as indicated in FIG. 4.2.

IHSAB Model—Influence on the Interaction of Analyte Gases with a Semiconductor Surface FIG. 4.2 is constructed within the framework of an Inverse HSAB concept with a focus toward the improvement of surface physisorption based on select nanoparticle deposition. We offer a plausible mechanistic principal for the sensor resistance changes observed for the effectively oxidized gases considered in this study. The introduction of the nanostructured metal oxides to the nanoporous PS surface modifies the sensing process by transforming the surface of the chemically sensitive "p-type" PS nanoporous layer. It is clear that the sensor resistance increases for "basic" gases which are oxidized (NO, CO, $NH_3$, $PH_3$, $H_2S$). This process is amplified through the interaction of a modified acidic metal oxide surface. If an electron is donated to a "p-type" PS surface, this process will act to reduce the number of majority carriers (holes) and thus will promote an increase in resistance. In contrast, the interaction of a gas that is effectively reduced on "p-type" silicon, exemplified by the acidic gas $NO_2$, leads to the removal of electrons from the "p-type" PS surface, the increase of majority charge carriers, and a decreased resistance.[24] In effect the nanostructures act as antennas to transduce charge. This process will be reversed for an "n-type" sensor[25] such as bulk tin oxide where the contribution of electrons to the bulk interface contributes to the number of majority carriers (electrons).

The process of physisorption must involve the interaction of high-lying occupied (low lying unoccupied) molecular orbitals of each individual gas which are the electron donors (acceptors) with the electron acceptor (donor), represented by the acidic (basic) metal oxides used to modify the PS surface and the "p-type" PS itself. This process will differ from gas to gas and with the change in nanostructured deposit. However, the nature of the interaction as it provides for increased physisorption and minimizes chemical bond formation (chemisorption), therefore influencing the flow of electrons from the gaseous molecule to the sensor, provides the basis for the observed resistance change. We suggest that the presence of a fractional nanostructured oxide coating on the PS surface serves to promote further interaction with the interface and that the process whereby a gas transfers or withdraws electrons as it interacts with that surface will be strongly influenced by the balance of chemical bonding, which greatly inhibits electron flow, and physical absorption which can facilitate the process.

In this study, we have considered the fractional coverage of a "p-type" porous silicon surface with several nanostructured metal oxide particles. This fractional coverage, while it influences the physisorption to the PS surface, should not greatly modify the "p-type" character of the generated PS surface used in this study.[26] However, the fractional deposition must be held to a low level. Within this framework, we have demonstrated that the nanostructured deposits, as they influence the resistance change, maintain their characteristics over extended periods of testing.

The precise details of this mechanism and the resistance change which appears to be characteristic of virtually all effectively oxidized (increased resistance) and reduced (decrease in resistance), gases with the individually modified hybrid "p-type" PS surfaces will require further experimentation and modeling. If we, however, consider an appropriate sensor mechanism for interaction with oxide surface subgroups, the fractional nanostructure coating of a "p-type" sensor is consistent with the change in resistance that we outline above. Basic analytes will provide an electron to the p-type PS surface whereas acidic analytes will remove an electron leading to a decrease or increase in the number of majority carriers respectively. It is important to note that these changes are opposite to the resistance changes for n-type bulk sensors.[25]

The conductometric sensors, which we formulate, using the IHSAB principle, are simply designed and can operate with less than 1 mW of power. They are potentially sensitive as well as selective to a wide variety of gases while operated at room temperature. These rapidly (≤2 s) and reversibly responding devices, with an inherent low voltage and lower power,[2,4,20] can be readily integrated with CMOS electronics into arrays of sensors. This follows from the ability to modify the interaction of a "p-type" PS sensor using a "materials selection table"[22] analogous to Table 1, Ex. 3 to create arrayed devices. The modified PS sensor is also of interest due to its operation at atmospheric pressure and at room temperature as well as over a single, readily accessible, temperature range with an insensitivity to temperature drift. Using the construction of FIG. 4.3, and operating the sensor in a heat-sunk configuration, can allow reliable performance to a surface temperature of 80° C. even in highly elevated temperature environments (in sharp contrast to metal oxide sensors). The sensor also offers a strong alternative as a result of its ease of modification with a diversity of clearly mapped gas-selective nanostructured materials, providing a range of sensitivities for a given gas and the format for sensor arrays. Further, the sensor shows promise as a result of its low cost of fabrication, usually with a single nanostructure modification, its ease of operation combining micro- and nanotechnology, and its ease of rejuvenation following contamination.[4] Finally, it can be used to rapidly assess false positives, using FFT techniques and operating the sensor in a pulsed mode.[27] Many of these improvements are greatly aided by the application of the IHSAB concept.

Conclusion

We offer an approach to focus the physisorption of an extrinsic semiconductor surface and facilitate significant and predictable changes in sensor surface sensitivity for a variety of gases based on an inverse complementary theory to the well known concept of hard and soft acid and base interactions.[5-9] Similar considerations can also be applied as a first order approach to the focusing of the chemisorptive properties of a semiconductor interface. We suggest that nanostructured sensor surfaces for conductometric array-based devices be constructed from a finders table by first establishing whether the gas to be detected classifies as a hard or soft acid or base and subsequently developing a range of nanostructured fractional deposits which modify a prepared semiconductor interface to encompass as wide a range of acidity and basicity as possible. More specifically, for the gases considered in this study, the correlation with the trends in the proton affinity (PA), essentially the gas phase basicity, and their interaction with the modified acidic PS surface also bears serious consideration.[28] However, as an overriding principle, the maximum physisorbtion response (resistance change) is to be expected from combinations of hard acid surfaces with soft bases and vice versa. While there are other factors, including steric effects, polarization,[15] and the nature of the open or closed shell character of interacting molecules to consider, we suggest that the acid/base makeup of the nanostructure modified PS sensor surface and the mismatch of the hard and soft acid/base character with the species to be detected is the primary driving force for creating the most efficient modified sensor surface. This comment must be tempered by noting that the interaction of a strongly acidic surface with a weakly basic gas can influence the characteristic interactions of this gas. Further, the interaction of amphoteric gases must also be carefully assessed within the model.

Experimental Section

The porous silicon (PS) micro/nanoporous interfaces used in this study are generated exclusively from "p-type" silicon. They have been transformed within the framework of nanotechnology employing the IHSAB concept as a means to develop highly efficient nanostructure modified sensors. Schematic diagrams of the working sensor platform are indicated in FIG. 4.3. The porous silicon interface is generated by electrochemical anodization of 7-13 ohm-cm, p-type, (100) silicon wafers (Siltronix). The anodization to produce a nanopore covered microporous structure[2] is done in 1M $H_2O$, 1M HF, and 0.1 M tetrabutylammonium perchlorate (TBAP) in acetonitrile (MeCN) at 3-6 mA/$cm^2$. The anodized sample is cleaned in MeCN for 10 min. to purge any residue in the pores due to the etch solution. It is then immersed for several minutes in HF and then in methanol. The porous silicon has a porosity of 50-80%, with the μ-pore diameters varying from 0.8 to 1.5 μm and pore depths varying from 10 to 30

Before the anodization, an insulation layer of SiC (~1000 angstroms) is coated onto the c-Si substrate by PEVCD methods and windows of 2×5 mm are opened on this layer by Reactive Ion Etching (RIE). The SiC layer serves two purposes. First, it makes hybrid porous silicon creation possible in the specified windows during electrochemical anodization because of its resistance to HF. Second, it helps the placement of gold contacts exclusively on the porous layer for resistance measurements and serves as an electrical insulator on the doped silicon. We continue to employ low resistance gold contacts[2-4], whose formation has been discussed in detail previously. These contacts are made to the nanopore coated microporous arrays which are etched into a p-type wafer[2-4]. This process is exemplified further in the two views given in FIGS. 4.3A and B[2-4]. The PS hybrid arrays of nanopore covered micropores, depicted also in FIG. 4.3B, are tested at room temperature for their individual sensor response. The selected fractional nanostructure deposition, indicated in schematically in FIG. 4.3 and pictured in side and top views in FIGS. 2.1A, B, and C, is used to create an improved physisorption dominated sensor response. The nature of this response, we will suggest, is based on the use of the acid/base concepts which we have outlined in the previous discussion. The select preparation of the nanopore coated micropore structure as exemplified in FIG. 2.1A is detailed elsewhere. [20] The hybrid PS introduces additional active nanopore sites for the analyte test gas-surface interaction as well as a much larger surface contact area (in contrast to a purely microporous surface). The nanopore/micropore combination also provides for enhanced diffusion of the analyte gas to active sites.[29] Depositing a select nanoporous surface with metal oxide nanoparticles/clusters introduces new selective sites on the nanostructured substrate resulting in a modification of the response to a specified analyte gas. It is this etched PS structure which provides both for a combination of rapid Fickian diffusion[2(a)] into the readily observable micropores followed by a limiting Knudsen diffusion[17] into the nanopore wall coating of the micropores.

Selected nanostructured metals, metal oxides, and nanoparticle catalysts can be deposited on the nanopore covered PS micropores. This provides for distinct, variable, and, in most cases, notably higher sensitivities which, in combination, can be used as a basis to develop selectivity. Metals which include electroless gold[30], tin[31], copper[32], and nickel[33] as well as nano-alumina[34], titania[35], and zirconia[36] provide for the detection of the gases NO, CO, $NH_3$, $PH_3$, and $H_2S$ at the sub-ppm level.[2-4,20,21] Results obtained with electroless tin and gold coatings[2,4] are presented in FIG. 2.1B and C, which indicate side and top views respectively of these depositions. Here, the introduction of electroless tin produces a tin deposit that is readily oxidized to an $SnO_x$ ($x=2,\gg1$) deposit whereas an electroless gold deposit undergoes a much slower oxidation and results in the formation of gold clustered oxide nanostructures, $Au_xO$ (FIG. 2.1C) positioned within the micropores.

With the exception of the gold depositions, all of the nanostructured metals deposited onto the PS surface are readily oxidized. The initially produced titania[35] (anatase), zirconia [36] (rhombohedral), and alumina nanostructures may be crystalline, however, we cannot be certain that they retain their crystallinity after being deposited to the PS surface. The untreated PS hybrid structures are exposed to the electroless solutions for 30 seconds and are placed in DI $H_2O$ and MeOH for consecutive 30 second periods.[21] The oxidized electroless metal depositions before deposition appear to correspond to amorphous structures displaying no diffraction patterns. Therefore, it is difficult to envision their crystallization during the short deposition and subsequent surface cleaning process.

In all cases, the analyte gases being sensed are brought to the hybrid surface after entrainment in UHP nitrogen (Matheson 99.999+%) at room temperature. The system is purged for a minimum of 30 minutes before use with this UHP nitrogen. The typical resistances for the base PS structures range between 300 and 500 ohms at room temperature. The results presented in Table 2 (Ex. 3) are, in all cases, given relative to a base PS micro/nanoporous structure, tested prior to nanostructure deposition at room temperature. All of the nanostructure treated PS interfaces were tested exclusively at room temperature.

References of Example 3, each of which is incorporated herein by reference
[1] L. Seals, L.A. Tse, P. J. Hesketh, J. L. Gole, *J. Appl. Phys.* 2002, 91, 25192523.
[2] (a) S. Lewis, J. DeBoer, J. L. Gole, P. Hesketh, *Sens. Actuators, B, Chem* 2005, 110, 54-65. (b) J. L. Gole, J. L.; Lewis, S.; S. Lee, *Phys. Stat. Sol. A* 2007, 204, 1417-22 and references therein.
[3] (a) J. L. Gole, *MRS Bulletin* 2003, 28, 263. (b) G. Korotcenkov and B. K. Chou, Critical Reviews in Solid State and Materials Science, 35, 1, 1-37 (2010)
[4] (a) S. Ozdemir, J. L. Gole, *Chem. Sens.* 8: *Chem (Gas, Ion, Bio) Sens. and Analytical Systems, ECS Transactions* 2008, 16(11), 379-387. (b) J. L. Gole, J. Corno, S. Ozdemir, S. Prokes, H-C Shin, *Phys. Stat. Sol. C,* 2009, 6, 1773-1776.
[5] See for example
  (a) R. G. Pearson, *Coordin. Chem. Rev.* 1990, 100, 403-25.
  (b) R. G Pearson, J. Am. Chem. Soc. 1963, 85, 3533-3539.
  (c) R. G Pearson, Chemical Hardness, John Wiley VCH, Weinheim, 1997.
  (d) R. G Pearson, *J. Chem. Sci.* 2005, 117(5), 369-377.
  (e) R. G Pearson, *Inorg. Chem.* 1988, 27, 734-740.
[6] R. G Parr, R. G Pearson, *J. Am. Chem. Soc.* 1983, 105, 7512-7516.
[7] (a) R. G Parr, W. Yang. Density Functional Theory of Atoms and Molecules, Oxford University Press, New York, 1989. (b) Geerlings, P.; De Proft, F.; Langenaeker, W. *Chem. Rev.* 2003, 109, 1793.
[8] M. H. Cohen, A. Wasserman, *J. Phys. Chem.* 2007, 111, 2229-2242
[9] C. G. Zhan, J. A. Nichols, D. A. Dixon, *J. Phys. Chem. A* 2003, 107(20), 4184-4195.
[10] R. G. Parr, R. A. Donnelly, M. Levy, W. E. Palke, *J. Chem. Phys.* 1978, 68, 3801.
[11] R. G. Parr, R. G. Pearson. *J. Am. Chem. Soc.* 1983, 105, 7512.
[12] W. Yang, R. G. Parr, *Proc. Natl. Acad. Sci. USA,* 1985, 82, 6723.
[13] (a) W. Yang; R. G. Parr, R. Pucci, *J. Chem. Phys.* 1984, 81, 2862. (b) R. G. Parr, W. J. Yang, *J. Am. Chem. Soc.* 1984, 106, 4049.
[14] K. Fukui; T. Yonezawa, H. Shingu, *J. Chem. Phys.* 1952, 20, 722.
[15] P. Politzer, *J. Chem. Phys.* 1987, 86, 1072.
[16] J. L. Gole, A. G. Fedorov, P. Hesketh, C. Burda, *Phys. Stat. Sol. (C)* 1(S2) 2004, S188-197.
[17] A. Foucaran; F. Pascalk-Delannoy, A. Giani, A. Sackda, Commette, P. Boyer, *Thin Sol. Films* 1997, 297, 317.
[18] P. T. Moseley, *Meas. Sci. Technol.* 1997, 8, 223.
[19] I. Schechter; M. Ben-Chorin; A. Kuz, *Anal. Chem.* 1995, 67, 3727.
[20] (a) J. L. Gole; S. E. Lewis, *SPIE-Proceedings,* 2005, 5732:573-583. (b) J. L. Gole, S. E. Lewis, A. Fedorov, Prokes, *SPIE-Proceedings* 2005, 1-12:5929-08. (c) S. Ozdemir, J. L. Gole, Current Opinion in Solid State and Materials Science, 2007, 11, 92-100. See also Ref 3 (b).

[21] S. Ozdemir, J. L. Gole, A Phosphine detection matrix using nanostructure modified porous silicon gas sensors, submitted to Sensors and Actuators B: Chem submitted.

[22] J. L. Gole, A general approach to creating selective metal coatings at a nano-microporous porous silicon interface for sensor applications, 2006a, Continuation in part, patent Applied for.

[23] J. L. Gole, M. G. White, T-H Wang, C. Watkins, S. C. Street; D. A. Dixon, The surprising oxidation state of fumed silica and the nature of water binding to silicon oxides and hydroxides, submitted.

[24] S. Ozdemir, J. L. Gole unpublished.

[25] J. Janata, *Solid State Chemical Sensors*, 1985 Huber (Editor). P. T. Moseley, B. C. Tofield *Solid State Gas Sensors* 1987 Adam Hilger Series on Sensors. M. J. Madou, S. R. Morrison *Chemical Sensing with Solid State Devices* 1989.

[26] The porous silicon surface is believed to consist of silicon oxides and silicon oxyhydrides. J, L. Gole, E. C. Egeberg; E. Veje, A. Ferreira da Silva, I. Pepe, D. A. Dixon, *J. Phys. Chem. B* 2006, 110, 2064.

[27] S. E. Lewis; J. R. DeBoer; J. L. Gole, *Sensors and Actuators B: Chemical* 2007, 122:20-29.

[28] D. A. Dixon, private communication. J. L. Gole and D. A. Dixon, unpublished.

[29] P. A. Kottke; P. A. Fedorov, J. L. Gole, Springer, *Modern Aspects of Electrochemistry*, 43, M. Schlesinger editor, 2008, pp. 139-168.

[30] M. Schlesinger, M. Paunovic (Eds.), Modern Electroplating (4$^{th}$ Ed.), Wiley, New York, 2000.

[31] Modification of procedures in H. M. Van Noort, B. C. M Meenderink, and A. J. Molenaar, J. Electrochem. Soc., 133 (1986) 263-5, by L. Seals and J. L. Gole.

[32] E. K. Yunh, L. T. Romankiew, R. C. Alkire, J. Electrochem. Soc. 136 (1989) 206-15.

[33] L. Seals, private communication, Ph.D Thesis, Georgia Institute of Technology, 2002

[34] D. S. Horn, G. L. Messing, J. Am. Ceram. Soc., 72 (1989) 1719-21.

[35] (a) X. B. Chen, Y. B. Lou, A. C. S. Samia, C. Burda, J. L. Gole, Adv. Func. Mater., 2005, 15, 41-49. (b) A. F. da Silva, I. Pepe, J. L. Gole, S. A. Thomas, R. Palomino, W. M. Azevedo, E. F. da Silva Jr., R. Ahuja, C. Persson, Appl. Surf. Sci. 252 (2006) 5365.

[36] J. L. Gole, S. M. Prokes, J. D. Stout, O. J. Glembocki, R. S. Yang, Adv Mater, 2006, 18, 664.

Example 4

Abstract

We discuss the selective modification of porous silicon (PS) conductometric gas sensors for phosphine detection. Tin, nickel, copper and gold are electrolessly deposited onto nanopore covered microporous porous silicon surfaces forming $SnO_x$, NiO, $Cu_xO$ and $Au_xO$ nanostructured centers. Further studies have also been carried out with nanostructured alumina coated porous silicon. The porous silicon surface is analyzed for the metal oxides considered using XPS measurements. These experiments demonstrate that the indicated metals are deposited to the nanopore covered micropores of the PS interface and are oxidized to form metal oxide sites. The sensitivity change of these modified porous silicon gas sensor surfaces has been measured under 1-5 ppm $PH_3$ exposure. An improved sensitivity, of the order of 5 times that of untreated porous silicon, for 1 ppm exposure is observed. The selection of the nanostructure deposition is based on the hard to soft acid character of the nanostructured deposit and its subsequent effect on the physisorption of $PH_3$, an intermediate base. The observed behavior follows an inverse pattern IHSAB to the hard soft acid-base concept.

Introduction

Porous silicon (PS) has drawn considerable attention since the discovery of apparent quantum effects in its UV induced visible light emission [1] and [2]. The large surface area intrinsic to PS and the activity of the porous silicon layer to changes in the surrounding environment suggest PS as a gas sensor candidate among a variety of additional applications. The gas sensing properties of PS have been studied widely and different sensor designs and operation principles have been proposed [3], [4], [5], [6], [7], [8], [9] and [10]. Humidity, organic solvents, CO, $NO_x$, $NH_3$, $O_2$, $H_2$, HCl, $SO_2$, $H_2S$ and $PH_3$ have been detected using PS gas sensors at or below ppm levels.

Porous silicon gas sensors exhibit important characteristics for wide application. They can be operated over a broad range of environmental temperature, pressure, and humidity fluctuations as it is possible to eliminate response variations due to such environmental factors by operating in a gas pulsing mode [11]. These sensors can show high sensitivity and selectivity when designed with a micro/nanoporous hybrid pore structure. Since Si processing is well known in the semiconductor industry, it is easy to integrate porous Si with current CMOS/MEMS technologies reducing the cost of devices [12]. Although a conductometric PS gas sensor is sensitive to a variety of gases, considerable research on cross selectivity/ gas mixture detection is still required in order that quantitative multiple gas sensing can be accomplished. This requirement suggests that as simple a matrix of distinct sensor responses as possible be obtained with limited requirements for the modification of sensitivity. With this goal, we have focused on the application of simple nanostructured deposits on a hybrid PS interface to significantly change the interface sensitivity. The application of nanostructured metals, metal oxides, and nanoparticle catalytic coatings promotes considerable enhancement of the PS interface sensitivity. We have developed nanopore covered microporous Si surfaces subsequently treated with minimal procedures to form nanoparticle and cluster deposited surfaces that can be used in combination to form gas sensor arrays. To facilitate this array design, a better understanding of the selection of nanostructured materials to modify the PS framework is necessary. An approach to predict significant changes in sensor surface response for a variety of gases, based on a modification of the concept of hard and soft acid and base interactions, has been investigated here by testing the sensitivity of several nanostructure modified interfaces.

Phosphine is an extremely toxic gas widely used in agriculture for fumigation [13]. It is the only widely used fumigant that kills insects rapidly without leaving residues on the product. An additional application area is in the semiconductor industry as a dopant in silicon processing. It is also an illicit product of methamphetamine (meth) labs [14]. There is a recent considerable need for locating the signatures of illegal meth labs without breaking and entering the large number of small scale facilities increasing throughout the United States. The Occupational Safety and Health Administration (OSHA) sets a limit of exposure of 0.3 parts per million (ppm) $PH_3$ for an 8 h workshift, 40 h a week [15]. In this study, we have used a PS gas sensor to detect $PH_3$ and investigate response variations as a result of the deposition of nanostructured metal oxide coatings.

Experimental

Porous silicon interfaces were generated by electrochemical anodization of 7-13 Ω cm, p type (boron doped), (100)

silicon wafers (Siltronix). The anodization is done in 1 M $H_2O$, 1 M HF and 0.1 M tetrabutylammonium perchlorate (TBAP) in acetonitrile (MeCN) at 3 mA/cm$^2$. The process results in a nanopore coated microporous structure [16] and [17]. (In this study, we define pores of dimension 1-100 nm as nanopores and pores >0.5 μm in diameter as micropores.) After the anodized sample is cleaned in acetonitrile for 10 min to purge any residue in the pores from the etch solution, it is immersed in dilute HF and then placed in MeOH. The porous film has a typical porosity of 50-80%, the pore diameter varies from 1 to 2 μm and the typical pore depth is 10-30 μm (FIG. 5.1) [16]. The micropores are cylindrical in shape with a conical termination at the c-Si interface of the anodized wafer.

Before anodization, the Si surface is cleaned in HF (49%) and a SiC layer 1000 Å in thickness is coated onto the polished surface of the silicon wafer by plasma enhanced chemical vapor deposition (PECVD). SiC is used since this layer is highly durable in HF-based solutions [18]. 2 mm×5 mm windows were opened in the SiC layer by reactive ion etching (RIE). After the anodization process, a gold layer (3500-5000 Å) is coated onto the sensor by an e-beam evaporation method as depicted in FIG. 5.2. The conductometric PS gas sensors typically operate in the 1-5 V range, but it is possible to use the sensors with a 100 mV or smaller bias voltage [16].

In order to obtain a tin oxide nanostructured deposition on the PS interface, an electroless tin coating is formed from 0.33 M tin chloride, 1.92 M sodium hydroxide, and 0.66 M sodium citrate mixed at 70° C. [19]. The solution is stirred until it cools to room temperature. Porous Si is immersed into the solution for 25 s in order to obtain the desired $SnO_2$ coating. After immersion, it is placed in DI $H_2O$ and MeOH for consecutive 30 s periods. An electroless copper solution is prepared from $CuSO_4.5H_2O$ (0.76 g), sodium tartrate (4.92 g), formaldehyde (2 mL 0.27 M formaldehyde), and NaOH (0.8 g) diluted to 200 mL in deionized (DI) water [20]. Porous Si sensors are again dipped into the electroless solution for 30 s and then again placed in DI $H_2O$ and MeOH for about 30 s. The electroless nickel solution [21] contains nickel chloride (20 g/L) as the nickel source, sodium hydroxide (40 g/L) as a complexing agent, sodium borohydride (0.67 g/L) as a reducing agent, and ethylene diamine (44 g/L) as the stabilizer. PS is exposed to the electroless Ni solution for 25 s, then placed in DI $H_2O$ and MeOH, each for about 30 s. For the electroless gold coating [22], we have used a commercially available electroless gold metallization solution (Transene) and treated the sensor for 30 s. Afterwards the sensor was cleaned with DI water and MeOH.

For each nanostructured deposit, instead of forming a film on the porous surface, islands of nanostructured metal oxides are formed with an emphasis on short duration exposures to the electroless solutions. Alumina nanostructures were deposited directly to the PS interface. The $Al_2O_3$ nanocoating was prepared [23] using Boehmite (Wako Chemicals). Here, 0.1 g of Boehmite $(AlO(OH).nH_2O)$ was mixed with 100 ml of DI water and the pH adjusted to 4.5 by adding a few drops of $HNO_3$. The solution was stirred at 40° C. for about 10 days as, each day, the pH was additionally adjusted with $HNO_3$. After this stabilization, the sensors were coated for 1 min by immersing them into the prepared solution. The Boehmite coated sensor was then heated at 400° C. in an 100 sccm $O_2$ flow at 300 Torr for 4 h to convert the Boehmite to γ-$Al_2O_3$.

Surface Analysis

We have examined the PS interface after the electroless depositions used to deposit metal-based nanostructures to the PS surfaces. We have observed (SEM) that the walls between the micropores (FIG. 5.1A) decrease in thickness by less than 20% after a 10 min exposure to the electroless tin solution. This observation suggests that the total surface area of the porous network may increase even after much shorter treatments. The nanopore dimensions are not uniform on the surface. SEM analysis shows that the nanopore radius varies from 10's of nanometers to a few 100 nm (FIGS. 5.1C and D). We have carried out gas flow simulations in order to define an average characteristic length scale in this nano/micro regime. This analysis fits well to the sensor response data. The surface roughening and deformation are not easy to observe after the short duration of the electroless solution treatments (≤30 s) used in this study. Further, we are not able to establish whether or not a gestation period is necessary for any hydroxide etch in these systems. The nanoparticles deposited on the surface are clearly observed via SEM analysis (FIG. 5.3) [17]. Further the gas testing experiments are carried out at sufficiently low concentrations of $PH_3$ so as not to saturate the sensor with the test gas.

XPS measurements on the nanostructure deposited sensors are shown in (FIG. 5.4) and (FIG. 5.5). All of the XPS measurements are done using a Thermo K-Alpha XPS system. The X-ray source is Al Kα and the spot size is 400 μm$^2$. Each scan is repeated 10 times. For charge compensation, an electron flood gun is used. The experiments are conducted at pressures below 10$^{-8}$ mbar. FIG. 5.4(A) depicts the XPS spectrum of a dominantly $SnO_x$ nanostructure deposited PS surface. SnO ($Sn^{2+}$) has peaks in the range of 485.6-487.0 eV, $SnO_2$ ($Sn^{4+}$) has peaks in the range of 486.1-487.1 eV. There are also $Sn^{2+}$ and $Sn^{4+}$ peaks located in the range 487.0-488.0 eV [24]. These data are therefore consistent with the deposition to and oxidation of tin nanoparticles which are deposited and rapidly oxidized on the PS surface. FIG. 5.4B depicts the XPS spectrum for Ni nanostructure deposition. Nickel has an oxidation peak ($2p_{1/2}$) located ~871.8 eV for NiO ($Ni^{2+}$) and has peaks ($2p_{3/2}$) in the range of 853.6-857.2 eV. $Ni_2O_3$ ($Ni^{3+}$) shows peaks ($2p_{3/2}$) from 855.8-856.5 eV [24]. Thus the observed XPS spectrum is consistent with the deposition and oxidation of nickel nanoparticles. FIG. 5.4C depicts the XPS spectrum for a dominantly $Cu_xO$ nanoparticle deposition. CuO ($Cu^{2+}$) has peaks ($2p_{1/2}$) in the range 952.5-952.7 eV and has peaks ($2p_{3/2}$) in the range 933.3-934.3 eV. $Cu_2O$ ($Cu^{1+}$) has peaks in the range 932.0-932.8 eV [24]. Thus, this spectrum demonstrates the deposition to and oxidation of copper nanoparticles at the PS surface. The observed Au $4f_{5/2}$ and $4f_{7/2}$ doublets and curve fit to the experimental data for the XPS spectrum obtained for gold deposition are depicted in FIG. 5.4D [24].

The corresponding O 1 s spectra associated with the PS surface and the Sn 3d, Ni 2p, Cu 2p, and Au 4f XPS data in FIG. 5.4A to D are depicted in FIG. 5.5. There are several important characteristics of these O 1 s spectra. The peaks are quite symmetric; in other words, we observe no clear shoulder features at the higher (or lower) binding energy side of the O 1 s features associated with copper, nickel, or tin which might be correlated with the significant presence of OH groups [24] and [25] (and water). Further, the NIST data compilation [24] suggests that surface-layer OH binding energies should well exceed those of the oxides. The most recent data for the OH binding energy peaks associated with $H_2O$ suggest values of 534.8 [26] and 538 eV [27]. Further, in a very interesting recent article on hydroxylated nickel oxide (111), Ciston et al. [28] note a significant shoulder in their O 1 s XPS spectrum, to higher binding energy, which they associate with OH. In correlation with the data in FIG. 5.4A to C, it is suggested that the XPS spectra are to be attributed to oxidation dominated by the formation of metal oxide nanoparticles on the PS surface. It is further to be noted that the O 1 s spectra in FIG. 5.5 are shifted in the order gold≈tin>nickel>copper. This suggests that the spectral shifts cannot be correlated with the degree of oxidation but rather with the positioning and accessibility of the interactive nanostructured oxides on the walls of the nanopore covered microporous array (FIG. 5.3) associated with PS [29]. The O 1 s XPS spectrum of the native silica coating associated with PS is notably weaker and shifted to somewhat lower binding energy. This, we suggest, should be attributed to the more accessible nature of the metal oxides and gold clustered oxide deposits to the PS surface [17] and [29].

XPS measurements of both treated and untreated PS surfaces show virtually identical C peaks due to $CH_3OH$ treatment at various steps of the sensor fabrication and exposure to reproducible concentrations of hydrocarbons in the hood environment in which the sensors are tested, suggesting that the changes in sensitivity observed in the present study, which we outline below, cannot be associated with a variable sensitivity of these hydrocarbons to the analytes considered. The XPS spectra are consistent with a pronounced oxidation of the Ni, Cu, and Sn nanoparticle depositions. In contrast the XPS spectra obtained for Au are consistent with a much milder oxidation and the formation of the gold clustered oxides, $Au_xO$.

The sensor testing experiments are performed in a chemical hood at room temperature, atmospheric pressure, and virtually constant humidity. Our objective is to use PS sensors to detect hazardous gas mixtures in cleansed air with a sensor array format of various nanoparticle depositions. More detailed information about the evaluation of PS sensors tested under various conditions can be found in a recent review by Korotcenkov and Cho [30]. $PH_3$ (1000 ppm diluted in $N_2$—Matheson) is diluted to the specific desired concentrations via mixing with ultra high purity (UHP) $N_2$ (Matheson 99.999%) employing computer controlled mass flow controllers. Microprobes are utilized to measure the resistance change of the sensors when different concentrations of nitrogen entrained $PH_3$ are pulsed onto the sensor (FIG. 5.1 to 5.3) at room temperature. Each sensor is tested before and after electroless deposition. The base resistance of the sensor is typically a few hundred ohms, but can range to a few kΩ. The surface of the sensor is flushed with UHP $N_2$ for 30 min-1 h to assure base resistance stabilization at the beginning of each experiment. Further, the data in FIG. 5.5 for the O 1 s XPS peak demonstrate an extremely low OH concentration. This may result from the hydrophobic nature of the PS surface [31] and the nature of limited nanostructure deposits to this surface. One might envision these nanostructured islands (FIG. 5.3) as enhancing sites for the dominantly PS structure.

Results

We summarize the response change after $SnO_x$, NiO, $Cu_xO$ and $Au_xO$ nanostructures are deposited to the native PS interface in FIG. 5.9A to D, respectively. Since there are OH groups and hydrocarbons originating from the air deposited onto the sensor surface, we always perform relative measurements, comparing the untreated PS sensor and nanoparticle deposited PS. These relative measurements are depicted in FIG. 5.9. Following a base resistance stabilization with a greater than atmospheric pressure $N_2$ flow for 30-60 min at room temperature, $PH_3$ is pulsed onto the sensor every 300 s in half cycles. The UHP $N_2$ purge for extended periods at a base stabilized resistance suggests that water condensation on the PS surface is at a minimum. The $N_2$ flow onto the sensor is kept constant at 100 sccm at all times during the experiment and diluted $PH_3$ is mixed with the $N_2$ flow as we test the sensor response to phosphine. The peaks in FIG. 5.9 correspond to an exposure to 1, 2, 3, 4, and 5 ppm of test gas, respectively.

After the 300 s half cycle, we cease flowing $PH_3$ onto the sensor and refresh the surface with UHP nitrogen, decreasing the resistance of the PS layer as a result. All sensors are evaluated in an unsaturated mode since the time scale for reversibility may become an issue in a long term saturated mode and these longer term exposures are not necessary. Although we operate the sensors in an unsaturated mode, the sensor response and recovery times are distinctly different and full time recovery from the gas exposure takes longer than 300 s, the exposure time duration in the present configuration (FIG. 5.10 [16]). However, the onset of the sensor response remains clearly visible. This behavior suggests that the $PH_3$ response on PS is that of a 'sticky' gas whose interaction may be dominated by physisorption but which also displays weak chemisorption. Purging the sensor surface with UHP $N_2$ for longer durations improves the gradual shift to the initial base line. The return to baseline can also be further improved by more tightly constraining the gas flow path to the sensor surface [29].

We have observed an increase in response with respect to PS for all of the nanostructured deposits, with the exception of $Al_2O_3$, as they form interactive nanostructured oxides on the PS surface. However, the responses for each deposit are distinct and do not have the same magnitude for the same concentration of the tested gas. This feature allows us to begin to develop a selectivity matrix for the PS gas sensor, $PH_3$ detection. For a 1 ppm exposure, the amount of resistance change per base resistance for the nanostructure deposited and untreated sensors, Equation 1, is summarized in Table 1, Ex. 4. The maximum enhancement per base resistance (a factor of approximately 5) is observed when the PS sensor is treated with electroless gold to form $Au_xO$ deposits. The minimum change in relative resistance results from the use of the $Al_2O_3$ followed by the most investigated gas sensing material, tin oxide. The relative response of the hybrid PS structure and an initially generated "$Al_2O_3$" nanostructure treated surface (see Section 2) appear to be virtually identical (Table 1, Ex. 4).

$$\Delta = \frac{\Delta R(\text{coated})/R_0(\text{coated})}{\Delta R(\text{uncoated})/R_0(\text{uncoated})} \quad \text{(Equation 1)}$$

TABLE 1

Ex. 4. Approximate response increase (Eq. (1)) for different catalytic metal coatings for 1 ppm exposure to $PH_3$.

| Deposits | $SnO_2$ | $Al_2O_3$ | NiO | $Cu_xO$ | $Au_xO$ |
|---|---|---|---|---|---|
| $\Delta_{1\,ppm}$ | 2 | 1 | 2.5 | 4 | 5 |

For this series of experiments, the tin and gold treated PS surfaces (formation of $SnO_x$ and $Au_xO$), base resistance change after surface modification is of the order of 50Ω for the PS surface prepared in this study. We find that the formed NiO deposited sensor shows a large increase in base resistance. In contrast, the copper deposition levels used in the present experiments lower the base resistance of the sensor by approximately 50Ω. This could indicate a $Cu_xO$ coating at too high a concentration on the porous layer and demonstrates the importance of controlling the nanostructure deposition to a low level. This can be accomplished by varying the duration of the immersion of the sensor in the electroless copper solution (typically a time scale of tens of seconds). By analyzing the change in the base resistance drift, it is also possible to determine the necessary exposure for electroless metal deposition (the desired $Cu_xO$ nanostructure concentration for a given base PS structure).

We have defined the sensitivity as the slope of the response per initial base resistance [16] of the PS layer and summarized the results for each of the considered electroless deposits for 1-5 ppm $PH_3$ exposure in FIG. 5.6. To the 3 ppm level, the sensitivity is approximately linear for all of the nanostructured coatings exposed to $PH_3$. At higher concentrations, the sensitivity begins to level off and decrease. This behavior suggests that the nanostructured coatings are most effective at lower concentrations and that they appear to display an irreversible degradation at higher concentrations of $PH_3$, which might, in fact, be the result of sensor poisoning due to strong chemisorption. The sensor response is primarily proportional to the strength of the interaction between the metal depositions on the PS interface and $PH_3$, whereas the reversibility of the response is inversely proportional to this interaction. Although the sensitivity inherent to the $Cu_xO$ coating seems to reach higher levels with an increase in $PH_3$ gas concentration as shown in FIG. 5.6, the $Au_xO$ coating is a better candidate for $PH_3$ detection. This follows from the behavior recorded in FIG. 5.6C where the drift in the average resistance increases drastically, implying a notable decrease of reversibility with increasing concentration. These results suggest that it is more practical to use the tuning of interspersed nanoparticle/cluster deposits on the PS surface so as to adjust response strength and ease of reversibility, and that this tuning has associated with it an optimum nanostructured oxide concentration.

Discussion

Metal Oxide Nanostructure Deposit Selection

The XPS data presented in FIG. 5.4 and FIG. 5.5 demonstrates clear evidence for the oxidation of metal nanostructure deposits on the PS surface. With the treatments employed in the present study, it might be argued that the oxidized, deposited, metal-based nanostructure islands [17] and [29] correspond to metal oxides that are not accessible due to a combined oxide-surface hydroxide coating. However, a surface completely coated (covered) with hydroxide ions so as to block the exposure of an oxidized metal will nullify the effect of the corresponding metal oxides rendering moot the observation of clearly dominant changes in sensitivity. In other words, (1) there should be little or no differences in the responses to different analyte gases and (2) a completely OH(-) covered surface should act to repel basic analytes, considerably decreasing the response to their presence.

Nanostructured metal oxide treatments to modify the surface activity of PS have been employed to modify the physisorption/weak chemisorption for a PS gas sensor. In order to explain this behavior, we have developed a complementary concept to that formulated by Pearson [32] for hard and soft acid base (IHSAB) interactions. In the HSAB concept [32], which was developed for aqueous solutions, the interaction strength is correlated with the relative acidity and basicity of several surveyed reactants which are exemplified in Table 2, Ex. 4. The ions and molecules indicated in this table, as they interact to form complexes and molecules are classified as strong, borderline, or weak acids and bases dependent on their binding as ligands. Hard species, both acids and bases, tend to be small slightly polarizable species and soft acids and bases tend to be larger and more polarizable. Further, the Pearson principle states that strong acids react with strong bases and weak acids interact with weak bases, resulting in significant ionic and covalent bonding, respectively. In contrast, we have found that the nanostructure treated PS gas sensor behaves in the physisorption/weak chemisorption regime, and we have developed an inverse IHSAB concept to explain this behavior in a recent study [29]. Here, the physisorption process is found to dominate for primarily strong acid-weak base and weak acid-strong base interactions. By assessing these trends in IHSAB, a first order selection can be made for the appropriate modification of the porous Si hybrid interface with nanostructured metal/metal oxide deposits to create a range of sensitivities for a number of gases.

TABLE 2

Some examples of hard and soft acids and bases.

|  | Hard | Borderline | Soft |
| --- | --- | --- | --- |
| Acids | $H^{+*}$, $Li^+$, $Na^+$, $K^+$, $Be^{2+}$, $Mg^{2+}$, $Ca^{2+}$, $Cr^{2+}$, $Cr^{3+}$, $Al^{3+}$, $SO_3$, $BF_3$, $Sn^{4+}$, $Ti^{4+}$ | $Fe^{2+}$, $Co^{2+}$, $Ni^{2+}$, $Cu^{2+}$, $Zn^{2+}$, $Pb^{2+}$, $SO_2$, $BBr_3$, $Sn^{2+}$, $NO_2$ | $Cu^+$, $Au^+$, $Ag^+$, $Tl^+$, $Hg^+$, $Pb^{2+}$, $Pt^{2+}$, $Hg^{2+}$, $BH_3$ |
| Bases | $F^-$, $OH^-$, $H_2O$, $NH_3$, $PH_3$ | $NO_2^-$, $Br^-$ | $H^-$, $R^-$, $CN^-$, $CO$, $I^-$ |

This (*) standard notation does not indicate an ion, but rather the effective charge of elements bound to a ligand. For example $SiO_2$ corresponds to $Si^{4+}$ and $SiO$ corresponds to $Si^{2+}$.

$PH_3$ is a moderately hard base. Thus, its position among the bases is indicated in Table 2, Ex. 4. Table 2, Ex. 4 summarizes primarily the acid-base strength of ions associated with the oxides. From this table, the inverse HSAB model suggests that $PH_3$ will give the best reversible response with $Au_xO$ and $Cu_xO$ deposits since $Cu^+$ and $Au^+$ are weak acids. $Ni^{2+}O$, a borderline acid ($Ni^{2+}$), provides a decreased response as it lies closer to $PH_3$, however this response is notably better than that for $Al_2O_3$ ($Al^{3+}$). The NiO response is also greater than that for $Sn^{4+}O_2$, however, the response to $SnO_2$ exceeds that for $Al_2O_3$ as the $Al^{3+}$ ion represents a weaker acid which is even closer to $PH_3$. The inverse HSAB model [29] suggests that the proper combination of nanocoating techniques could be employed to produce combinations of array based multiple sensor devices of varying sensitivity to a variety of gases and that a matrix of array responses can be correlated to selectivity for a given gas mixture.

Comparison to Previous Studies

The results we obtain in this study suggest the importance of gold clustered oxide nanostructures for the detection of $PH_3$ and correlate well with the observations of Nakano and Ogawa [33], made in the preparation of thin gold film electrodes for electrochemical sensors for phosphine and arsine. However, the present sensors are far more easily constructed than those obtained from ion plating into the surface of a polytetrafluoroethylene (PTFE) membrane. In concert with the results we have obtained previously for ammonia [34], the range of behaviors which we observe for phosphine with $SnO_2$ ($Sn^{4+}$), $Al_2O_3$ ($Al^{3+}$), NiO ($Ni^{2+}$), $Cu_xO$ ($Cu^{1+,2+}$), and $Au_xO$ ($Au^{0,1+}$) correlates well with the relative gas basicity of phosphine and ammonia which have measured proton affinities of 185±4 [35] and 207 kcal/mol [36].

We suggest that a matrix of distinct and separable responses for $PH_3$ can be generated using the relatively simple deposition techniques that we have outlined and that this approach presents a cost effecting alternate to the more complicated copper [37] and combined zirconium-palladium doping of $SnO_2$ films [38]. The former study with copper is likely influenced by the known sensitivity of copper for phosphine used in fumigation. Further, the present studies demonstrate that alumina or the alumino silicates may not present surfaces which are as promising as those nanostructured metal oxide coatings whose response is depicted in FIG. 5.9. The data in Table 2, Ex. 4, in fact, suggest that $Sn^{4+}$ should represent a more sensitive nanostructured coating than $Al^{3+}$ to phosphine as the acidic character of $Al^{3+}$ more closely matches the basic character of $PH_3$ [29]. Thus, a stronger chemisorption by the $Al_2O_3$ seeded surface can compete with reversible physisorption.

FIG. 5.7 illustrates the 1 ppm response of untreated and $SnO_2$ nanostructure treated PS to NO. The first region corresponds to an $N_2$ purge for base resistance stabilization until NO is introduced. Upon exposure to NO, a sharp decrease in resistance occurs due to the treatment formation of $NO_2$. After saturation of the O atom concentration on the PS or $SnO_x$ treated PS surface, the signal increases in resistance as NO is detected. After 300 s of exposure, NO is turned off and the surface is purged with $N_2$. Note the scales to left (PS) and right (treated PS).

FIG. 5.8A illustrates the sensitivity test for 1, 2, 3, 4, 5 ppm $NH_3$, FIG. 5.8B) 1-5 ppm $PH_3$, and FIG. 5.8C) 5 ppm NO. The first region (600 s in the $NH_3$ and NO response and 300 s in the $PH_3$ response) corresponds to the $N_2$ purge of the sensor (in an open configuration) to obtain the optimal return to baseline. The sensor is exposed to the test gas for 300 s followed by a cut-off for the next 300 s. This cycle is run for 1 hr. The nanostructure deposition on the PS surface is tin oxide. Additional details are described in Example 5.

Conclusion

A PS gas sensor has been used to detect $PH_3$ employing different nanostructured oxidized metal nanoparticle depositions. These depositions are verified with XPS measurements. We have achieved significant improvements in the sensor response when naked porous silicon is coated with $Au_xO$ and $Cu_xO$ nanostructures. The approach to a general oxidized metal deposition strategy is based upon an inverse IHSAB concept designed to create a dominant physisorption interaction for the modified PS interface.

Example 4 References, each of which is incorporated herein by reference

[1] L. T. Canham, Silicon quantum wire array fabrication by electrochemical and chemical dissolution of wafers, *Appl. Phys. Lett.* 57 (1990), pp. 1046-1048.

[2] V. Lehmann and U. Gosele, Porous silicon formation: a quantum wire effect, *Appl. Phys. Lett.* 58 (1991), pp. 856-858.

[3] L. Boarino, C. Baratto, F. Geobaldo, G. Amato, E. Comini, A. M. Rossi, G. Faglia, G. Lerondel and G. Sberveglieri, $NO_2$ monitoring at room temperature by a porous silicon sensor, *Mater. Sci. Eng. B Solid* 69-70 (2000), pp. 210-214.

[4] L. Seals, L. A. Tse, P. J. Hesketh and J. L. Gole, Rapid, reversible, sensitive porous silicon gas sensor, *J. Appl. Phys.* 91 (2002), pp. 2519-2523

[5] G. Barillaro, A. Diligenti, G. Marola and L. M. Strambini, A silicon crystalline resistor with an adsorbing porous layer as gas sensor, *Sens. Actuators B* 105 (2005), pp. 278-282.

[6] M. Archer, M. Christophersen and P. M. Fauchet, Electrical porous silicon chemical sensor for detection of organic solvents, *Sens. Actuators B* 106 (2005), pp. 347-357.

[7] M. Björkqvist, J. Paski, J. Salonen and V. Lehto, Studies on the hysteresis reduction in thermally carbonized porous silicon humidity sensor, *IEEE Sens. J.* 6 (2007), pp. 542-547.

[8] H. B. King, A. M. Ruminski, J. L. Snyder and M. J. Sailor, Optical fiber-mounted porous silicon photonic crystals for sensing organic vapor breakthrough in activated carbon, *Adv. Mater.* 19 (2007), pp. 4530-4534.

[9] L. D. Stefano, D. Alfieri, I. Rea, L. Rotiroti, K. Malecki and L. Moretti et al., An integrated pressure driven microsystem based on porous silicon for optical monitoring of gaseous and liquid substances, *Phys. Stat. Sol. A* 204 (2007), pp. 1459-1463.

[10] S. Ozdemir and J. L. Gole, The potential of porous silicon gas sensors, *Curr. Opin. Solid State Mater. Sci.* 11 (2007), pp. 92-100.

[11] S. Lewis, J. R. DeBoer and J. L. Gole, A pulsed system frequency analysis for device characterization and experimental design: application to porous silicon sensors and extension, *Sens. Actuators B* 122 (2007), pp. 20-29.

[12] M. J. Madou, Fundamentals of Microfabrication: The Science of Miniaturization (second ed.), CRC Press (2002).

[13] B. Berck, Sorption of phosphine vy cereal products, *J. Agric. Food Chem.* 16 (1968), pp. 415-419.

[14] J. L. Burgess, Phosphine exposure from a methamphetamine laboratory investigation, *J. Toxicol. Clin. Toxicol.* 39 (2001), pp. 165-168.

[15] Phosphine in workplace atmospheres, The Occupational Safety and Health Administration, January 2010, http://www.osha.gov/dts/sltc/methods/inorganic/id180/id180.html.

[16] S. Lewis, J. DeBoer, J. L. Gole and P. Hesketh, Sensitive, selective, and analytical improvements to a porous silicon gas sensor, *Sens. Actuators B* 110 (2005), pp. 54-65.

[17] J. L. Gole, S. Lewis and S. Lee, Nanostructures and porous silicon: activity at interfaces in sensors and photocatalytic reactors, *Phys. Stat. Sol. A* 204 (2007), pp. 1417-1422.

[18] A. G. Nassiopoulos, Local formation and patterning of porous silicon. In: L. Canham, Editor, *Properties of Porous Silicon*, IEE-Books, London (1997), pp. 77-80.

[19] Modification of procedures in H. M. Van Noort, B. C. M. Meenderink, A. J. Molenaar, In situ $^{119}$Sn conversion electron Mössbauer study of the surface of tin layers as deposited by an electroless process, J. Electrochem. Soc. 133 (1986) 263-265 by L. Seals and J. L. Gole.

[20] E. K. Yung, L. T. Romankiw and R. C. Alkire, Plating of copper into through-holes and vias, *J. Electrochem. Soc.* 136 (1989), pp. 206-215.

[21] L. Seals, private communication.

[22] (4th ed.) In: M. Schlesinger and M. Paunovic, Editors, *Modern Electroplating*, Wiley, New York (2000).

[23] D. S. Horn and G. L. Messing, Alumina monolith formation by flocculation of boehmite sols, *J. Am. Ceram. Soc.* 72 (1989), pp. 1719-1721.

[24] NIST X-ray Photoelectron Spectroscopy Database, Version 3.5 (National Institute of Standards and Technology, Gaithersburg, 2003) http://srdata.nist.gov/xps/.

[25] In: J. L. G. Fierro, Editor, *Metal Oxides: Chemistry and Applications*, CRC Taylor & Francis, Boca Raton, Fla. (2006).

[26] M. Lundholm, H. Siegbahn, S. Holmberg and M. Arbman, *J. Electron Spectrosc. Relat. Phenom.* 40 (1986), p. 163.

[27] J. Russat, *Surf. Interface Anal.* 11 (1988), p. 414.

[28] J. Ciston, A. Subramanian, D. M. Kienzle and L. D. Marks, *Surf. Sci.* 604 (2010), pp. 155-164.

[29] J. L. Gole and S. Ozdemir, Nanostructure directed physisorption vs. chemisorption at semiconductor interfaces: the inverse of the hard-soft acid-base (HSAB) concept, *ChemPhysChem* 11 (2010), pp. 2573-2581.

[30] G. Korotcenkov and B. K. Cho, Porous semiconductors: advanced material for gas sensor applications, *Crit. Rev. Solid State Mater. Sci.* 35 (2010), pp. 1-37.

[31] V. Zorba, L. Persano, D. Pisignano, A. Athanassiou, E. Stratakis, R. Cingolani, P. Tzanetakis and C. Fotakis, *Nanotechnology* 17 (2006), pp. 3234-3238

[32] R. G. Pearson, Hard soft acids and bases—the evolution of a chemical concept, *Coord. Chem. Rev.* 100 (1990), pp. 403-425.

[33] N. Nakano and S. Ogawa, Preparation of thin gold-film electrode for an electrochemical gas sensor for phosphine and arsine, *Sens. Actuators B* 21 (1994), pp. 51-55.

[34] S. Ozdemir and J. L. Gole, Porous silicon gas sensors for room temperature detection of ammonia and phosphine, *Chemical Sensors* 8: *Chemical (Gas, Ion, Bio) Sensors and Analytical Systems, ECS Transactions* vol. 16 (2008) pp. 379-387.

[35] D. Holtz and J. L. Beauchamp, Relative basicity of phosphine and ammonia in the gas phase, *J. Am. Chem. Soc.* 91 (1969), pp. 5913-5915.

[36] M. A. Haney and J. L. Franklin, Heats of formation of $H_3O^+$, $H_3S^+$, and $NH_4^+$ by electron impact, *J. Chem. Phys.* 50 (1969), pp. 2028-2031.

[37] T. Ratcheva, I. Stambolova and K. Konstantinov, Copper-doped $SnO_2$ thin films for $PH_3$ detection, *Thin Solid Films* 217 (1992), pp. 187-192.

[38] T. Ratcheva, I. Stambolova and K. Konstantinov, $PH_3$ detection by $SnO_2$—$ZrO_2$ thin films, *Sens. Actuators B* 21 (1994), pp. 199-204.

Example 5

Brief Introduction

Porous silicon (PS) conductometric gas sensors to create a sensitivity matrix for the room temperature detection of $NO_x$ ($NO$, $NO_2$). "P-type" nanopore coated microporous silicon is treated with tin, nickel, copper, and gold, electrolessly deposited onto the PS surface to form $SnO_x$, $NiO$, $Cu_xO$, and $Au_xO$ nanostructured centers as confirmed by XPS measurements. The relative sensitivities of these modified PS gas sensor surface sites have been measured under 1-5 ppm NO exposure. An improved sensitivity of up to 10 times that of untreated PS is observed for a 1 ppm exposure. Deposits are based on the hard to soft acid character of nanostructured metal oxide islands that are fractionally deposited on the semiconductor interface and their effect on the physisorption of NO, a weak base, dictated by an inverse pattern (IHSAB) to the hard-soft acid base concept. NO, a free radical, can interact with oxygen sites on the modified PS sensor interfaces, to produce a transient $NO_2$ signal unique to PS-based NO sensors, which is not observed as other basic analytes including $NH_3$, $PH_3$, $H_2S$, $SO_2$, and CO interact with "p-type" PS. A comparison is made between the current PS sensor systems which operate at room temperature and electrochemical and traditional metal oxide sensors.

Introduction

Previously, we have outlined an approach which combines the concepts of acid/base interaction and the properties of extrinsic semiconductors, suggesting a general procedure to optimally design sensors with improved and variable sensitivity for a variety of gases, operating at room temperature in an array-based format.[1-3] The IHSAB concept is designed to facilitate highly variable physisorbed surface interactions using a diversity of nanostructured "fractional" oxide depositions which form islands on a porous silicon interface. These islands act as antennas to focus the nature of the physisorbed surface-interface interaction, while minimizing the chemical interaction of an acidic or basic analyte with the semiconductor. We promote electron transfer to (base) or from (acid) the surface of an extrinsic semiconductor and an interaction with the majority carriers. Here, using "p-type" porous silicon, we apply this approach to a study of the weak base, NO, and the moderate acid, $NO_2$, which can be formed from the interaction of NO with oxygen.

NO and $NO_2$ play important roles in disease detection[4,5] and in vehicle exhaust emissions[6-15]. Methods for non-invasive disease detection can provide highly desirable clinical probes[4,5] and NO, in particular, that is predominantly generated in the bronchial system is a dominant indicator for asthmatic conditions and the inflammation which they cause. Further, the large quantities of NO produced in an asthmatic attack can combine with $O_2$ in breadth to produce $NO_2$. A simply constructed portable sensor capable of measuring significant NO (and $NO_2$) concentration changes in breath might be used on a regular basis to signify the onset of asthma attacks.

$NO_2$ also represents a toxic air pollutant emitted by combustion engines and has been the focus of several research efforts in sensor technology[6-17] where levels as low as 12 ppb in dry air and 50 ppb in humid air have been reported for a $p^+$ substrate-based porous silicon sensor[6].

In this Example, we demonstrate the development of an $NO(NO_2)$ detection matrix, creating an array of nanostructure modified "p-type" porous silicon gas sensors whose distinct sensitivities, in part, take advantage of the weak basic character of NO in contrast to the moderately strong acid character of $NO_2$. In the course of this study, we observe the result of the interaction of NO with oxygen sites, on several of the modified porous silicon sensor interfaces, in a process that would appear similar to, but distinct from, that previously reported[7,8] for thin film $SnO_2$ sensors, viz $$NO + SnO_2(O^-) \rightarrow SnO_2(NO_2^-) \quad (1)$$

$$SnO_2(NO_2^-) \rightarrow SnO_2(e^-) + NO_2 \quad (2)$$

The behavior associated with NO, a free radical weak base, is distinctly different from that of $NH_3$, $PH_3$, $H_2S$ and several additional basic analytes where the conductometric sensor signal does not indicate interaction with oxygen sites. We will suggest that this observed sensor behavior can be correlated by considering the coupling of acid/base theory with the properties of majority carriers in an extrinsic semiconductor[1,2].

Experimental

Porous silicon interfaces were generated by electrochemical anodization of 7-13 Ωcm, p type (boron doped), (100) silicon wafers (Siltronix). The anodization is done in 1M $H_2O$, 1M HF and 0.1 M tetrabutylammonium perchlorate (TBAP) in acetonitrile (MeCN) at 3 mA/cm². The process, discussed in detail elsewhere[3,18,19], results in a nanopore coated microporous structure. (Pores of dimension 1-100 nm are defined as nanopores and pores >0.5 μm in diameter as micropores). The anodized sample is cleaned in acetonitrile for 10 min to purge any residue in the pores from the etch solution. It is immersed in dilute HF and then placed in MeOH. Typical porosities are 50-80%, pore diameters vary from 1-2 μm, and the typical pore depth is 10-30 μm[3,18,19]. The micropores are cylindrical in shape with a conical termination at the c-silicon interface of the anodized wafer[20].

Before anodization, the silicon surface is cleaned in HF (49%) and a SiC layer 1000 Å in thickness is coated onto the polished surface of the silicon wafer by Plasma Enhanced Chemical Vapor Deposition (PECVD). SiC is used since this layer is highly durable in HF-based solutions[3,21]. 2 mm×5 mm windows are opened in the SiC layer by Reactive Ion Etching (RIE). After the anodization process, a gold layer (3500-5000 Å) is coated onto the sensor by an e-beam evaporation method[3,18,19]. The conductometric PS gas sensors typically operate in the 1-5 V range (See FIG. 5.10), however, it is possible to use the sensors with a 100 mV or smaller bias voltage[18].

In order to obtain a tin oxide nanostructured deposition on the PS interface, an electroless tin coating is formed from 0.33 M tin chloride, 1.92 M sodium hydroxide, and 0.66 M sodium citrate mixed at 70° C.[22]. The solution is stirred until it cools to room temperature. Porous silicon is immersed into the solution for 25 s in order to obtain the desired $SnO_2$ coating. After immersion, it is placed in DI $H_2O$ and MeOH for consecutive 30 sec periods. An electroless copper solution is prepared from $CuSO_4$-$5H_2O$ (0.76 gr), sodium tartrate (4.92 g), formaldehyde (2 mL 0.27 M formaldehyde), and NaOH (0.8 g) diluted to 200 mL in deionized (DI) water[23]. Porous silicon sensors are again dipped into the electroless solution for 30 s and then placed in DI $H_2O$ and MeOH for about 30 s. The electroless nickel solution[23] contains nickel chloride (20 g/L) as the nickel source, sodium hydroxide (40 g/L) as a complexing agent, sodium borohydride (0.67 g/L) as a reducing agent, and ethylene diamine (44 g/L) as the stabilizer. PS is exposed to the electroless Ni solution for 25 s, then placed in DI $H_2O$ and MeOH, each for about 30 s. For the electroless gold coating[24], we have used a commercially available electroless gold metallization solution (Transene) and coated the sensor for 30 s. Afterwards the sensor is cleaned with DI water and MeOH. For each nanostructured deposit, instead of forming a film on the PS surface, islands of nanostructured metal oxides are formed with an emphasis on short duration exposures to this surface[1,3,18,19].

We have examined the PS surface interface after the electroless depositions used to deposit metal-oxide nanostructures to the PS surfaces. The details of this study are outlined elsewhere[3]. We have also carried out gas flow simulations in order to define an average characteristic length scale in the micro/nano-regime using the sensor response data[25]. Although surface roughening and deformation is not easy to observe after the short duration of the electroless solution treatments (≤30 s) used in this study, the metal oxide nanoparticles deposited on the surface are clearly observed via SEM analysis[19]. Further, the gas testing experiments are carried out at sufficiently low NO concentrations so as not to saturate the sensors with the test gas[3].

Extensive XPS measurements have been carried out on the Cu, Ni, Sn, and Au nanostructured deposits to the PS surface[3] and on the O 1 s region. All of the XPS measurements were done using a Thermo K-Alpha XPS system. For charge compensation, an electron flood gun was used. The results of the XPS studies[3] are found to be consistent with a pronounced oxidation of the Ni, Cu, and Sn nanoparticle depositions. In contrast, the XPS spectra obtained for Au are consistent with a much milder oxidation and the formation of the gold clustered oxides, $Au_xO$ (x>>1). Further, no clear evidence is obtained for OH formation as exemplified by a significant shoulder in the O 1 s XPS spectrum, indicating the minimal presence of water[3]. This is consistent with the extensive purging of the system with UHP nitrogen before measurements are taken. Further, the presence of water vapor, a moderate base, will promote a considerable sensor response. XPS measurements of both treated and untreated PS surfaces show virtually identical C peaks due to (1) $CH_3OH$ treatment at various steps of the sensor fabrication and (2) exposure to reproducible concentrations of hydrocarbons in the hood environment in which the sensors are tested. This strongly suggests that the changes in sensitivity observed in the present study, which we outline below, cannot be associated with a variable sensitivity of the hydrocarbons to the analytes considered.

The sensor testing experiments[3,18,19] are performed in a chemical hood at room temperature, atmospheric pressure, and virtually constant humidity (See FIG. 5.10). Our objective is to use PS sensors to detect hazardous gas mixtures in cleansed air with a sensor array format of various nanoparticle depositions. More detailed information about the evaluation of PS sensors tested under various conditions can be found in Refs. 3, 18, and 19 and a recent review by Korotcenkov et al.[26]. NO (Matheson) is diluted to the specific desired concentrations via mixing with ultra high purity (UHP) $N_2$ (Matheson % 99.999) employing computer controlled mass flow controllers. Microprobes are utilized to measure the resistance change of the sensors when different concentrations of nitrogen entrained NO are pulsed onto the sensors at room temperature. Each sensor is tested before and after electroless deposition. The base resistance of the sensor is typically a few hundred ohms, but can range to a few kΩ. The surface of the sensor is flushed with UHP $N_2$ for 30 min-1 hr. prior to testing to assure base resistance stabilization at the beginning of each experiment.

Results

We summarize the response changes of a native porous silicon interface to NO in FIG. 6.1. Since there can be OH groups and hydrocarbons originating from the air deposited onto the sensor surface, we always perform relative measurements, comparing nanoparticle deposited PS with an untreated PS sensor. An $N_2$ flow onto the sensor is kept constant at 100 sccm at all times during the experiment and diluted NO is mixed with the $N_2$ flow as we test the sensor response to NO. The peaks in FIG. 6.1 correspond to an exposure to 1, 2, 3, 4, and 5 ppm of test gas. This recorded signal corresponds to 2 Ohms/ppm. The signal is exactly reproducible after 5 pulsing cycles. It is to be noted that the introduction of $NO_2$, a moderately strong acid, to the "p-type" PS surface used in this study leads to a significant drop in resistance as demonstrated in FIG. 6.2. These results will be correlated in following discussion.

We summarize the response changes to NO after $SnO_x$, NiO, $Cu_xO$, and $Au_xO$ nanostructures are deposited to the native PS interface in Table 1, Ex. 6, FIG. 6.3. We have observed a clear increase in the response for NO with respect to PS for the surfaces treated with nanostructured deposits of $SnO_x$, NiO, and $Au_xO$ (x>>1). $Cu_xO$, however, appears to offer little improvement. The responses for each deposit are distinct and do not have the same magnitude for the same concentration of the tested gas. This feature allows us to begin to develop a selectivity matrix for the PS gas sensor-NO detection. For a 1 ppm exposure, the amount of resistance change per base resistance for the nanostructure deposited vs. untreated sensors, Equation 3, is summarized in Table I, Example 6. The maximum enhancement per base resistance (a factor of approximately 7-10) is observed when the PS sensor is treated with electroless tin to form $SnO_x$ deposits on the PS surface. The minimum change in relative resistance results from the use of electroless copper and the formation of nanostructured $Cu_xO$ islands on the PS surface.

$$\Delta = \frac{\Delta R(\text{deposited})/R_0(\text{deposited})}{\Delta R(\text{untreated})/R_0(\text{untreated})} \quad (3)$$

TABLE I

Example 6. Approximate response increase (Eq. 3) for different catalytic metal oxide

| Deposits | $SnO_2$ | NiO | $Cu_xO$ | $Au_xO$ |
|---|---|---|---|---|
| $\Delta_{1\,ppm}$ | 7-10 | 3.5 | 1 | 1.5-2 |

We have defined the sensitivity as the slope of the response per initial resistance[18] of the treated PS layer and summarized the results for each of the nanostructured metal oxide deposits, for 1-5 ppm NO exposure, in Table 1, Ex. 6, FIG. 6.3.

The free radical nature of NO and the potential for the trapping of oxygen atoms on a semiconductor surface can provide an intriguing active environment. There are additional response changes as an NO gas flow is introduced to several $SnO_x$, NiO, $Cu_xO$, and $Au_xO$ nanostructure deposited PS interfaces. These relative measurements for the beginning of each NO introduction, are depicted in FIG. 6.3A-E. Following a base resistance stabilization with a greater than atmospheric pressure $N_2$ flow for 30-60 min. at room temperature, NO was pulsed onto the sensor every 300 s in half cycles. The UHP $N_2$ purge for extended periods at a base stabilized resistance suggests that water condensation on the PS surface is at a minimum. This is also suggested by the O 1 s XPS spectrum[3]. After a 300 s half cycle, we cease flowing NO onto the sensor and refresh the surface with UHP nitrogen. All sensors are evaluated in an "unsaturated mode" since the time scale for reversibility may become an issue in a long term saturated mode and these longer term exposures are not necessary. However, we have indicated the long term steady-state response as the sensor reaches saturation for the $SnO_x$ treated PS surface in FIG. 6.3E.

The data in FIG. 6.3A-E demonstrate a distinctly different initial response to NO than that observed for other basic gases including $NH_3$, $PH_3$, and $H_2S$. After an initial baseline stabilization, the introduction of NO, a weak base, at first produces a "surprising" sharp spike-like drop in resistance. This is followed by a gradual increase in the resistance until the signal plateaus and subsequently the NO introduction ceases. The sensors, then bathed in UHP $N_2$, return to their baseline resistance. The process when repeated will produce a series of spike-like features. We interpret the observed process by dividing the data in FIG. 6.3A-E into regions. In the first region, the sensors are baseline stabilized using an $N_2$ flow. The process of baseline stabilization differs somewhat for each treated sensor. In the second region, NO is introduced and the resistance drops sharply. This is a surprising response for the weak base NO, especially upon comparison with $NH_3$, $PH_3$, and $H_2S$. It is suggested that this resistance drop results as the NO free radical interacts with the oxygen atom sites on the nanostructure modified porous silicon surface. We suggest that a process similar to but distinct from the mechanism outlined in Equations (1) and (2) postulated previously[7,8] for the interaction of NO with n-type doped $SnO_2$ thin films, produces a transient $NO_2$ concentration on the nanostructure treated PS surface. This process can lead to the sharp decrease in resistance observed for "p-type" silicon. The proposed mechanism produces an electron for the conduction band of the metal oxide. Here, we again note that the introduction of $NO_2$ to the "p-type" PS surface used in this study leads to a significant drop in resistance as demonstrated in FIG. 6.2, consistent with the observed resistance decrease in FIG. 6.3A-E.

We interpret the rise in signal in the region following the resistance minimum as resulting from the direct interaction of NO with the modified PS interface. We suggest that the resistance increases in response to NO after the conversion process to produce $NO_2$, which depletes the available oxygen atoms at the treated PS surface, is completed. In the final region, as the system is returned to the UHP $N_2$ purge gas flow, the response returns closely to "baseline". We evaluate the response to NO for the untreated and nanostructure treated PS sensors by comparing the resistance minimum and rise in resistance from the minimum point to the point at which the NO introduction to the sensor is terminated. In other words, we compare the resistance recorded at the minimum in the resistance response to that following and corresponding to the plateau region before the NO is no longer introduced to the sensor.

Although we operate the sensors in an unsaturated mode, there is some baseline drift and the sensor response and recovery times can differ. However, the data in FIG. 6.3A-E suggests a rapid initial response and a reasonable recovery to baseline within the 300 s window indicated for NO introduction followed by the $N_2$ purge reintroduction in FIG. 6.3A-E. Further, this corresponds to the recovery time for a rather open configuration (FIG. 2—Ref. 18). The return to full baseline recovery can be further improved by more tightly constraining the gas flow path to the sensor surface as is discussed in Ref. 3. However, the long term return to baseline is indicated for the $SnO_x$ treated PS sensor in FIG. 6.3E.

Discussion

There have been several previous studies of NO and $NO_2$[4-17], however, for the purpose of the present discussion, we will focus on the studies of Williams and Coles[7] and Sberveglieri et al.[8] These authors have studied the response of several doped $SnO_2$ films to $NO_x$ (NO, $NO_2$). Sberveglieri et al.[8], in studying Cd doped $SnO_2$ sensors, first observed a transient (~30 s) "reverse sensitivity" (increase in conductance) followed by a decrease in the conductance when an NO/dry air mixture was introduced to the doped $SnO_2$ sensors. The process could not be observed when $N_2$ and argon were used as carriers. These authors attributed this behavior to the initial reaction of NO with surface oxygen atom species to form $NO_2$ (Eqs. 1 and 2) with the subsequent injection of an electron into the conduction band of $SnO_2$, thus increasing the conductance. They suggested that this process was followed by $NO_2$ adsorption to the surface causing an electron depletion (majority carriers), the buildup of a Shottky barrier, and the decrease of the electrical conductance.

Williams and Coles[7] have studied the $NO_x$ response of $SnO_2$ based sensors, $SnO_2$—$Bi_2O_3$, undoped $SnO_2$ calcined at 1500° C., and thin film $SnO_2$ generated from a sputtered Sn layer. In monitoring the $SnO_2$—$Bi_2O_3$ system at temperatures less than 300° C., the authors also found a transient reverse sensitivity, observed both in dry air and nitrogen gas, and implying that NO can react directly with surface oxygen atoms on the semiconductor lattice. In contrast, they found that pre-calcined $SnO_2$ displayed a conventional (significant increase in sensor resistance) $NO_x$ response for this n-type semiconductor device (at temperatures in excess of 265° C.).

The two outlined studies both suggest the potential importance of surface oxygen atom interactions with NO to form $NO_2$. In the present study, carried out on a nanostructure modified "p-type" porous silicon interface at room temperature, the results we obtain portend of a similar mechanism. We will suggest that the behavior observed in the present observation of a sharp transient dip in resistance can be explained through the coupling of $NO_x$ acid/base chemistry with the properties of an extrinsic "p-type" semiconductor.

NO and $NO_2$ are distinct as NO corresponds to a weak (soft) free radical base whereas $NO_2$ represents a moderately strong (hard) acid. In concert, the NO doublet radical has a singly occupied HOMO as compared to the doubly occupied HOMO of the bases ammonia and phosphine. The open shell nature of NO would suggest the possibility of a distinctly different interaction with "p-type" PS[1] and the nanostructure treated PS interface. In addition, NO can bind an electron which $NH_3$ and $PH_3$ cannot. These differences are born out through a comparison of the results displayed in FIG. 5.8A-C where we compare the nature of the PS-based responses for NO, $NH_3$ and $PH_3$. This figure would appear to demonstrate the importance of the free radical nature of NO. We observe the transient decrease in resistance on a "p-type" or modified "p-type" PS interface only for the NO radical and not for the exemplary bases $NH_3$ and $PH_3$. In fact, we also do not observe this transient behavior for $H_2S^1$, $SO_2^{27}$, or $CO^{1,19}$, all moderate to weak (soft) bases. Further, as FIG. 6.2 demonstrates, $NO_2$, a moderate acid, induces a decrease in the resistance of a "p-type" porous silicon surface as would be expected when an acid removes an electron from "p-type" PS and thus increases the majority carrier concentration.

The nanostructured metal oxide islands[19] we have deposited to the surface of PS to increase the surface activity of PS have been selected to modify and direct physisorption/weak chemisorption for rapidly responding, reversible PS gas sensors. We have developed a complementary concept[1] (IHSAB) to that formulated by Pearson[28] for "hard" and "soft" acid base interactions in order to explain the trends observed in the responses of several PS sensor-analyte systems. In the HSAB concept[28], which was developed for aqueous solutions, the interaction strength is correlated with the relative acidity and basicity of several surveyed reactants which are exemplified in Table II, Ex. 3. The ions and molecules indicated in this table, as they interact to form complexes and molecules are classified as strong, borderline, or weak acids and bases dependent on their binding as ligands. Hard species, both acids and bases, tend to be small slightly polarizable species and soft acids and bases tend to be larger and more polarizable. Further, the Pearson principle states that strong acids react with strong bases and weak acids interact with weak bases, resulting in significant ionic and covalent bonding respectively. In contrast, we have found that a nanostructure treated PS gas sensor can be made to behave in a reversible physisorption/weak chemisorption mode, developing the IHSAB concept to explain this behavior[1].

TABLE II

Example 5. Some examples of Hard and Soft Acids and Bases.

| | Hard | Borderline | Soft |
|---|---|---|---|
| Acids | $H^{+\,*}$, $Li^+$, $Na^+$, $K^+$, $Ag^+$, $Ti^+$, $Hg^+$, $Be^{2+}$, $Mg^{2+}$, $Ca^{2+}$, $Pt^{2+}$, $Hg^{2+}$, $Cr^{2+}$, $Cr^{3+}$, $Al^{3+}$, $SO_3$, $BF_3$ | $NO_2$, $Fe^{2+}$, $Co^{2+}$, $Ni^{2+}$, $Cu^{2+}$, $Zn^{2+}$, $Pb^{2+}$, $BBr_3$ | $Cu^+$, $Au^+$, $Pd^{2+}$, $Cd^{2+}$, $BH_3$ |
| Bases | $F^-$, $OH^-$, $H_2O$, $NH_3$, CO, I, $CO_3^{2-}$, $NO_3^-$, $O^{2-}$, $C_6H_5$, $SO_4^{2-}$, $PO_4^{3-}$, $ClO_4^-$ | $NO_2^-$, $SO_3^{2-}$, $Br^-$, $N_3^-$, $N_2$, $SO_2$, $C_6H_5N$, SCN | NO, $H^-$, $R^-$, $CN^-$, $R_3P$, $R_2S$ |

This (*) standard notation does not indicate an ion, but rather the effective charge of an element bound to a ligand. For example $SiO_2$ corresponds to $Si^{+4}$ and SiO corresponds to $Si^{+2}$.

In the IHSAB model, the physisorption process is found to dominate for primarily strong acid-weak base and weak acid-strong base interactions. We force a mismatch between the molecular electronic structure of the treated PS surface and the analyte of interest to (1) maximize the reversible interaction with the surface, and (2) create an array of variable responses which provide a signature for the analyte of interest. By assessing the trends inherent to the IHSAB principle, a first order selection can be made for the appropriate modification of the PS hybrid interface with fractional nanostructured metal/metal oxide deposits to create a range of "reversible" sensitivities for a number of gases. It is important to emphasize that the nanostructured oxide deposits to which we refer act to influence the degree of physisorption at the PS interface and that these metal oxides do not coat the PS surface. The response of the sensor system, resulting in an increase or decrease in resistance is dictated to first order by the nature of the extrinsic semiconductor. The fractional metal oxide deposition serves to enhance the degree of response of the modified "p-type" PS surface.

NO is a soft (moderately weak) base. Thus, its position among several bases as indicated in Table II, Ex. 5. Table II, Ex. 5 summarizes primarily the acid-base strength of ions associated with the oxides. From this table, the IHSAB model suggests that NO will give the best reversible response with an $SnO_x$ modified PS surface since $Sn^{+4}$ represents a strong acid. $Ni^{+2}O$, a borderline acid ($Ni^{2+}$), provides a decreased response as it lies closer to the weak base NO, however, this response is notably better than that of $(Au_xO)Au^{0,\,+1}$ which is again better than that for $(Cu_xO)Cu^{+1,+2}$. The soft base-hard acid interaction of NO with an $SnO_2$ nanostructured deposited surface leads to a substantial resistance response increase relative to PS. This is the signature of the reversible interaction of a strongly acidic surface with a weak base[1]. The NO response to the gold, copper, and nickel treated PS interface (Table I, Ex. 5), while considerably muted relative to the tin treated surface provides distinctly different response changes which might be employed in an array-based format. The data suggests that the acid strength of a $(Cu_xO)Cu^{+1,\,+2}$ deposited PS interface is closely matched to the base strength of NO. The gold clustered oxides represent weak bases which lie to the weak acid side of NO, again increasing the sensor response as a mild acid-base mismatch is promoted.

The inverse HSAB model[1] suggests that the proper combination of nanostructure deposition techniques could be employed to produce combinations of array based multiple sensor devices of varying sensitivity to a variety of gases and that a matrix of array responses might be correlated to selectivity for a given gas mixture. It is also important to note that the results in this study and similar studies[1,3,18,19] are obtained at room temperature using nanostructure deposits on the PS surface and not a film coating. We have also observed that these systems can be operated at notably higher temperatures[29], increasing the observed resistance changes; however, it is important that we maintain a fractional nanostructure surface deposition. We have found that, as the concentration of the nanostructure deposit is increased, we observe the onset of noisy signals followed by a significant signal quenching. We attribute this behavior to increased cross-talk between the deposited nanostructured oxide islands[1,3,18,19] which can lead eventually to an effective shorting of the sensor response.

Within the framework of the IHSAB model, the observed trends are consistent with the observations of Sberveglieri et al.[8] and those of Williams and Coles[7]. The $NO_2$ molecule, as a moderately strong acid, withdraws electrons from the "p-type" PS surface increasing the majority charge carrier concentration and decreasing the resistance (FIG. 6.2). Thus, if $NO_2$ is created at the PS interface, we expect to observe a significant transient decrease in the resistance associated with the PS sensor. However, once the O atom concentration on the surface of the PS sensor is depleted, the observed signal and the resistance begins to rise (FIG. 6.3A-E). This is consistent with an increase in resistance resulting as the interaction of the weak base, NO, overcomes the transient $NO_2$ formation and depletes majority carrier concentration. In contrast, for an "n-type" semiconductor, the introduction of NO would be expected to increase the majority carrier concentration, leading to a decrease in resistance. The results that we obtain for "p-type" PS at room temperature, therefore suggest that the drop in conductance observed by Sberveglieri et al[8]. may indeed result from the formation of a Schottky barrier as $NO_2$ absorbs to their "n-type" $SnO_2$ surface.

It is relevant that we compare the positive aspects of the present sensor and complementary technologies. The present sensor system is capable of monitoring NO at the level of 650 ppb and $NO_2$ at a much lower level based several additional tests in our laboratory. Levels of 12 ppb in dry air and 50 ppb in humid air have been reported for PS. These levels compare favorably with inexpensive advertised room temperature Electrochemical sensors (0-2500 ppm NO, 0-500 ppm $NO_2$)[30]. The notable attributes of the present inexpensive and low power consuming PS devices are detailed elsewhere[1,2]. Electrochemical sensors are also known for their low power operation, rapid response, and insensitivity to humidity and IT Gmbh[30] appears to have developed impressively sensitive and inexpensive devices.

Traditional metal oxide sensors (FIG. 6.4), when compared to electrochemical sensors are slightly less costly to produce, but are still significantly more complex than the PS sensor system considered in the present and other[1,3,18,19] discussions. Most importantly, they require a sensor element operative at elevated temperatures. The latter requirement can be problematic. First, a power consuming heating element must be provided with the sensor housing to precisely control the temperature of the sensor element. This control is, in large part, intimately tied to the correct identification of the gas of interest. The sensor must operate at well defined elevated temperatures for the valid identification of individual gases. Distinguishing one gas from another thus requires that the heating element and sensor be well separated (channel) from the remaining electronics. This in turn means that this configuration can be greatly affected by an impinging combustion or flue gas, rendering moot the correct identification of gaseous species in the flow. In contrast the PS sensor configuration depicted in FIG. 6.4 is far simpler and does not require the complexity of a system separated sensor/heater configuration[1]. In a heat sunk environment, it is potentially capable of operation in a high temperature gas flow. This simplicity and capability of operation is significant. Further, the attributes of a porous silicon technology developed by combining array generation through the coupling of acid/base chemistry with the properties of extrinsic semiconductors suggests a general road map to array development, and understanding of the nuances of this process.

Conclusion

A PS gas sensor has been used to detect NO employing different nanostructured oxidized metal nanoparticle depositions. These depositions are verified with XPS measurements[3]. We have achieved significant improvements in the sensor response when naked "p-type" porous silicon is coated with $SnO_2$ dominant nanostructures. An approach to a general metal oxide deposition strategy is based upon an IHSAB concept designed to create a dominant physisorptive interaction for the modified PS interface. The behavior that we observe here may be useful for the creation of a portable sensor system for the early detection of the onset of an asthma attack. Here, the buildup of NO can be sensed by an NO sensor array producing a signature of increasing and differing resistances for the nanostructure modified PS interface. As the concentration of NO increases, it will be converted to $NO_2$. The interaction of $NO_2$ with a "p-type" PS or nanostructure modified "p-type" PS sensor results in a decrease in the sensor resistance Thus the signature of an asthma attack should result in a sequence of increasing (NO) and subsequently decreasing ($NO_2$) measured resistances in an array based device.

References for Example 5, each of which is incorporated by reference

1. J. L. Gole, S. Ozdemir, *ChemPhysChem*, 11, 2573-2581 (2010).
2. "Efficient Nanostructure Modified Interfaces for Array-based Sensing Based on the Novel Application of Hard/Soft Acid/Base Interactions," James L. Gole and S. Ozdemir, Phys. Stat. Solidi., in press.
3. Serdar Ozdemir and James J. Gole, *Sens. and Actuators: B*, 151, 274-280, (2010).
4. (a) W. Miekisch, J. K. Schubert, G. F. E. Noeldge-Schomburg, *Clinica Chemica Acta*, 347, 25-39 (2004);
   (b) P. P. R. Rosias, E. Doompeling, H. J. E. Hendriks, J. W. C. M. Heijnens, R. A. M. G. Donckerwolcke, Q. Jobsis, *Pediatric Allergy and Immunology*, 15, 4-19 (2004).
5. (a) M. R. Zeilder, E. C. Kleerup, D. P. Tashkin, *Current Opinions in Pulmonary Medicine*, 10, No. 1:31-36 (2004);
   (b) S. A. Kharitonov, P. J. Barnes, *Biomarkers*, 7, 1-32 (2002).
6. L. Pancheri, C. J. Oton, Z. Gaburro, G. Soncini, and L. Pavesi, *Sens. and Actuators B*, 89, 237-239 (2003).
7. Geraint Williams and Gary S. V. Coles, *Sens. and Actuators B*, 15-16, 349-353 (1993).
8. G. Sberveglieri, S. Groppelli, and P. Nelli, *Sens. and Actuators B*, 4, 457-461 (1991).
9. L. Boarino, C. Baratto, F. Geobaldo, G. Amato, E. Comini, A. M. Rossi, G. Faglia, G. Lerondel, G. Sberveglieri, *Mat. Sci. Eng. B Solid*, 69-70, 210-214 (2000).
10. S. Ozdemir, J. L. Gole, *Curr. Opin. Solid Stater Mater. Sci.* 11, 92-100 (2007).
11. C. Burratto, G, Faglia, E. Comini, G. Sberveglieri, A. Taroni, V. La Ferrara, L. Quercia, and G. Francia, *Sens. and Actuators B*, 77, 62-66 (2001).
12. M. J. Sailor, in: L. Canham (Ed.), Properties of Porous Silicon. IEE, London, UK, 1997, pg. 364.
13. S. R. Morrison, *Sensors and Actuators*, 2, 329-341 (1982).
14. S. R. Morrison, *Sensors and Actuators*, 12, 425-440 (1987).
15. G. Heiland, *Sensors and Actuators*, 2, 343-361 (1982).
16. S. C. Chang, *IEEE, Trans. Electron Devices*, ED26, 1875-80 (1979).
17. S. C. Chang, *J. Vac. Sci. Technol.*, 17, 366-369 (1980).
18. S. Lewis, J. DeBoer, J. L. Gole, P. Hesketh, *Sens. Actuators B*, 110, 54-65 (2005).
19. J. L. Gole, S. Lewis, S. Lee, *Phys. Stat. Sol A*, 204, 1417-1422 (2007).
20. A. G. Nassiopoulos, Local formation and patterning of porous silicon, in: L. Canham (Ed.), Properties of porous silicon, IEE-Books, London, 1997, pp. 77-80.
21. Modification of procedures in H. M. Van Noort, B. C. M. Meenderink, and A. J. Molenaar, *J. Electrochem. Soc.*, 133, 263-5 (1986). by L. Seals and J. L. Gole.
22. E. K. Yung, L. T. Romankiw, R. C. Alkire, *J. Electrochem. Soc.*, 136, 206-15 (1989).
23. L. Seals, private communication.
24. M. Schlesinger, M. Paunovic (Eds.), Modern Electroplating (4th Ed.), Wiley, New York, 2000.
25. Serdar Ozdemir and James Gole, ECS Transactions, 33(8), 111-115 (2010).

26. G. Korotcenkov, B. K. Cho, *Crit. Rev. Solid State Mater. Sci.*, 35, 1-37 (2010).
27. Serdar Ozdemir, Thomas B. Osburn, James L. Gole, work in progress.
28. R. G. Pearson, *Coordin. Chem. Rev,* 100, 403-25 (1990).
29. J. DeBoer, S. Lewis, and J. L. Gole, unpublished.
30. Please see www.it-wismar.de.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

Therefore, the following is claimed:

1. A method of selecting a nanostructured deposit for a conductometric porous silicon gas sensor, comprising:
    exposing a gas to a plurality of testing conductometric porous silicon gas sensors, wherein each of the testing conductometric porous silicon gas sensors is operative to transduce the presence of a gas into an impedance change, wherein the impedance change correlates to the gas concentration,
    wherein the testing conductometric porous silicon gas sensor has a porous silicon layer, wherein one or more of the testing conductometric porous silicon gas sensors has a nanostructured deposit disposed on the porous silicon layer, wherein the nanostructured deposit is selected from the group consisting of: a nanostructured deposit having the characteristic of a hard acid, a nanostructured deposit having the characteristic of an intermediate acid, a nanostructured deposit having the characteristic of a soft acid, a nanostructured deposit having the characteristic of a hard base, a nanostructured deposit having the characteristic of an intermediate base, and a nanostructured deposit having the characteristic of a soft base,
    measuring an impedance change using each of the testing conductometric porous silicon gas sensors relative to a standard testing conductometric porous silicon gas sensor, and
    selecting the nanostructured deposit using the concept that the nanostructured deposit and the gas have complementary characteristics based on the interactions of two of the following: a hard acid, an intermediate acid, a soft acid, a hard base, an intermediate base, and a soft base, where such interaction between the gas and the nanostructured deposit determines the measured impedance change, wherein the combination of the nanostructured deposit and the gas generates a range of impedance changes, the greatest impedance change being determined by the maximum hard acid/soft base or hard base/soft acid mismatch between the gas and the nanostructured deposit.

2. The method of claim 1, wherein if the gas has the characteristic of a hard acid, a nanostructured deposit having the characteristic of a soft base is selected to maximize the impedance change.

3. The method of claim 1, wherein if the gas has the characteristic of a hard base, a nanostructured deposit having the characteristic of a soft acid is selected to maximize the impedance change.

4. The method of claim 1, wherein if the gas has the characteristic of a hard acid, a nanostructured deposit that does not have the characteristic of a hard base is selected, wherein if the gas has the characteristic of an intermediate acid, a nanostructured deposit that does not have the characteristic of an intermediate base is selected, wherein if the gas has the characteristic of a soft acid, a nanostructured deposit that does not have the characteristic of a soft base is selected, wherein if the gas has the characteristic of a hard base, a nanostructured deposit that does not have the characteristic of a hard acid is selected, wherein if the gas has the characteristic of an intermediate base, a nanostructured deposit that does not have the characteristic of an intermediate acid is selected, wherein if the gas has the characteristic of a soft base, a nanostructured deposit that does not have the characteristic of a soft acid is selected.

5. The method of claim 1, wherein exposing includes exposing the gas to two conductometric porous silicon gas sensors, wherein one of the conductometric porous silicon gas sensors has a nanostructured deposit having the characteristic of a hard acid and the other of the conductometric porous silicon gas sensors has a nanostructured deposit having a characteristic of a soft acid, the combination creating a range of impedance changes when interacting with a gas that is a base.

6. The method of claim 1, wherein exposing includes exposing the gas to two conductometric porous silicon gas sensors, wherein one of the conductometric porous silicon gas sensors has a nanostructured deposit having the characteristic of a hard base and the other of the conductometric porous silicon gas sensors has a nanostructured deposit having a characteristic of a soft base, the combination creating a range of impedance changes when interacting with a gas that is an acid.

7. The method of claim 1, wherein exposing includes exposing the gas to three conductometric porous silicon gas sensors, wherein one of the conductometric porous silicon gas sensors has a nanostructured deposit having the characteristic of a hard acid, one of the other of the conductometric porous silicon gas sensors has a nanostructured deposit having a characteristic of a soft acid, and the other of the conductometric porous silicon gas sensors has a nanostructured deposit having a characteristic of an intermediate acid, the combination creating a range of impedance changes when interacting with a gas that is a base.

8. The method of claim 1, wherein exposing includes exposing the gas to four or more conductometric porous silicon gas sensors, wherein the nanostructured deposit for each of the conductometric porous silicon gas sensors is selected from the group consisting of: a nanostructured deposit having the characteristic of a hard acid, a nanostructured deposit having the characteristic of a intermediate acid, a nanostructured deposit having the characteristic of a soft acid.

9. The method of claim 1, wherein exposing includes exposing the gas to an array of conductometric porous silicon gas sensors, wherein the nanostructured deposit for each of the conductometric porous silicon gas sensors is selected from the group consisting of: a nanostructured deposit having the characteristic of a hard acid, a nanostructured deposit having the characteristic of a intermediate acid, a nanostructured deposit having the characteristic of a soft acid.

10. The method of claim 1, wherein exposing includes exposing the gas to four or more conductometric porous silicon gas sensors, wherein the nanostructured deposit for each of the conductometric porous silicon gas sensors is selected from the group consisting of: a nanostructured deposit having the characteristic of a hard base, a nanostructured deposit having the characteristic of a intermediate base, a nanostructured deposit having the characteristic of a soft base.

11. The method of claim 1, wherein exposing includes exposing the gas to an array of conductometric porous silicon gas sensors, wherein the nanostructured deposit for each of the conductometric porous silicon gas sensors is selected from the group consisting of: a nanostructured deposit having the characteristic of a hard base, a nanostructured deposit having the characteristic of a intermediate base, a nanostructured deposit having the characteristic of a soft base.

12. The method of claim 1, wherein exposing includes exposing the gas to three conductometric porous silicon gas sensors, wherein one of the conductometric porous silicon gas sensors has a nanostructured deposit having the characteristic of a hard base, one of the other of the conductometric porous silicon gas sensors has a nanostructured deposit having a characteristic of a soft base, and the other of the conductometric porous silicon gas sensors has a nanostructured deposit having a characteristic of an intermediate base, the combination creating a range of impedance changes when interacting with a gas that is an acid.

13. The method of claim 1, wherein the the nanostructured deposit provides a fractional coverage of the porous silicon layer.

14. A method of detecting a gas based on the acidic or basic characteristic of the gas using a conductometric porous silicon gas sensor, comprising:
exposing a gas to one or more conductometric porous silicon gas sensors, wherein each of the conductometric porous silicon gas sensors is operative to transduce the presence of a gas into an impedance change, wherein the impedance change correlates to the gas concentration,
wherein the conductometric porous silicon gas sensor has a porous silicon layer, wherein one or more of the conductometric porous silicon gas sensors has a nanostructured deposit disposed on the porous silicon layer, wherein the nanostructured deposit is selected from the group consisting of: a nanostructured deposit having the characteristic of a hard acid, a nanostructured deposit having the characteristic of an intermediate acid, a nanostructured deposit having the characteristic of a soft acid, a nanostructured deposit having the characteristic of a hard base, a nanostructured deposit having the characteristic of an intermediate base, and a nanostructured deposit having the characteristic of a soft base, wherein the nanostructured deposit used is based on the concept that the nanostructured deposit and the gas have complementary characteristics based on the interactions of two of the following: a hard acid, an intermediate acid, a soft acid, a hard base, an intermediate base, and a soft base, where such interaction between the gas and the nanostructured deposit determines the measured impedance change, wherein the greatest impedance change is obtained by using a nanostructured deposit and the gas promoting an interaction that generates the maximum acid-base mismatch;
measuring the impedance change using one or more of the conductometric porous silicon gas sensors relative to a standard conductometric porous silicon gas sensor; and
obtaining the greatest impedance change using the conductometric porous silicon gas sensor that has the nanoparticle deposit that interact with the gas to produce the maximum acid-base mismatch.

15. The method of claim 14, wherein the gas has the characteristic of a hard acid and the nanostructured deposit has the characteristic of a soft base for maximum impedance response.

16. The method of claim 14, wherein the gas has the characteristic of a hard base and the nanostructured deposit has the characteristic of a soft acid for maximum impedance response.

17. The method of claim 14, wherein the the nanostructured deposit provides a fractional coverage of the porous silicon layer.

18. A device, comprising:
a conductometric porous silicon gas sensor including a silicon substrate having a porous silicon layer, wherein a nanostructured deposit is disposed on a portion of the porous silicon layer,
wherein the conductometric porous silicon gas sensor is operative to transduce the presence of a gas into an impedance change, wherein the impedance change correlates to the gas concentration,
wherein if the gas of interest has the characteristic of a hard base, the nanostructured deposit does not have the characteristics of a hard acid, wherein if the gas of interest has the characteristic of a soft base, the nanostructured deposit does not have the characteristics of a soft acid, wherein if the gas of interest has the characteristic of an intermediate base, the nanostructured deposit does not have the characteristic of an intermediate acid, wherein if the gas of interest has the characteristic of a hard acid, the nanostructured deposit does not have the characteristics of a hard base, wherein if the gas of interest has the characteristic of a soft acid, the nanostructured deposit does not have the characteristic of a soft base, wherein if the gas of interest has the characteristic of an intermediate acid, the nanostructured deposit does not have the characteristic of an intermediate base.

19. The device of claim 18, wherein the gas has the characteristic of a hard acid and the nanostructured deposit has the characteristic of a soft base to produce a maximum impedance change.

20. The device of claim 18, wherein the gas has the characteristic of a hard base and the nanostructured deposit has the characteristic of a soft acid to produce a maximum impedance change.

21. The device of claim 18, wherein the the nanostructured deposit provides a fractional coverage of the porous silicon layer.

22. A method of determining the acidic or basic characteristic of a gas, comprising:
exposing a gas to a plurality of conductometric porous silicon gas sensors, wherein each of the conductometric porous silicon gas sensors is operative to transduce the presence of a gas into an impedance change, wherein the impedance change correlates to the gas concentration, wherein the conductometric porous silicon gas sensor has a porous silicon layer, wherein one or more of the conductometric porous silicon gas sensors has a nanostructured deposit disposed on the porous silicon layer, wherein the nanostructured deposit is selected from the group consisting of: a nanostructured deposit having the characteristic of a hard acid, a nanostructured deposit having the characteristic of an intermediate acid, a nanostructured deposit having the characteristic of a soft acid, a nanostructured deposit having the characteristic of a hard base, a nanostructured deposit having the characteristic of an intermediate base, and a nanostructured deposit having the characteristic of a soft base, wherein the nanostructured deposit used is based on the concept that the nanostructured deposit and the gas have complementary characteristics based on the interactions of two of the following: a hard acid, an intermediate acid, a soft acid, a hard base, an intermediate base, and a soft base, where such interaction between the gas and the nanostructured deposit determines the measured impedance change, measuring an impedance change using each of the conductometric porous silicon gas sensors relative to a standard conductometric porous silicon gas sensor, and determining if the gas has the characteristic of a hard acid, an intermediate acid, a soft acid, a hard base, an intermediate base, or a soft base, based on the impedance change of the conductometric porous silicon gas sensors.

23. The method of claim 22, wherein a) if one of the conductometric porous silicon gas sensors has a nanostructured deposit having the characteristic of a hard acid and b) wherein if one of the conductometric porous silicon gas sensors has a nanostructured deposit having the characteristic of a soft acid, and the impedance change is greater for a) then the interacting gas is not a hard base.

24. The method of claim 22, wherein a) if one of the conductometric porous silicon gas sensors has a nanostructured deposit having the characteristic of a hard acid and b) wherein if one of the conductometric porous silicon gas sensors has a nanostructured deposit having the characteristic of a soft acid, and the impedance change is greater for b) then the interacting gas is not a soft base.

25. The device of claim 22, wherein the the nanostructured deposit provides a fractional coverage of the porous silicon layer.

* * * * *

UNITED STATES PATENT AND TRADEMARK OFFICE
CERTIFICATE OF CORRECTION

PATENT NO.         : 8,573,030 B2
APPLICATION NO.    : 13/031430
DATED              : November 5, 2013
INVENTOR(S)        : Gole It is certified that error appears in the above-identified patent and that said Letters Patent is hereby corrected as shown below:

In the Specification

Column 22, line 49, delete "Modifications," and replace with --modifications,--

Column 33, line 56, delete "[47]" and replace with --[47]--

Column 33, line 57, delete "[33, 37]" and replace with --[33, 37]--

Column 33, line 63, delete "[51, 52]" and replace with --[51, 52]--

Column 39, line 25, delete "[1,2]" and replace with --[1,2]--

Column 39, line 43, delete "[5]" and replace with --[5]--

Column 39, line 45, delete "[6,7]" and replace with --[6,7]--

Column 40, line 13, delete "[5]" and replace with --[5]--

Column 40, line 16, delete "[8]" and replace with --[8]--

Column 40, line 17, delete "[7]" and replace with --[7]--

Column 40, line 19, delete "[6]" and replace with --[6]--

Column 40, line 21, delete "[8]" and replace with --[8]--

Column 40, line 30, delete "[7a]" and replace with --[7a]--

Column 41, line 10, delete "[6,11]" and replace with --[6,11]--

Column 41, line 12, delete "[12]" and replace with --[12]--

Signed and Sealed this
Twenty-ninth Day of July, 2014

Michelle K. Lee
*Deputy Director of the United States Patent and Trademark Office*

CERTIFICATE OF CORRECTION (continued)
U.S. Pat. No. 8,573,030 B2

Column 41, line 20, delete "[7,12,13]]" and replace with --[7,12,13]--

Column 41, line 23, delete "[8]]" and replace with --[8]--

Column 41, line 61, delete "[14]]" and replace with --[14]--

Column 42, line 3, delete "[5]]" and replace with --[5]--

Column 42, line 6, delete "[15]]" and replace with --[15]--

Column 42, line 42, delete "[2,4,16]]" and replace with --[2,4,16]--

Column 42, line 51, delete "[17-19]]" and replace with --[17-19]--

Column 42, line 53, delete "[17]]" and replace with --[17]--

Column 42, line 54, delete "[18]]" and replace with --[18]--

Column 42, line 54, delete "[19]]" and replace with --[19]--

Column 42, line 59, delete "[4]]" and replace with --[4]--

Column 43, line 5, delete "[2,4,20,21]]" and replace with --[2,4,20,21]--

Column 43, line 7, delete "[21]]" and replace with --[21]--

Column 43, line 12, delete "[21]]" and replace with --[21]--

Column 43, line 14, delete "[2,20,21]]" and replace with --[2,20,21]--

Column 43, line 18, delete "[2,20]]" and replace with --[2,20]--

Column 43, line 21, delete "[21]]" and replace with --[21]--

Column 43, line 35, delete "[22]]" and replace with --[22]--

Column 43, line 42, delete "[21]]" and replace with --[21]--

Column 43, line 58, delete "[16]]" and replace with --[16]--

Column 44, line 30, delete "[5-9]]" and replace with --[5-9]--

Column 44, line 37, delete "[4,16(c),22]]" and replace with --[4,16(c),22]--

Column 45, line 8, delete "[20]]" and replace with --[20]--

Column 45, line 51, delete "[23]]" and replace with --[23]--

Column 46, lines 35 and 36, delete "$(Au^{0,+}{}_1)$" and replace with --$(Au^{0,+1})$--

CERTIFICATE OF CORRECTION (continued)
U.S. Pat. No. 8,573,030 B2

Column 46, line 65, delete "[24]]" and replace with --[24]--

Column 46, line 67, delete "[25]]" and replace with --[25]--

Column 47, line 27, delete "[26]]" and replace with --[26]--

Column 47, line 53, delete "[2,4,20]]" and replace with --[2,4,20]--

Column 47, line 56, delete "[22]]" and replace with --[22]--

Column 48, line 5, delete "[4]]" and replace with --[4]--

Column 48, line 7, delete "[27]]" and replace with --[27]--

Column 48, line 16, delete "[5-9]]" and replace with --[5-9]--

Column 48, line 29, delete "[28]]" and replace with --[28]--

Column 48, line 33, delete "[15]]" and replace with --[15]--

Column 49, line 8, delete "2-4" and replace with --[2-4]--

Column 49, line 10, delete "[2-4]]" and replace with --[2-4]--

Column 49, line 12, delete "[2-4]]" and replace with --[2-4]--

Column 49, line 23, delete "[20]]" and replace with --[20]--

Column 49, line 28, delete "[29]]" and replace with --[29]--

Column 49, line 33, delete "[2(a)]]" and replace with --[2(a)]--

Column 49, line 41, delete "[30]]" and replace with --[30]--

Column 49, line 41, delete "[31]]" and replace with --[31]--

Column 49, line 41, delete "[32]]" and replace with --[32]--

Column 49, line 42, delete "[33]]" and replace with --[33]--

Column 49, line 42, delete "[34]]" and replace with --[34]--

Column 49, line 42, delete "[35]]" and replace with --[35]--

Column 49, line 43, delete "[36]]" and replace with --[36]--

Column 49, line 44, delete "[2-4,20,21]]" and replace with --[2-4,20,21]--

Column 49, line 45, delete "[2-4]]" and replace with --[2-4]--

Column 49, line 56, delete "[36]]" and replace with --[36]--

Column 49, line 61, delete "[21]]" and replace with --[21]--

Column 53, line 54, delete "." between --)-- and --n--

Column 59, line 2, delete "[29]" and replace with --[29]--